United States Patent
Fisher

(12) 
(10) Patent No.: US 6,657,053 B1
(45) Date of Patent: Dec. 2, 2003

(54) RECIPROCAL SUBTRACTION DIFFERENTIAL DISPLAY

(75) Inventor: Paul B. Fisher, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 113 days.

(21) Appl. No.: 09/644,460

(22) Filed: Aug. 23, 2000

Related U.S. Application Data

(63) Continuation of application No. PCT/US99/04323, filed on Feb. 26, 1999.

(51) Int. Cl.[7] ................................................ C12N 15/12
(52) U.S. Cl. ..................................... 536/23.1; 536/23.5
(58) Field of Search ............................... 536/23.1, 23.5

(56) References Cited

U.S. PATENT DOCUMENTS

| | | | |
|---|---|---|---|
| 4,981,783 A | 1/1991 | Augenlicht | 435/6 |
| 5,599,672 A | 2/1997 | Liang et al. | 435/6 |

OTHER PUBLICATIONS

Duigou, G. J., et al., *Suppression Of The Progression Phenotype By 5–Azacytidine In Rat Embryo Cells Doubly Transformed by Type 5 denovirus and the Has–ras Oncogene* (1989) Annals of the New York Academy of Sciences 567:302–306 (Exhibit B).

Jiang, H. and Fisher, P. B., *Use Of A Sensitive And Efficient Subtraction Hybridization Protocol for the Identification of Genes Differentially Regulated During the Induction of Differentiation in Human Melanoma Cells*, (1993) Mol. Cell. Different. 1:285–299 (Exhibit C).

Jiang, H., *The Melanoma Differentiation Associated Gene mda–7 Suppresses Cancer Cell Growth*, (1996) Proc. Natl. Acad. Sci. USA 93:9160–65 (Exhibit D).

Jiang, H., et al., *Subtraction Hybridization Identifies a Novel Melanoma Differentiation Associated Gene, mda–7, Modulated During Human Melanoma Differentiation, Growth and Progression* (1995) Oncogene 11:2477–86 (Exhibit E).

Liang, P. and Pardee, A. B., *Recent Advances I Differential Display* (1995) Curr. Opinion Immunol. 7:274–80 (Exhibit F).

Liang, P. and Pardee, A. B., *Differential Display: A General Protocol* (1997) Meth.Mol. Biol. 85:3–11 (Exhibit G).

Liang, P. and Pardee, A. B., *Differential Display Of Eukaryotic Messenger RNA By Means Of The Polymerase Chain Reaction* (1992) Science 257:967–71 (Exhibit H).

Schena, M. et al., *Quantitative Monitoring Of Gene Expression Patterns With A Complementary DNA Microarray* (1995) Science 270:467–70 (Exhibit I).

Zhang, L., et al., *Gene Expression Profiles In Normal And Cancer Cells* (1997) Science 276:1268–72 (Exhibit J).

*Primary Examiner*—James Ketter
(74) *Attorney, Agent, or Firm*—Baker Botts L.L.P.

(57) ABSTRACT

This invention provides a method for identifying differentially expressed nucleic acids between two samples, comprising: a) selecting a first and second nucleic acid sample; b) producing libraries for the first and second nucleic acid sample; c) performing reciprocal subtraction between the libraries to produce two subtracted libraries; d) amplifying the two subtracted libraries; and e) comparing the two amplified subtracted libraries to identify differentially expressed nucleic acids. Also, this invention provides the above-described method, wherein the 3' primer used in the PCR amplification is an oligo dT 3' primer. This invention also provides the above-described methods, wherein the comparing of step e comprises using a gel to separate the nucleic acids from both of the libraries. This invention provides the isolated nucleic acid identified by the the above-described methods, wherein the nucleic was not previously known to be differentially expressed between the two samples.

4 Claims, 23 Drawing Sheets

FIG. 1

FIG. 3A
PEGen 7 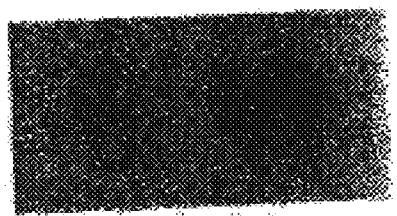
PEGen 8 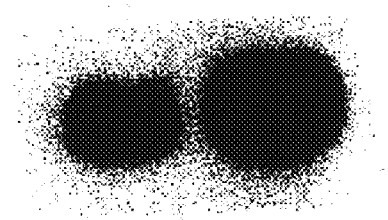
PEGen 21 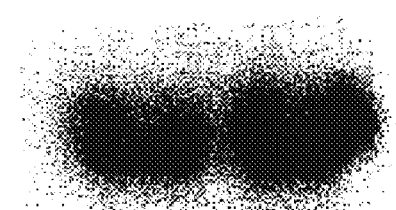
PSGen 12 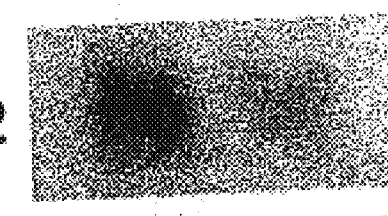
PSGen 13 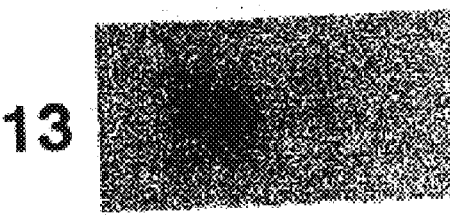

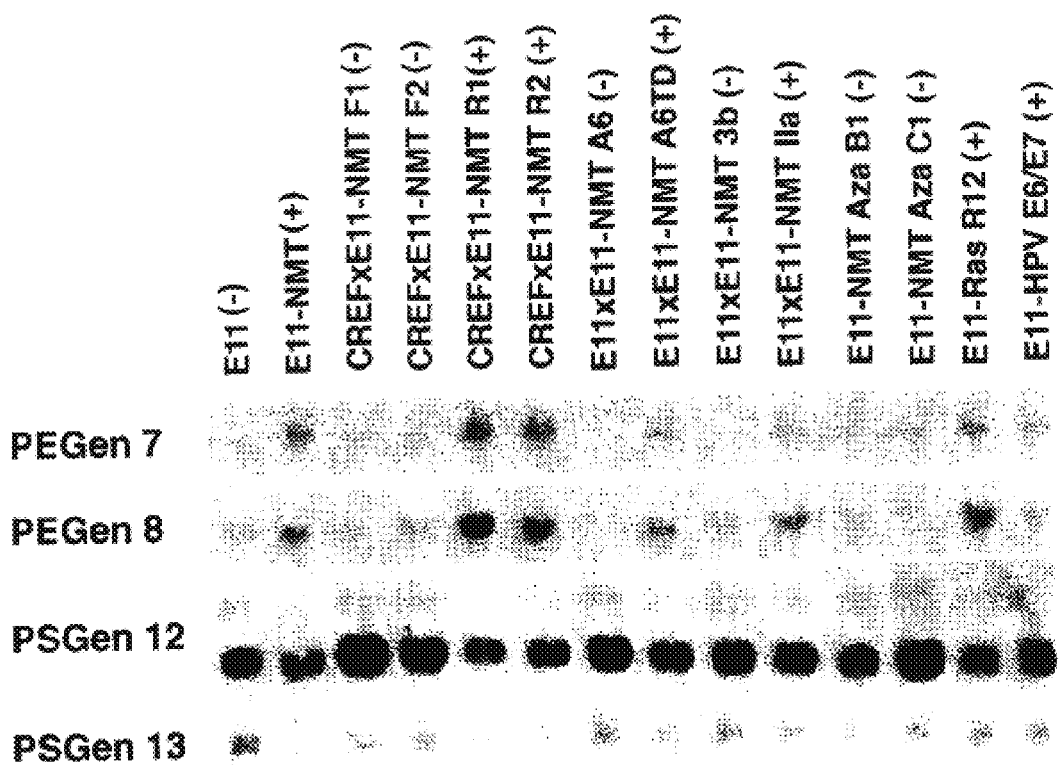

FIG. 5
PEGen 7-90% homology to human HPV16 E1BP

```
TAAANCGGTG GTACTGCTGC ACGGTCCTCC GGGTACTGGA AAGACATCCC
TTTGTAAGGC ATTAGCCCAG AAACTGACCA TCAGACTGTC AANCAGGTAC
CGGTATGGCC AGTTAATTGA AATAAACAGC CACAGCCTAT TTTCTAAGTG
GTNTTCAGAA AGTGGCAAGT TGGTAACTAA GATGTTCCAG AAGATTCANG
ACTTGATTGA TGATAANNAA NCTTTGGTGT TTGTCCTGAT TGATGANGTA
AGCACTCANN GGTACTCATT CTTNGTCTGC ATTGCCTCTT GCTATTACTG
CCTGATCCCT CTCATTTGGT TCACTGTGTC GCNANCTCTT TTCTATGGAT
CTTTTCCNAN CCACCCGTTT C
```

FIG. 6
PEGen 8-Rat phosphofructose kinase C

```
GTGACGTAGG GTCTGTTGCG TCAATGGTTA TAGCAAGTGA TGCTCTCTGA
TTATTACTGC TGACAATACT CGGCCAACAA TTCTTGCATA GAGTGCTGAT
AAATAACTAT GTTACAAAAA GGGGTGGTCC CTGGAGAACA TTACAGGCTT
CCCTAGGTAA GTGTGCAGGT CAGGAGACGG CATATTCAAT CAGATGGCTG
ATAGTTCTCC GTGGTTATGC ACCGGCTCCA GCTTGCCTAC GTCAC
```

FIG. 7
PEGen 13-Novel

```
GCAGCATGAT GAATTTAATG CAACAGTCAT AGCAGGGCAA GGGGAGAGAA
AGGCAGATGG ACTATCTGCA TCATCAAGCG AGGGCTTGTG TCGGCGGCTA
TGTGCAGAGA CGAGCAGGGC GAGGCACTTA AAAGCTGCTN GATGAAAATC
CACCCAGGAG AANTCTGGGC CTACGTCA

TGACGTAGGC CCAGACTTCT CCTGGGTGGA TTTTCATCCA GCAGCTTTTA
AGTGCCTCGC CCTGCTCGTC TCTGCACATA GCCGCCGACA CAAGCCCTCG
CTTGATGATG CAGATAGTCC ATCTGCCTTT CTCTCCCTT GCCTGCTAT
GACTGTTGCA TTAAATTCAT CATGCTGCCA AAAAAAAAA A
```

FIG. 8
PEGen 14-Novel

```
GCCATAAATA CACTTTATTT CATTCGAAAT GCATAATCAC ACTGGGAGCA
CTCCCTTTGG AGCACTCCTC TAGCAGCAGG TCCGAAGTGC TCCAGCATCG
TCAGCTGGCT CCAACACCTA CGTC
```

FIG. 9
PEGen 15-Novel

```
TTTTTTTTTT TTTGGAAACA GAATAAAGTG CTTTATTCTC TGGCTGGCTC
TCCTACGTCA C
```

FIG. 10
PEGen 21-94% homology to mouse FIN 14

```
TCGGCGATAG CATTGGAGCA AGTCTTATCA GCAAGCAATG TTTTCAGTTA
TGTTTCAAAG TTAAGAATGG GTTTAAACTT GCTGAACGTA AAGATTGACC
CTCAAGTCAC TGTAGCTTTA GTACTTGCTT ATTGTATTAG TTTANATGCT
AGCACCGCAT GTGCTCTGCA TATTCTGGTT TTATTAAAAT AAAAAGTTGA
ACTGCAAAAA AAAAAA
```

FIG. 11
PEGen 24-Novel

```
TTTTTTTTTT TTTTTTTTTT TTTTTTTTTT TTTTTTTTTT TNGCCAGGCT
ATGTCTCAGA CTTTATTATT ATTATTATTA TTATTATTAT TATAAATAAA
ACATGTNCTT TCAATTAGGT TACAANAGTA TTTATCTCCA TAACGCTTCT
TCATACATCC TTAGTTTTGG ATTAAAGTAC CATCCACCCC AACTCAAACT
GTAACCCCCA GTAATCCCCT CTAACGTGGA AATTTCTGGT TTAACAACTC
AGTTAACTGC CCCACAAACA GTGGGAGGCC GCTCTTGCAT GGCTATGCCA
CGTAACCCTT CACTGCTTCA CTTCTTCGCT GGCT
```

FIG. 12
PEGen 26-Rat poly ADP-ribose polymerase.

```
GACCGCTTGT ACCATCCAAC TTGCTTTGTC TTCTGCAGAG AGGAGGCTAA
AGCCCTTGAG CTGGCTGGCA CTGTACTCAG GCCGGAAGCC CAGCTCGTCC
CGGTTCTTGA CAAAGCAAGT TGGATGGTAC AAGCGG
```

FIG. 13
PEGen 28-Novel

```
TGCCGAGCTG GGTATTGTGA CGGTTGATAA TGGCGGCATC ATGTTGCCAG
GTACCGGGTA AGCAGACCTC AGAGCACAGC TTATTGTCCA GTGCTTTCAC
GCTCGCGACG TCAAAGTCAT TGTTATTGTC ACACTCCATG CCTAGAAATG
CGCATGTCCT CTGGCCATCT TCTTGCACAG GGGATCTGTC CTCTTCCTCC
ATGATATCAT TTCCCTCTGC ATCCTGCTCT CCAGCTGGAA GGCCAGCAAA
ATTGCTGTCT GGGGACTCTG CTGGGTCTC CTCCTCTTCT GAAGGGGCCC
TGCTAGCAGC TCGGCA
```

FIG. 14
PEGen 42-Novel

```
AGGGGTCTTG ATGGACTTGG GTCGGACATC TTAGTGACCT GTGAATTCTT
CTGTGGAGGC TGAGTCTCAC GTAGCCGAGT TTAATATCTG TGCTATTTAC
TAAAGTATCT GCCACCAAAT TGTACCAACT CATAGTTTTA TATGAATGTT
GATGAGTCTG TATCATAAAT AGAATTGTTG ATACATCCTT AATTTGTGCA
ATATTGTATG AAGAAGATTG TTATCAATTA AAACCACGCC TCTTTATGAT
CCTNNNAAAA AAAAAAAAAA AAAAAAAAAA AAAAAAAAAA AAAAAAAAAA
AACCNCCTCA AATCCATNGG TTCTAACCCA AAACCCT
```

FIG. 15
PEGen 43-Novel

```
TTTTTTTTTT CATACACCAT CAAACCAATT TTATTTCTAT AGCAACGTTT
CTCACGTCTG AACCTGAGAA TAAGTCACCA GCTCTTGACA GTAAACATGG
GCCCTATCAA ATTATATTAG ACTCCTCAGT GTCCCGCCAT GTGGCCTTGC
ACCAAATCAA TTAGTTTGAG GGCCAAAATC CTGTTGGGTT TCAAATAAAG
TGTCAGGTCA TAAGGAGGGG GAGGGACTCA ATTCATGGGA ACATTTTTAC
CTGTTCAAAT AGATAAACTG AATTGCCCTA TCTGTGGTCA CCTGGATCCA
AGACCCT
```

FIG. 16
PEGen 44-Novel

```
CCCTGACGAT AAATGGTAAG GAACTTTTTT TTTTTTTTTT TTTTTTTTTT
TTTTTTTTNC GAAATAAACA AACACAGCTT ATTATTTGGG GGAACATTAA
NTTCTATAAN TGAACACAAA ANAAAATTAA NANTTAATGG GGGGGTANAA
GGGACTTTGA ATCTATCTGG TATCATGACA TTGAAGCANA NACCTGANTG
ACCAGAAAGA GAGAGAGAGA GAGAGAGAGA GAGAGAGAGA GAGAGGTTTC
ATATGAGCTA GTGTTACAGG CTTTATTAGT CTATTAGTCA GGGACC
```

FIG. 17
PEGen 48-Novel

```
AATCGGGCTG GATGGGTGTA TCCGGCACTG TTTCGTAGCG GCAGCAACTG
GGTGCTTCTA TCTGAAAGCG GGCTTCACAA AAACTACTGC GCCACCCGAC
TCGCTGCGGC ATCGCCCGGT GGCGAGTACC GTATCGCCTT TCCTGGTGCA
GAAGAAGTGT TTACAGGAGG CGGTCATTTA CCGCAATCTG ATTCTGTTTT
TTATTCTCCC TGGCGGGTGA TCGCGATCGG CAGTTTGAAA ACGATCGTTG
AATCCACGCT CGGGAATGAT GTGGCTTCGC CGCCAACGCT TACTGACATT
TCATTTGTAC AGCCCGATT
```

FIG. 18
PSGen 1-80% homology to B. taurus supervillin

```
GCCGAGCTGT GTAAAACCAT CTATCCTCTG GCAGATCTAC TTGCCAGGCC
ACTCCCAGGG GGGGTAGACC CTCTAAAGCT TGAGATTTAT CTTACAGATG
AAGACTTCGA GTTTGCACTC GACATGACCA GAGATGAATT CAACGCACTG
CCCACCTGGA AGCAAATGAA CCTGAAGAAA GCGAAGGCC TGTTCTGAGG
GTGAGATGAC AGCCACAGAG AGGTCACTGC CACTAGACCA GAAAGTGGAT
GGAGATATAT ATTTGGACTG GTGTTTTTTT CTGTCAG
```

FIG. 19 pSGen 2-91% homology to human HTLV-1 Tax interacting protein

```
ATCGGGCTGC AGATTGGAGA CAAGATCATG CAGGTGAACG GCTGGGACAT
GACCATGGTC ACTCATGACC AGGCTCGGAA GCGGCTCACC AAACGTTCGG
AGGAAGTGGT CCGCCTGCTG GTGACTCGGC AGTCTCTGCA GAAGGCCGTA
CAGCAGTCCA TGCTGTCATA GCTGTAGTCA GCCTAGACTT CTGCCCACTG
ACCTTTTNGG GCACTGAGAA CACATCCACG CTCTGTCTGT ATCTAGTTCT
GGCTTCTGCT GTGTGCTANG CCCCAGCTCT GAGGAGTAAC AGCTGATCCC
AAAGGTCCAA GCCAACCTTC TTACCCCTCA GCCCCANCC CGAT
```

FIG. 20 pSGen 4-Rat proteasome activator

```
TTTTTTTTTT TTTGGGCAAC TATGTATTTA TTGTGTTTGG AAGGCAGAGT
GAGGGAGGAG ACCCCAGCAG GAAGAAGACT GGGTGCAGTC TAGAGTTCCT
AGTCAAGAGT AGGAAGGTTT CTGTTATACC CATCATAGAA CGAGAGAGGG
GGCTCAATAG ATCATCCCCT TTGTCTCTCC ACGGGCTTC TTGAGCTTCT
CAAAGTTCTT CAGGATGATG TCATATAACA CAGCATAAGC GTTACGGATC
TCCATGACCA TCAGCCGGAT CTCCTGGTAT TCCGCCTCGT CCAGCTCGGC
```

FIG. 21 pSGen 10-Rat Ferritin Heavy Chain

```
AANATCTGCT TAAAAGTTCT TTAATTTGTA CCATTTCTTC AAATAAAGAA
TTTTGGTACA AATTAAAGAA CTTTTAAGCA GATGTTTTGG TGCAACTAAT
AGAAAAGATA AAGGCAGCCT GACATGCATG CACTGCCTCA GTGACCAGTA
AAGTCACATG NCCTTGGAC GTCAGCTTAG NTTTATCACN GTGTCCAGG
GGTGCTTGTC AAAGAGATAT TCTGCCATGC CAGATTCAGG GGCTCCATC
TTGCGTAAGT TGGTCACGTG GTCACCCAGT TCTTTAATGG ATTTCACCTG
CTCATTCAGG TAATGCGTCT CAATGAAGTC ACATAAGTGG GGATCATTCT
TGTCAGTAGC CAGTTTGTGA AGTTCCAGTA GTGACTGATT CACACTCTTT
TCCAAGTGCA GTGCACACTC CATTGCATTC AGCCCGCTCT CCCAGTCATC
ACGGTCACNT A
```

FIG. 22 pSGen 12-Novel

```
TGACGTAGGG CCGAGAGCAA CAAGCACAGA ACTCCTTCTC CAGTTTCACC
CTGATGAAGT TGAGGCACTC TTCTGCACTG GGAGGGGCCA GCCTGGGGGC
CAGGCACATT GGACACCACC TTCCCATGGA CTACAGCGTC AATGCCATTG
CCTTCTATTC CTATACCTTC TAGGGCTGC CCCTCTTCCC ATTCAGCCAA
CACTGAGTGT TGGGAGATTT CTCTTTTTTA AAACACATG AGAAATAAA
TGCACTTTAC TCCCTCCCCA AAAAAAAAA
```

FIG. 23
PSGen 13-Novel

```
GTAGGCAATA AAATGTTTTC AGAGGTGCGA AAAAGCTTTT GTTTTCTTAA
ACCATTCTTA GTCTCTGCCA CACTTGACAC TCCGTCAAAG TGAGAAGCGA
ACTAAAGACC AACTGCGGTG GAAAATATTA TGTTTATGTA ATAAAAAAAA
ATCATGTAAC TGCAAAAAAA AAAAAAA
```

FIG. 24
PSGen 23-Novel

```
TGCCGAGCTG AAAACATACA TCCGCACCGG GTTGAGATAG CTGGCCCTCC
GTCCCCGGGC ATACTCTTTG GATAAGAACC CCGGCCTTGT TACCAGGTAC
CGGAGTGAGC TGAAAAATTT ACCGTCGAAA TGGGTGATGT CCTGGAAAAA
ATGGTTCACC AGCTGCCAGG CAGATTCTTT GGGTTCCACA TTTTCCTGCC
CACAGATGTG GCAGAAGCGG TCAAGTAATG CAGCATTACA ATTGAGGCAG
ATCTTTTCTT TTCTTTCCTT GGAGTGGCTC AACCAGCGAT TTTGGTTAAA
AATAATCAAA AAAGCGACGG CAAAACTTTT GTTATATTCC CGCCTGTGGC
ATTTGAACTG TGCCCGGCAA CCGAATAACT TTTAATTTTG AAAATAAAAT
GCATACTAGA TTTTTAGCGG TTGCCTCCTG GCCATTGCTT CAGGCGCCNG
CACAGCGTCA GCCCAGTTTT ACCACNANGA ATATCCTAAG CGTTGAAACA
GGGCACAGCC GAAAAAAACN CTGGCNACAA AAAANATCCG GACATCCTTT
TTCCAATTTT GAAACCGAAN GCNCGCAAAC NAAGGTTCTT CGGGAAAAAA
AATCGCCAAA ATACNCGANA TCAAACTNTC CAA
```

FIG. 25
PSGen 24-Novel

```
TGCCGAGCTG GGGGGAGTTC CAGGAATTTG TGGACTATTT CCAGGAGGAA
TTGAGGAATC TAGAAGTAAT AAGAACTTCA CAAGTAGAAC AACAGAGTTA
ATTGACCTCT ATCCTTAAGA GTTACCAGAG AATTATTAAA AAACTAAAGA
ACAATCAAAG CCTGGTCCTG TGCCACCACC CAAAACATG TATAGCCTAT
GTGCAGCTCG GCA
```

FIG. 26

PSGen 25-Novel

```
CTCANAGGGC NNNTTNGNGG NCNTCATGCN CCAGGNTCCN NCCCCCANAN
GANCNNCCNG GTAAACTACA CNGGAGTACT TAAGTGGACA NNCCACATGC
GANGGNCAAG GGGATCACCN TCNCTCCTNC AGNCTNTNCG TGNCTCTCCT
GTNCNTNCAC TGCCNCANAA NGGANGCNCN NNCTCCTATC TGTNTACAGN
AAACNTNGCN CTNNCTCTAA GCTCNCCAC TNTGTGGAAA GGCNATGTGT
GCGTGCCTCT CCCCTATCAC GGCNGTTGC NAAANGGGGA TGTNCTGCNC
GGCGATGAAG TTNGGTCACT CCATGTTTCC CAGTCCNACC TGTTAGACNA
AGNATTGNAN TGTGATACGA CTCNCTGTAA GGGGANTNGC GGACCCAGTA
TGTTTGGCCC NACNNCCACT TCTTTAAATG GTGGCTAACG GCGCTTCCTA
GNATAAACAC TATTGGTCCC CCCCTCTGCA GNACCCNTTA CTTCCGNANA
AAAATTGTTG TCNTGATCCG CGACAACCAC ACCGTCTGTN GNTTTTAGTT
GCAACNCNNA TCNCTCCAAA AAAGTTTCAG AAATCTTCAT TTTCCCNGGT
TGAGCCCNTG ACAAACCCCT NAGGATTTGT CGAATGTAAA GTCTCCNGAT
CTTCAATAAA NNTCCAAAAG NCTANCGAT
```

FIG. 27

PSGen 26-Novel

```
TCACTGGGCN NNNTGGTNGN CGTCATGCNN NAGGTTCCNN CCCCCNNANG
AACCTCCNGG TAATCTACAC NGGAGTCTTA AGTNGACAAN CCCACACTGC
GANGGTCAAG NGGATCACCA TCNCCNCCTC CCAAGCTTNT NCATTGATGC
TCTCTCTGTT CCGTNCCCTG CCGCTACACA TGGANGCTCT TNCTCCTTNT
CTCNTCTTAC NANNCAAACA TTGCCCTNTC TCATA
```

FIG. 28

PSGen 27-Novel

```
GGGAANGGGA NNAAAAAGGA ATTTTTTNGG GGGGGGNTTN TCTGGGAAAN
TTTTTTTTTT TTTTTGGNAA AAANGGGGGG GGAAANAANC CGNTTTTCCC
NAAAACNGGG GGGAACNGGC CGGGGGGGGA AAAAAAGGG TTACNAAGGG
AAACCTTTNA AANNGGAANG GNTTGCNNC CCTNTGAAA NNTTTGCCCC
CCNNNAGGAA TCCCNGGNNA AACCCAANNC CNNCNCNCG GGGGNCNNTN
CNANGGGACC CCAACNCGGG CCCNAACTNG GGGNAAANAN GGGCAAAACN
GGTNCCCGGG GNAAAANGGT ANCCCCTC
```

FIG. 29

PSGen 28-Novel

```
TGCCGAGCTG GGGGTGAAGC ACCGGAAAAC AACCGATCCA TCTCTTATCA
CAGGGTCTCC AAGATCCCAA ACCCAAAAGC CACATTGTTA ATTAGCCTTT
TTATTGTGTT TTTTTTTTTT TTTTTTTTTT TTTTTTTTTT TTTTTTTTTT
TTTTTTTTTT TTTTTTTTTT TTTTTTTTTT TTTTGGCAGC TCGGCA
```

FIG. 30

PSGen 29-Novel

```
TACGGGCGCT GATTTTTACG AACATTACCT GGCAGGGAAA TTTGATAAGT
ATCCACTGTG GGTGGCGCAC TACCTGGTAA AAGACAAACC CCGTGTGAAA
AGGCCCTGGA CTTTTGGCA ACACAACGAA ACCGGCACG TGAATGGCAT
CCGGTCTTAT GTGGACTTCA ATGTTTTCAA CGGGACAGC ACAGATTTTG
CCGAACTATT AATGAAATAA TGCAGAATTT CGCTTTTCAA ATAAGCCCAT
GGATCCTGAC GTAAATATT TCCTGCTGGT GATCGTGCAG TCCATTTCGA
TGCTCATACT TTGGCTGATG CTCAACATGA CCTTTGGGAT CTATTTTAAT
TTTGCTTTCC CCGACAATGG TTTGACGCTT GGCAACATCA TTTATTACCT
CTTCCTGCTG GGCAGCTCGG CA
```

FIG. 31

PEGen 32-Novel

```
TNCATANGCC CTGAGGTGGG GACGAAGCCC GAGTCCGTCC TGACATGTTT
CCAGTGGAAA AGATTTGTT NTGAGCGTTN CTTTCTNNTT TNTTTTNNNT
TGNTTGTTNN ATGTTTTTGT TGTTGTTTTN TTNAAACTGT NTGTTGNCAN
TTCAACATNA ANGGNAGGNA ANTNTGTGNC TNCNTTGCAN TGTNNCATGN
TNCCCANANC CCAAAAAAAA AAAAAAAAA AAAAGAGTA CAAATATCAC
AAAATTTGAC ATTTTGTAA TAATACTTTG GTTGTTGTTT GGTGACGGCG
ATTG
```

FIG. 35A

PSGen 12 cDNA Sequence

```
GCGGTGGTGA CGGTAGTATG GCCGCACTTT ATGGTGGCGT GGAAGGGGGA
GGCACACGGT CCAAAGTCCT TTTACTTTCT GAGGATGGGC AGATCCTGGC
AGAAGCAGAT GGACTGAGCA CAAATCACTG GCTGATTGGC ACAGGTACCT
GTGTGGAGAG GATCAATGAG ATGGTGGACA GGGCTAAACG AAGGCTGGA
GTGGATCCTC TGGTACCCCT TCGAAGCCTG GCTTGTCCC TGAGTGGTGG
GGAGCAGGAG GATGCAGTGA GGCTCCTGAT GGAGGAGTTG AGGGACCGAT
TTCCCTACCT GAGTGAAAGT TACTTCATCA CCACTGATGC AGCAGGTTCC
ATCGCCACAG CTACACCGGA TGGTGGGATT GTGCTCATCT CTGGAACAGG
CTCCAACTGT AGGCTTATCA ACCCTGATGG CTCTGAGAGT GGCTGTGGTG
GCTGGGGCCA CATGATGGGA GACGAGGGAT CAGCCTACTG GATTGCACAC
CAAGCTGTGA AAATTGTGTT TGACTCCATT GACAACCTGG AAGCAGCTCC
TCATGATATT GGCCATGTCA AGCAGGCCAT GTTCAACTAC TTCCAGGTGC
CAGATCGGCT AGGAATCCTC ACTCACTTGT ATAGGGACTT TGATAAGTCC
AAGTTTGCTG GATTTTGTCA GAAAATTGCA GAAGGTGCAC AGCAGGGAGA
CCCTCTTTCC AGGTTCATCT TCAGAAAGGC TGGGGAGATG CTGGGCAGAC
ACGTTGTGGC AGTATTGCCA GAGATTGACC CAGTTTTGTT CCAAGGGGAG
CTTGGCCTCC CCATTCTGTG TGTGGGCTCA GTGTGGAAGA GCTGGGAGCT
ACTGAAGGAA GGCTTTCTCC TGGCACTGAC GCAGGGCCGA GAGCAACAGG
CACAGAACTC CTTCTCCAGT TTCACCCTGA TGAAGTTGAG GCACTCTTCT
GCACTGGGAG GGGCCAGCCT GGGGGCCAGG CACATTGGAC ACCACCTTCC
CATGGACTAC AGCGTCAATG CCATTGCCTT CTATTCCTAT ACCTTCTAGG
GGCTGCCCCT CTTCCCATTC AGCCAACACT GAGTGTTGGG AGATTTCTCT
TTTTTAAAAA CACATGAGAA AATAAATGCA CTTTACTCCC TCCCCAAAAA
AAAAAAAAAA AAAAAAAAA AAAA
```

PSGen 12 Protein Sequence

```
GGDGSMAALY GGVEGGGTRS KVLLLSEDGQ ILAEADGLST NHWLIGTGTC
VERINEMVDR AKRKAGVDPL VPLRSLGLSL SGGEQEDAVR LLMEELRDRF
PYLSESYFIT TDAAGSIATA TPDGGIVLIS GTGSNCRLIN PDGSESGCGG
WGHMMGDEGS AYWIAHQAVK IVFDSIDNLE AAPHDIGHVK QAMFNYFQVP
DRLGILTHLY RDFDKSKFAG FCQKIAEGAQ QGDPLSRFIF RKAGEMLGRH
VVAVLPEIDP VLFQGELGLP ILCVGSVWKS WELLKEGFLL ALTQGREQQA
QNSFSSFTLM KLRHSSALGG ASLGARHIGH HLPMDYSVNA IAFYSYTF·
```

FIG. 35B

PSGen 13 cDNA Sequence

```
GGCACGAGCT CTCCTCGTCC CCTCCCTTCT CCACTGCAGC CTTTCTCTTA
GCCCGAACCA CTTCCTTCTT CTGCTTGTTC CTCCCTAGGG CGCGGAAGCT
GAGTGCAGGG TTCAGACCCA CGCGGCGAGC AGCTCTTCAG TGAAGAAGGA
AGCAATCGGA GGGTCAGCAA TGAACGTGGA GCATGAGGTT AACCTCCTGG
TGGAGGAAAT TCATCGTCTG GGTTCCAAAA ATGCCGATGG GAAACTGAGT
GTGAAGTTTG GGTCCTCTT CCAAGACGAC AGATGTGCCA ATCTCTTTGA
AACCGTTGGT GGGAACTCTG AAAGCCCGCA AAACGAAGGA AGATTGTTAC
GTACGCAGAA GAGCTGCTTT TGCAAGGTGT TCATGATGAT GTTGACATTG
TATTGCTGCA AGATTAATGT GGTTTGCAGA TCTGGGGGTA TCTGGTAAAC
TGGAATAATT AAGTTAAAGG ACAAACATGA AGTTCCTTAT GTATTTTTAT
AGACCTTTGT AAACAAAAGG GGACTTGTTG AGAAGTCCTG TTTTTATACC
TTGGAGCAAA ACATTACAAT GTAAAAATAA ACAAACCTG TTATTTTTTT
TTTCTTAAGA AGGTAATCGG GAGACGTAGG CAATAAAATG TTTTCAGAGG
TGCGAAAAAG CTTTTGTTTT CTTAAACCAT TCTTAGTCTC TGCCACACTT
GACACTCCGT CAAAGTGAGA AGCGAACTAA AGACCAACTG CGGTGGAAAA
TATTATGTTT ATGTAATAAA AAAAAATCAT GTAAAAAAAA AAAAAAAAA
```

PSGen 13 Protein Sequence

```
MNVEHEVNLL VEEIHRLGSK NADGKLSVKF GVLFQDDRCA NLFETVGGNS
ESPQNEGRLL RTQKSCFCKV FMMMLTLYCC KINVVCRSGG IW·
```

FIG. 35C

PEGen 28 cDNA Sequence

```
GTGTGGTGTG TCTCTCAGAC GTCCGTGACA CTTTGATCCT GCCCTGCCGG
CACCTGTGCC TCTGCAACAC CTGTGCAGAC ACCCTGCGCT ACCAGGCCAA
CAACTGCCCC ATCTGCCGGC TGCCCTTCCG GGCACTGCTT CAGATCCGAG
CCATGAGGAA AAAATTGGGC CCTCTGTCTC CAAGCAGCTT TAACCCCATC
ATCTCTTCCC AGACTTCGGA CTCTGAGGAA CATTCATCCT CAGAGAACAT
CCCTGCGGGC TATGAAGTGG TGTCTCTCCT GGAGGCCCTC AATGGGCCCC
TCACCTCATC CCCAGCGGTG CCTCCCCTTC ACGTTCTTGG AGATGGCCAC
CTCTCAGGAA TGCTGCCGTC CTATGGCAGT GATGGCCACC TGCCCCCTGT
TAGGACACTG TCCCCCCTTG ACCACCTGTC TGATTGCAAC AGCCAAGGGC
TCAAACTCAA CAAGTCTCTC TCCAAGTCCA TTTCCCAGAA TTCTTCTGTG
CTTCACGAAG AGGAAGATGA GCGCTCTTGC AGTGAGTCAG ACACTCAGCT
CTCTCAGAGG CTGTCAGCCC AGCATCCTGA AGGGACCT GATGTGACTC
CAGAGAGTGA GAACCTCACG CTGTCCTCCT CAGGGGCTGT TGACCAGTCA
TNTTGCACAG GGACTCCGCT CTCTTCCACC ATCTCCTCCC CAGAAGACCC
AGCCAGCAGC AGCCTGGCCC AGTCAGTCAT GTCCATGGCC TCCTCCCAGA
TCAGCACTGA CACCGTGTCC TCCATGTCTG GCTCCTACAT TGCACCTGGC
ACAGAAGAAG AAGGAGAGGC CCCACCTTCC CCCGAGCTG CTAGCAGGGC
CCCTTCAGAA GAGGAGGAGA CCCCAGCAGA GTCCCCAGAC AGCAATTTTG
CTGGCCTTCC AGCTGGAGAG CAGGATGCAG AGGGAAATGA TATCATGGAG
GAAGAGGACA GATCCCCTGT GCAAGAAGAT GGCCAGAGGA CATGCGCATT
TCTAGGCATG GAGTGTGACA ATAACAATGA CTTTGACGTC GCGAGCGTGA
AAGCACTGGA CAATAAGCTG TGCTCTGAGG TCTGCTTACC CGGTACCTGG
CAACATGATG CCGCCATTAT CAACCGTCAC AATACCCAGC GCCGGCGACT
ATCACCCAGC AGCCTGGAGG ACCCTGAGGA GGACAGGCCT TGCGTATGGG
ATCCTTTGGC TGTCTGAGGG CACTGGCACC TGTACCTGGG CTTCCCCTCC
TGTCCGCCTT CCATCTGTCC TCACTGGACC ACAGGCCTTC TGGGCATCTT
CAACAAGACA CGTGGACTTT CTACTCTCAT GAAGGGAGGA CAGTGCAACC
CTCCACCAAC TTCATCTCCT GTAACCATGA TTCTTACCCT CTCAGAAAGT
ACCAGAAGCC TTCCTCCTGT GGGCTGATGT GTGCCAGCCA AACCCAGTGG
GTCAGCTGAG CTGAGGGTCA GGGCTGGTTG TTTCTGTAGC CTTTTCTCTT
CCAAATGGAG ACCAACGAGA AANAAAAAAA AAAAAAAA
```

PEGen 28 Protein Sequence

```
VVCLSDVRDT LILPCRHLCL CNTCADTLRY QANNCPICRL PFRALLQIRA
MRKKLGPLSP SSFNPIISSQ TSDSEEHSSS ENIPAGYEVV SLLEALNGPL
TSSPAVPPLH VLGDGHLSGM LPSYGSDGHL PPVRTLSPLD HLSDCNSQGL
KLNKSLSKSI SQNSSVLHEE EDERSCSESD TQLSQRLSAQ HPEEGPDVTP
ESENLTLSSS GAVDQSXCTG TPLSSTISSP EDPASSSLAQ SVMSMASSQI
STDTVSSMSG SYIAPGTEEE GEAPPSPRAA SRAPSEEEET PAESPDSNFA
GLPAGEQDAE GNDIMEEEDR SPVQEDGQRT CAFLGMECDN NNDFDVASVK
ALDNKLCSEV CLPGTWQHDA AIINRHNTQR RRLSPSSLED PEEDRPCVWD
PLAV·
```

FIG. 35D

PEGen 32 cDNA Sequence

```
GGCACGAGGC GCCGCCTTCC TGCTCGCGCC CTATCGCCGC CTTCCTGCTC
GCGCCCTATC GCCGCCTCCG AGTCTTCCTG CGCCCCGGGC TTCCGCCGCT
TCATTGATTT CCGTTTCTCG CCGCTGCAGC CTCCTGACAC GGTGATCCGG
GCGGGCCCCG CAGGAATTTT ATCCCCTCAC CGGCCTCACA CTAGTGTCGC
ATGTCCACTA TCCAGAACCT CCAATCTTTC GACCCCTTTG CTGATGCAAC
TAAGGGCGAC GACTTACTCC CGGCAGGGAC TGAGGACTAC ATTCATATAA
GAATCCAGCA GCGGAACGGC AGGAAGACGC TGACCACTGT GCAGGGCATT
GCGGACGATT ATGACAAAAA GAAACTTGTG AAAGCTTTCA AAAAGAAATT
CGCCTGTAAT GGGACTGTGA TTGAACACCC TGAGTACGGA GAGGTCATTC
AGCTTCAAGG CGACCAAAGG AAGAACATTT GCCAGTTTCT TTTGGAGGTT
GGCATCGTCA AGGAGGAGCA GCTGAAGGTT CACGGATTCT AAGATGAACC
CGAACATGTG GCGAGTTTCT TAAATGGTTT TGTTGTCTAA CTCAGTTTGG
CTGCCTCGGG AGATGATTCT TTACAGTAAA CGACAGACTT TGCGTTTATT
AAATCATTCA GACTTCCACT CACGCCTGCA TGGCTACAGA AAACATGGGG
TATGTAGGCT CCTAAGTCAC AAGGAAATCG CCGTGAGGTG GGACGAAGC
CCGAGTCCGT CCTGACATGT TTCCAGTGGA AAAGATTTTG TTCTGAGCGT
TCATTTCTAG TTTATTTTCA CTTGATTGTT AAATGTTTTT GTTGTTGTTT
TATTAAACCA TGTATGTTGC AGCTTAACAA TAAAGGAGGA AAGTCTGTGC
GTCAAAAAAA AAAAAAAAA AA
```

PEGen 32 Protein Sequence

```
MSTIQNLQSF DPFADATKGD DLLPAGTEDY IHIRIQQRNG RKTLTTVQGI
ADDYDKKKLV KAFKKKFACN GTVIEHPEYG EVIQLQGDQR KNICQFLLEV
GIVKEEQLKV HGF·
```

FIG. 35E

PEGen 42 cDNA Sequence

```
GGCGTTGCGA CGTGGACATG TCGGCGTCGT TGGTCCGCGC CACCGTGCGG
GCCGTGAGCA AGAGAAAACT GCAACCCACG CGGGCGGCGC TCACGCTGAC
CCCCTCTGCT GTGAACAAGA TAAAACAACT TCTTAAAGAC AAGCCTGAGC
ATGTGGGTCT GAAAGTGGGT GTGCGGACCA GGGGCTGTAA CGGCCTCTCT
TACAGCCTGG AGTATACAAA GACAAAGGA GATGCTGATG AAGAAGTTAT
TCAAGACGGA GTCCGAGTGT TCATCGAGAA GAAAGCCCAG CTAACCCTGT
TAGGCACAGA GATGGACTAT GTGGAAGACA AACTGTCCAG TGAGTTTGTG
TTCAACAACC CCAACATCAA GGGAACCTGT GGCTGCGGTG AAAGCTTTAA
CGTCTGAAAG CTGAGGACTG CAAACTCCAG GAGAGCTGGG TCTGCCTTGG
AGCACACCGA GAAATCATG TGATGTCCCG TGTCGGAAGT TAGTGTGTGG
CTGCCTCGTG GTTGAGAATA AAGTGAAGCA TTGAAAATCA AGCCAGCGTG
TTAGAGTTCC AAAAACATGG TGTCTGTTCT CTGTAAGACA CAAATGGAGA
GAACATGGTG TCTGTTCTCT GGAGGACACA AACTGAGAAA CTGTTGAGTC
CTCTGTCCTG TACAGAAAAC TCCTACCCTG CCCTTACGCT GTAGCCTGCT
CTGTGCTAGA ACCAGCTTCG TGACCATTGC TTTGCTGGGA ATTGAGGAAT
GGGATAACGG TGTGCACCT GGGTCACAGA ATGGCTTGAG ACTGTCTCCT
GGCCCTGTCT CACCTCAGGC AGGGCAGCTG TGGGAGCAGC AGCTGTGGGA
GCGGTGAGGG GACCTGGTTT CCCTCACCTG TGGCGTGGCC CGTTGCATCT
TTACCACGTG CCTGTTGTCA GATACCTCAT TTGCCAGCCT CCAGCAAGCT
CAGCTATGAG TGCCAGTCTC AGGAGGTAGG GATCACGGGC CTGGTGTCAG
TCTGTCCTCT GGGGCGTGCT TCATGCGGTT TGCTTAGACC TTTCAGTTAG
AAGCGCTTGT GATGAGCAGC CAGGTAGACC TGCTGAGAGC GTGGTTCTCA
GAGCTTCTGC CCAGCCCTCC TCACAGGTCA CAGCAGACAG TGCTGTCTGA
GACACTCGGT GAGGAGACAT CCTGCCTGGC CAGTGCTCTT ACCAGTTTAG
AGACTGCATT AGTTTCTCT TGAATGGAAG CCTTGTGTAA ACCCTTTTGT
CTGAATGGCC ATCCTGTTTA GAGCTTTGAA CCAGTAGTGT CTTCCTTCAG
AAGATCTGCA GCAGAGGGGT CCCTCTCAGC ACGGCACCTG GGGGGCAGAA
CATGCACACA CTTACAGTTG CCAGGGTGCA GATGCTCCCT GCTTCCCAGA
GGAAGCTTCT AAGTTTCTTT AATGTGGTCA TCACCAGTTT TTTGAGCCAT
GGTTTGCTG TATACTACAG GCCAGCCTTG AACCCACAAC AATCCTCCTG
CTTCCACGTT CAGAGGCATG TGCTACCACA CCTGACCTGG ATCCCAAGTT
TCTCTTTAAG TGGTCTTGAT GGACTTGGGT CGGACATCTT AGTGACCTGT
GAATTCTTCT GTGGAGGCTG AGTCTACGT AGCCGAGTTT AATATCTGTG
CTATTTACTA AAGTATCTGC CACCAAATTG TACCAACTCA TAGTTTTATA
TGAATGTTGA TGAGTCTGTA TCATAAATAG AATTGTTGAT ACATCCTTAA
TTTGTGCAAT ATTGTATGAA GAAGATTGTT ATCAATTAAA ACCACGCCTC
TTTATGATCC TAAAAAAAAA AAAAAAAAA AAAAAAAAA AAAAAAAAA
AAAAAAA
```

PEGen 42 Protein Sequence

```
RCDVDMSASL VRATVRAVSK RKLQPTRAAL TLTPSAVNKI KQLLKDKPEH
VGLKVGVRTR GCNGLSYSLE YTKTKGDADE EVIQDGVRVF IEKKAQLTLL
GTEMDYVEDK LSSEFVFNNP NIKGTCGCGE SFNV·
```

FIG. 35F

PEGen 45 cDNA Sequence

```
ACGAGCTGAA GGTCACTTCG CGCACGGGTT GGACCTGGGG CAGGTTGGAG
GAGTAGGAGT ATGTCATTGG GCGCGAAGAC GGGGTCTGGG GCAAAAAAGA
AGGGAGGCTG GAGAAATCTG GACCCGAGAC GTAGTAAGTA CAACTTGGCA
AATACATGTT AGAGGAGCAG GGACCACGCT CATCAAAATC CATCATTGGG
CTACCTTGGG CTCTCCGCAG TAGCCGAGCT TAACATGATT CTCCACTGCA
GCTGCCTCTT TGAAGCGGAT CCGTGAAGTA GAAATTTGGA GACGTAAGCT
GACGTGGAAA TCTATCCCCA TCCTTAGCAG GGAGGTGCTG GTCATGTGAC
CCGATGTTGA AATTGACAAG CCGCGAGCTA GTCCCGGCTT TTTTTTTTA
ACCCCCCTCC CTTTCCTTTT TTCCCCCTCC CCTCCCTCCT CGGCTTCCTT
TCTTTGTAGC CACCTCAGGG GAAGCAACAG ATCGTCACTC GGTGTTCTCA
CCGAAAGCAC GTAATCGCCG GTGTAACTCA TGTTGGCTGG GGGGCCTCCC
CGCTCGCAGA AAGGCTGGGG TGCGCCCCA AGCAGCTTTC CTTTGCTCAG
CTGCATGGTC CTGGTCCACG AGCGCTCTGA GGGCGGCAAG AGAGCGCAAC
TCCTGACGCC TCCCCCCACT CCCCGGTGGG TGAGGGATGC TCTGGGATGG
GGGTGGCCAG GTGAACGCCC GGAATTGTGT AGCTTCAGGT TCCGGAGTCT
GTTGTCCGAA GGCTTACGTT CAGCACCTTC TTCGCAGTCC CCCTCCCACA
GACTTGCTCT GGAAAGCACC TCAGTCTCAG AATCTGGCTG GACCCCATTT
GGGGCCAGGC TTCGCAGCCA CGATGTGCCG GGCTTCGTGG CTTGTCCGAT
TTGCACGGTG ACTTGATTAC ACGCTCTCAT TCATGGTCAC TTCCGAAGCG
CTTTAGTGCC TTCCGTCCCC AAACCGCCAA CAGGCAAAGC GGCTTTCCTC
CGCGGTTTGT CAATAATCCG CGCTGTCCGG AAGGGCTTCG CCTTACCCGG
GTTCCACCTT CCCTGTATCT TTCTGCTTAC TTCCTCATCC CACACTCTGT
CCTTGGAGGA ACCCCTTCTC CTCGCTGCCT GTAGGGGTTC GGAGTGACTC
CACAGAGCCA GAGGCGCTTC TGCTCACCGG TCCGCAAGCT GCCTGGTCTG
CTGAAGCTGA CGAATCGGGA AACCATGCAA TTGAGGCGAA CCTTGGGCTG
CTTTAGAGGC GCTGAGGAGC CTTCTCCTGG GAGGCCCAAG GTCGATTTCA
GCCCACCAGG ATCTGGGGAA GACCCAACTA GGGGTAAGAG CACACCGGAA
GGCCAAGTCC GAGTTCCAGT CCTAGAAGAG GCGGCTGCGG GCAAGGTTAT
GACATTGGCC CTGGACACTG GTTTCCAGG AGCTATTCTT TCTCAAGAAC
TCCACAGCAC GGGGCTGTCT CCAGAAAATA CTCTTAACG TTTATTTCCT
TTAATCGTCA ACCCGCAGCC CTACGGCGGT TAATGCGAGA GGCCAAAAAT
GTTTGGAGGA AGAAAAACAA AGGCAGGAAG TGGCCGCGGC CTGACGGTGC
GTGTGTGTCT GTAAAGAAGG GAGGGAGCCG GTTCAATCTC TTCTTTTTTT
CCCCGAATTT CAAGGTTTAG GCAGACCCC GTAGGGCCTG GCCGAGGCTC
ACCCGGCGGA GCATTTGGAG GTGGCCAATG AGTAAGGCTC GTCGGGCTGA
AAGGCTAAGA AGGAGATTTG ATCGGCAGAA CAAACCAAGC CTTTTTGGAG
GTTTCTTCTG ATTTGGTCCT AAAGGGTATA TGCTAGTGTC CACAGCGGCT
CCTGTGGCTG CTGTTTTCCT CCTGTCGGAC TAAATGTACC AAGAAGGGAG
AGAGATTGAG GCACCTTGCG CGCTCCTCTC TCCTTCCGAG GTAGAATATC
AGAATAAAGT GTATTCAGGT GCCAA
```

FIG. 35G-1

PEGen 50 cDNA Sequence

A:

```
ATCGGCTGT ACTAACAGAT TGTTTGTAAA CAGTGACACA GTGATAACTT
CCGTGTTACT TCTTAACTTT ATGTTTCTGC TTTCAGATCT CCCTCCCCTT
CCAGAGGAAG TTAGCGATGC CATAGCTTTA ATGTCTGTTT TAGCTGCAAA
ACTCATTGTT CACTTTCTGT TAGAAAATCT AAAGCAGGTG GTATGCAATT
TCTCTTGATT TGGAATTCTT TAAAGGCAAG TAAATTTGGA ACTCCTGTGT
TGGGGGGTTA ACGGAGGTAG GAACCCAATG GTGTGTCCCT AGGTCGTCCC
CGTTCTCGGA TAGCACAGTC TGCATAGCCA TAGCTCTCAA TTATGTCACT
ACCCTAATCA TCGCAGCCCG GTTCTCACGG ACTCTTTGAA GTCCCAAAAT
GACTTTTGTT TGATCCTGAT TTGGATTTTC AATGGAAAGT AAAAGCTTGG
GGTGAGGAAG CAGCAGCTAA AGCAGGGAGT TGAGCCAGTG AATTGCTGAC
GGAAAGGATT CTGGTCTTGG AGGAGGGGGA CCTGAAGCAG AAGGAAAAGG
GATCCTTCGC TTAAGTTCTT AGGAAAAATC TTGACTCAGA ATCCCAAGAT
TTTTCCCTTC ATCCCAGCCG GGTAAATATT TGGTTTTGTC TTTTAAGTAT
AGCATGAAGC CCGTGGATGA GAGCCATGTG TTGTAGGATT CTCTTCCCTA
TTGGCTCTGA GCTTGTGTCA CCGTATCAGT TTGCTCCCTA CAAAGGGACC
TAGTTTGGAA AGGATTGGAA GGGCAACTGT TCAGCGGCAA TGGAACACCC
AAACGTGGAC TGGGACAACG GGATTCTGAT AAAGGGAAAT TTCTGGTCTG
GTCCTGGCTG TGTCATAGCT CTTTATGTGT GCATGGAGAG CTCTTGATCC
AAGTAGAATA TGTAACAATA CAGACCAGGA TCTTCCAGTC AGTACTGCTG
GGTGGAAGTG GGCGGGTGAT GGTAGTTGCT AGAAGAATCA TTAAGACAGC
ATCTGCGGTG AATGCGTCCC AAAGCCTCGC GGCATCAGTT TCATCTCTAA
ACCATTAGCT TACAGTTGAT TCCGTTTCCT GGGACAGAGA AACATCCCCA
CGCGAAGTGA CTGTGTTGTG TATTCATAGC ACTGCAAATA AATTCACGCG
CCATGATGAA ACCTTGCAAA TACGCTTTGA CCAAAAAAAA AAAAAA
```

```
GGGTGTGGGG CAGCTGGGTG GGAGCAGCGT GCAGGCTACC AGCACCAAGT
GGTGTGCCTC TCCGGGGGTG TGTGCAGAAG GCTCCTGGGG AAAACTGCAC
AGGTACCACC CCTAGACAGA AATCGAAAAC CCACTTCTCT CGGTGCCCCA
AGCAATACAA GCATTACTGC ATCCATGGGA GATGCCGCTT CGTGATGGAC
GAACAAACTC CCTCCTGCAT CTGTGAGATA GGCTACTTTG GGGCCCGGTG
TGAGCAGGTG GACCTGTTTT ATCTCCAGCA GGACAGGGGG CAGATCCTGG
TGGTCTGCTT GATAGGCGTC ATGGTGCTGT TCATCATTTT AGTCATTGGC
GTCTTGCACC TGCTGTCATC CTCTTCGGAA ACATCGCAAA AAGAAGAAGG
AAGAGAAAAT GGAAACTTTG AGTAAAGATA AAACTCCCAT AAGTGAAGAT
ATTCAAGAGA CCAATATTGC TTAACTTAAT GATTATAAAG TTACCACAAG
CTGATGGCGA GCTCCAAAAG ACCTGACTCA TTTGCAGATG GACAGGACAT
GTCTCAGGAA AACAGCTTGC AGAAATGAAT GTTAAATAT TGTATTTGCT
TTTTCATTTT ATTTGTAACT GTGTTGTT ATTGTTTTA ATAATGATAT
TTTTGTTACA GTCTGATAGC TGAGAAAAAA ATGACCTGGT TAGGTGACGA
CAATAAGGGA CATTGAATAT AAACTTTGTT GCTAGGATTA TTAAACAAAC
AAAATTTGGA AAGAAGTTAG ATTTTAAGAA CTGAGTCATG GTCAGGCAGC
GATGGCACAC ATCTTTAATC CCAGCACTTG GGAGCAGAGG CAGGTAGATC
TCTGGGAGTT TGAGGTCAGC CTGGTCTACA AAGCAAGATC CAGGGTAGCC
AAGGTTATAT AGAGAAACCC TGTCTCACAA AACCAAACCA ACCAATCAAC
CAAACAGCAA AACACCTGAG TCGATAAAAG GGCTCCCAG GTTTATACAC
TTACCGTATG CTAAGAGCTT GAAATATATT GTTTCGTTTT ATCGTTCAGT
AGTCTGTGAG ATTGCATTTT TTCTCATTCC TATATATAAA AAAGTTAAAT
GATTTCCCTT AGATGTAGAG ATAGAGGAAG TTAGCGATGC CATAGCTTT
```

FIG. 36

PSGen 27-Novel

```
NTCNNCTTNN CNNNGGCTGA TATCNGGCNC TTCNTCCNCG ATCNCAGATA
CNNGCNCACC GGNNNTNTCN GNGGTNATCN TCCNCCATCT CTCNTCCCCG
ACNTGCACTC CGGGTNTNNT ACACNGGACA CTGTATCNNA CAGNAAACCT
NCCCNGGCCC CAGGGATCAC CATNCCTCGN CCCNGCNTGT NTATAANATC
AGGNNNTACA TCNANGAACN NACTATCACN GNTCTCTNTT NNCTCAGTGT
NCACCTTCCA CTNCNGAANC TNNTCGCTNC NCCNCNGTTG GGAAAGGCGA
NCNGTNCCGG CNACATGCCG TTTNCGNCNT CTGNNCACNT GGGGATCTNC
TNCAANGNAA TCAATTNGNG TAACCCACGG TTTNCNCAAT CACTACTTCT
CANNCNANGG CCNTTGAANT GTTATCCCAC CACCANGGGG CNANTCGGGA
CCTNACAATT CATCCTCAGC CGGCCCCAGN CTTAAAAAAT TCAAAGGNCN
CTTGCCCGCN TTNTTNCCTT AGCCCGCCNC CNGACAACAN CCNANNAACA
ACCCCNNTC TTANGTTGCN NANCCCACAG GANNTTGNNA TACCGGGTTT
CCCCNGAAAC TNCTCAANGC CNCCGTTCCA ACCCCGTTA CGAAACCGTN
CCCNTTTCCT TCCGAGNTTG CCTATTAANN CCCCCNAAGT TCTNCTTCGT
TNGNTTCCTC CGAAANG
```

RECIPROCAL SUBTRACTION DIFFERENTIAL DISPLAY

This application is a continuation of PCT International Application No. PCT/US99/04323, filed Feb. 26, 1999, designating the United States of America, which is claiming the priority of U.S. Ser. No. 09/032,684, filed Feb. 27, 1998, the contents of which are hereby incorporated by reference into the present application.

Throughout this application, various references are referred to within parentheses. Disclosures of these publications in their entireties are hereby incorporated by reference into this application to more fully describe the state of the art to which this invention pertains.

BACKGROUND OF THE INVENTION

Changes in gene expression are important determinants of normal cellular physiology, including cell cycle regulation, differentiation and development, and they directly contribute to abnormal cellular physiology, including developmental anomalies, aberrant programs of differentiation and cancer (1–4). In these contexts, the identification, cloning and characterization of differentially expressed genes will provide relevant and important insights into the molecular determinants of processes such as growth, development, aging, differentiation and cancer. A number of procedures can be used to identify and clone differentially expressed genes. These include, subtractive hybridization (5–10), differential RNA display (DDRT-PCR) (3,4, 11,12), RNA fingerprinting by arbitrarily primed PCR (RAP-PCR) (13, 14), representational difference analysis (RDA) (15), serial analysis of gene expression (SAGE) (16,17), electronic subtraction (18,19) and combinatorial gene matrix analyses (20).

Since first introduced by Liang and Pardee (11), DDRT-PCR has gained wide popularity in analyzing and cloning differentially expressed genes. In DDRT-PCR, total RNAs or mRNAs from two or more cell types (or cells grown under different conditions, cells representing different stages of development, cells treated with agents modifying cellular physiology, etc.) are reverse-transcribed with two-base-pair anchored oligo dT primers, which divide mRNA populations into 12 cDNA subgroups. Then, each cDNA subgroup is amplified by PCR with one of 20 arbitrary 10-mer 5' primers and a 3' anchored primer and the PCR-amplified cDNA fragments are resolved in DNA sequencing gels. The combinations of primers are designed not only to yield a detectable size and number of bands, but also to display nearly the complete repertoire of mRNA species.

DDRT-PCR is a powerful methodology in which a vast number of mRNA species (>20,000, if no redundancy occurs) can be analyzed with only a small quantity of RNA (about 5 µg) (11). DDRT-PCR is often the method of choice when the RNA source is limiting, such as tissue biopsies. A direct advantage of DDRT-PCR is the ability to identify and isolate both up- and down-regulated differentially expressed genes in the same reaction. Furthermore, the DDRT-PCR technique permits the display of multiple samples in the same gel, which is useful in defining specific diagnostic alterations in RNA species and for temporally analyzing gene expression changes. However, the DDRT-PCR technique is not problem free. Difficulties encountered when using standard DDRT-PCR include, a high incidence of false positives and redundant gene identification, poor reproducibility, biased gene display and lack of functional information about the cloned cDNA. Furthermore, poor separation can mask differentially expressed genes of low abundance under the intense signals generated by highly expressed genes. The generation of false positives and redundancy can be highly problematic, resulting in an inordinate expenditure of resources to confirm appropriate differential expression and uniqueness of the isolated cDNAs. The cDNAs must be isolated from the gels in pure form (contamination of bands with multiple sequences complicates clone identification), reamplified, placed in an appropriate cloning vector, analyzed for authentic differential expression and finally sequenced. These limitations of the standard DDRT-PCR approaches emphasize the need for improvements in this procedure to more efficiently and selectively identify differentially expressed genes.

A number of modifications and improvements of the DDRT-PCR approach have been described (21–23). Single anchor or degenerate two-base anchor oligo dT primers can be used to streamline the massive numbers of reverse transcription and PCR reactions required for validation of cDNAs as well as to reduce false positives (24,25). Reproducibility can be improved by lengthening the arbitrary 5' primers to accommodate a convenient restriction site followed by two cycles of PCR with successive low- and high-stringency annealing temperatures (25,26). DDRT-PCR with inosine-containing 5' arbitrary primers can also increase reproducibility of this approach (27). However, since these modifications have only been analyzed using a subset of primers, further studies are necessary to validate these modifications of DDRT-PCR with additional primers and in several model systems.

In addition to genomic DNA contamination, mispriming, PCR artifacts, the high incidence of false positives and redundancy is also ascribed to poor separation between bands and the complexity of the templates amplified (28). Furthermore, poor separation can mask differentially expressed genes of low abundance under the intense signals generated by highly expressed genes. By enriching for unique cDNAs and removing common ones, it should in principle be possible to enrich for low abundant gene products and significantly decrease the complexity of amplified sequences. In addition, the sequence bias of DDRT-PCR should also be reduced by decreasing template complexity. These assumptions serve as the basis for the development of reciprocal subtraction differential RNA display (RSDD).

Subtractive hybridization, in which hybridization between tester and driver is followed by selective removal of common gene products, enriches for unique gene products in the tester cDNA population and reduces the abundance of common cDNAs (9). A subtracted cDNA library can be analyzed to identify and clone differentially expressed genes by randomly picking colonies or by differential screening (29–31). Although subtractive hybridization has been successfully used to clone a number of differentially expressed genes (5–7,10), this approach is both labor-intensive and does not result in isolation of the full spectrum of genes displaying altered expression (9,18).

In principle, DDRT-PCR performed with subtracted RNA or cDNA samples represents a powerful strategy to clone up and down-regulated gene products. This approach should result in the enrichment of unique sequences and a reduction or elimination of common sequences. This scheme should also result in a consistent reduction in band complexity on a display gel, thereby permitting a clearer separation of cDNAs resulting in fewer false positive reactions. Additionally, it should be possible to use fewer primer sets for reverse transcription and PCR reactions to analyze the complete spectrum of differentially expressed genes. Of particular importance for gene identification and isolation, rare gene products that are masked by strong common gene products should be displayed by using subtraction hybridization in combination with DDRT-PCR. In addition, the DDRT-PCR approach with subtractive libraries could also prove valuable for efficiently screening subtracted cDNA libraries for differentially expressed genes. However, even though subtraction hybridization plus DDRT-PCR appears attractive for the reasons indicated above, a previous attempt to use this approach has proven of only marginal success in consistently reducing the complexity of the signals generated, compared with the standard DDRT-PCR scheme (32).

We presently describe a reciprocal subtraction differential RNA display (RSDD) approach that efficiently and consistently reduces the complexity of DDRT-PCR and results in the identification and cloning of genes displaying anticipated differential expression.

SUMMARY OF THE INVENTION

This invention provides a method for identifying differentially expressed nucleic acids between two samples, comprising: (a) selecting a first and second nucleic acid sample, wherein the nucleic acid samples contain a repertoire of nucleic acids; (b) performing reciprocal subtraction between the nucleic acid samples to produce two subtracted nucleic acid samples; (c) amplifying the two subtracted nucleic acid samples; and (d) comparing the two subtracted nucleic acid samples to identify differentially expressed nucleic acids.

This invention also provides a method for identifying differentially expressed nucleic acids between two samples, comprising: (a) selecting a first and second nucleic acid sample, wherein the nucleic acid samples contain a repertoire of nucleic acids; (b) amplifying the two nucleic acid samples; (c) performing reciprocal subtraction between the amplified nucleic acid samples to produce two subtracted nucleic acid samples; and (d) comparing the two subtracted nucleic acid samples to identify differentially expressed nucleic acids.

This invention further provides the above-described methods, wherein the first and second nucleic acid samples are obtained from cells in different developmental stages.

This invention further provides the above-described methods, wherein the first and second nucleic acid samples are obtained from cells from different tissue types.

Also, this invention provides the above-described methods, wherein the 3' primer used in the PCR amplification is an oligo dT 3' primer.

In addition, this invention provides the above-described methods, wherein the 3' primer used in the PCR amplification is a single anchor oligo dT 3' primer.

This invention also provides the above-described methods, wherein the comparing of step (e) comprises using a gel to separate the nucleic acids from both of the libraries.

This invention provides the isolated nucleic acid identified by the the above-described methods, wherein the nucleic acid was not previously known to be differentially expressed between the two samples.

BRIEF DESCRIPTION OF THE FIGURES

FIG. 1

Figure 2:
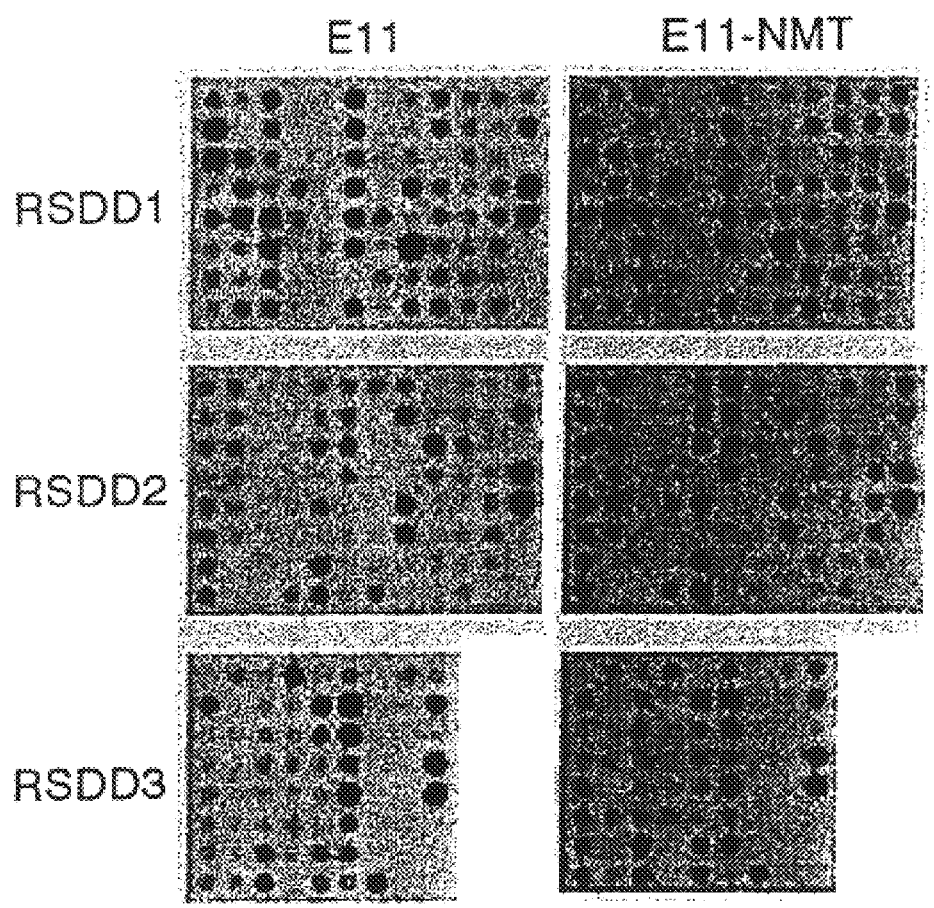

Identification of differentially expressed sequence tags using reciprocal subtraction differential RNA display (RSDD). Left panel: differential RNA display pattern of conventional DDRT-PCR with RNA from E11 (C) and E11-NMT (T) cells and an RSDD analysis of reciprocally subtracted E11 minus E11-NMT (C/T) and E11-NMT minus E11 (T/C) cDNA libraries. Right panel: representative RSDD patterns using different sets of primers.

FIG. 2

Reverse Northern analysis of differentially expressed sequence tags identified by reciprocal subtraction differential RNA display (RSDD). Differentially expressed sequence tags obtained from RSDD were dot-blotted onto Nylon membranes and probed with 32P-cDNA reverse transcribed from RNA samples of E11 and E11-NMT cells.

FIG. 3A

Differential expression of representative progression elevated genes (PEGen) and progression suppressed genes (PSGen) identified by reciprocal subtraction differential RNA display (RSDD) and reverse Northern blotting. Northern blots of E11 and E11-NMT RNA samples were probed with radiolabeled ($^{32}$P) expressed sequence tags identified by RSDD and reverse Northern blotting.

FIG. 3B

Differential expression of representative progression elevated genes (PEGen) and progression suppressed genes (PSGen) identified by reciprocal subtraction differential RNA display (RSDD) and reverse Northern blotting.

FIG. 4

Differential expression of representative progression elevated genes (PEGen) and progression suppressed genes (PSGen) identified by reciprocal subtraction differential RNA display (RSDD) and reverse Northern blotting. Northern blots of cells displaying various stages of transformation progression were probed with radiolabeled ($^{32}$P) expressed sequence tags identified by RSDD and reverse Northern blotting. The cell types used include, Unprogressed E11 (−), CREFxE11-NMT F1 (−) and CREFxE11-NMT F2 (−) somatic cell hybrids, E11xE11-NMT A6 (−) somatic cell hybrid, E11xE11-NMT 3b (−) somatic cell hybrid, and E11-NMT Aza B1 (−) and E11-NMT Aza C1 (−) 5-azacytidine treated E11-NMT clones; and Progressed E11-NMT (+), CREFxE11-NMT R1 (+) and CREFxE11-NMT R2 (+) somatic cell hybrids, E11xE11-NMT A6TD (+) nude mouse tumor derived somatic cell hybrid, E11xE11-NMT IIa (+), E11-Ras R12 (+) a Ha-ras transformed E11 clone and E11-HPV E6/E7 (+) an E11 clone transformed by the E6 and E7 region of HPV-18.

FIG. 5 cDNA fragment of PEGen 7–90% Homology to Human HPV16 E1BP. (Sequence ID No. 1)

FIG. 6 cDNA fragment of PEGen 8—Rat phosphofructose kinase C. (Sequence ID No. 2)

FIG. 7

First (Sequence ID No. 3) and second (Sequence ID No. 4) cDNA fragments of PEGen 13.

FIG. 8 cDNA fragment of PEGen 14. (Sequence ID No. 5)

FIG. 9 cDNA fragment of PEGen 15. (Sequence ID No. 6)

FIG. 10 cDNA fragment of PEGen 21 which has 94% homology to mouse FIN 14. (Sequence ID No. 7)

FIG. 11 cDNA fragment of PEGen 24. (Sequence ID No. 8)

FIG. 12 cDNA fragment of PEGen 26—Rat poly ADP-ribose polymerase. (Sequence ID No. 9)

FIG. 13 cDNA fragment of PEGen 28. (Sequence ID No. 10)

FIG. 14 cDNA fragment of PEGen 42. (Sequence ID No. 11)

FIG. 15 cDNA fragment of PEGen 43. (Sequence ID No. 12)

FIG. 16 cDNA fragment of PEGen 44. (Sequence ID No. 13)

FIG. 17 cDNA fragment of PEGen 48. (Sequence ID No. 14)

FIG. 18 cDNA fragment of PSGen 1 which has 80% homology to B. taurus supervillin. (Sequence ID No. 15)

FIG. 19 cDNA fragment of PSGen 2 which has 91% homology to human HTLV-1 Tax interacting protein. (Sequence ID No. 16)

FIG. 20 cDNA fragment of PSGen 4—Rat proteasome activator. (Sequence ID No. 17)

FIG. 21 cDNA fragment of PSGen 10—Rat Ferritin Heavy Chain. (Sequence ID No. 18)

FIG. 22 cDNA fragment of PSGen 12. (Sequence ID No. 19)

FIG. 23 cDNA fragment of PSGen 13. (Sequence ID No. 20)

FIG. 24 cDNA fragment of PSGen 23. (Sequence ID No. 21)

FIG. 25 cDNA fragment of PSGen 24. (Sequence ID No. 22)

FIG. 26 cDNA fragment of PSGen 25. (Sequence ID No. 23)

FIG. 27 cDNA fragment of PSGen 26. (SEQ ID NO: 38)

FIG. 28 cDNA fragment of PSGen 27. (SEQ ID NO: 39)

FIG. 29 cDNA fragment of PSGen 28. (SEQ ID NO: 40)

FIG. 30 cDNA fragment of PSGen 29. (SEQ ID NO: 41)

FIG. 31 cDNA fragment of PEGen 32. (SEQ ID NO: 42)

FIG. 32

Schematic outline of the reciprocal differential RNA display (RSDD) protocol. This scheme incorporates three steps, reciprocal subtraction of cDNA libraries, differential display of in vivo excised cDNAs and expression analysis by reverse Northern and standard Northern blotting. For the present application of RSDD, reciprocal subtraction hybridization was performed using libraries constructed from E11 and E11-NMT cells, i.e., E11 minus E11-NMT and E11-NMT minus E11. Differentially expressed cDNAs identified on gels using differential RNA were isolated, reamplified and analyzed for expression by reverse Northern blotting. To confirm differential expression cDNAs were analyzed using Northern blotting.

Figure 33A:
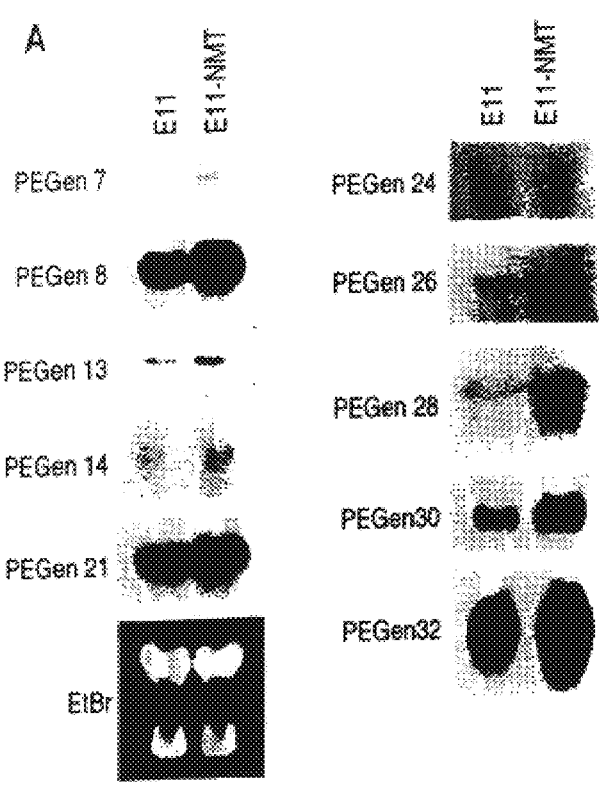
Figure 33B:
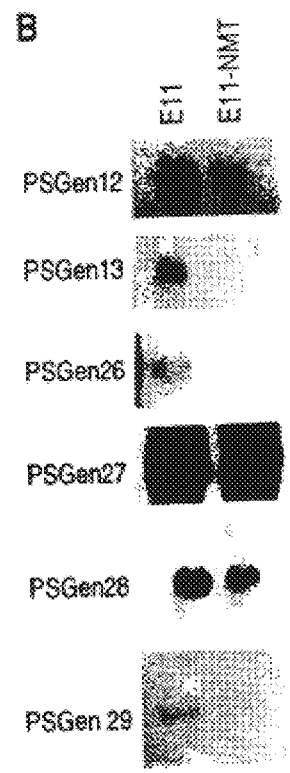

FIGS. 33A and 33B

Differential expression of representative progression elevated (PEGen) and progression suppressed genes (PSGen) identified by RSDD and reverse Northern blotting. Northern blots of E11 and E11-NMT RNA samples were probed with radiolabeled ($^{32}$P) expressed sequence tags identified by RSDD and reverse Northern blotting. Equal loading of E11 and E11-NMT RNA is demonstrated by ethidium bromide (EtBr)Staining.

Figure 34A:
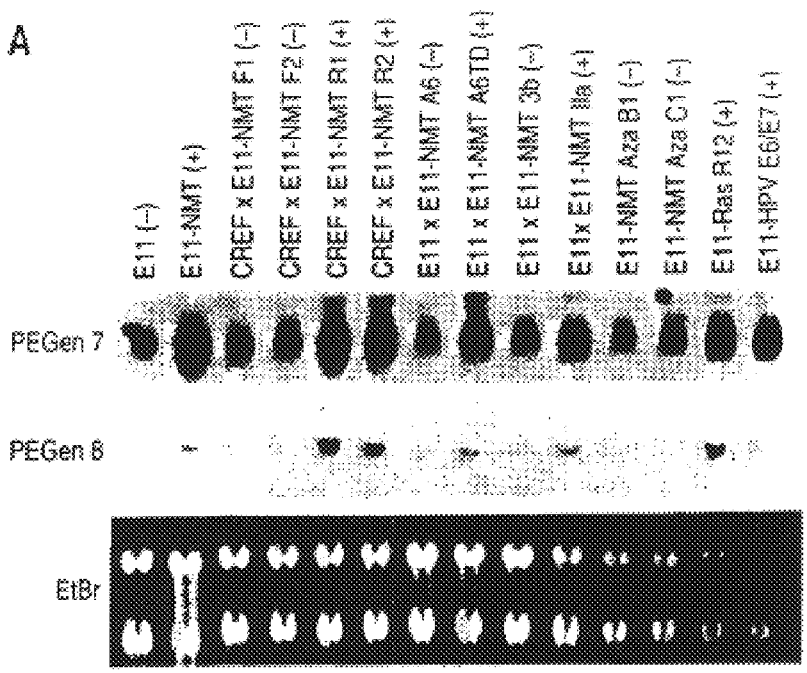
Figure 34B:
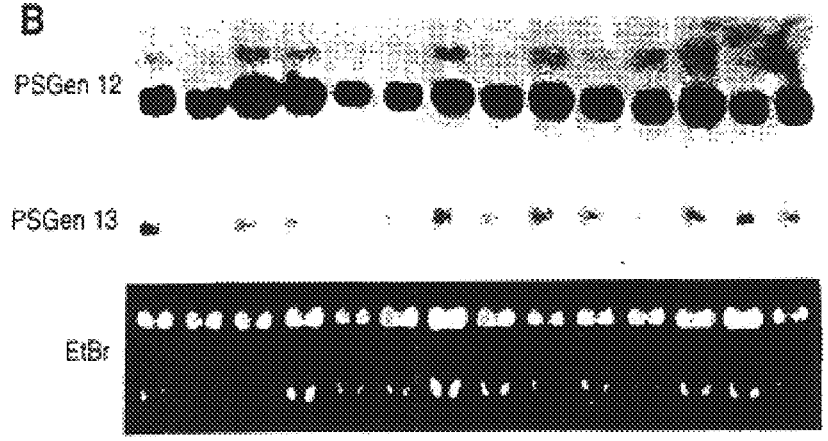

FIGS. 34A and 34B

Differential expression of representative PEGen and PSGen genes identified by RSDD and reverse Northern blotting in a large panel of rodent cells displaying differences in transformation progression. Northern blots of cells displaying various stages of transformation progression were probed with radiolabeled ($^{32}$P) expressed sequence tags identified by RSDD and reverse Northern blotting. The cell types used include: Unprogressed E11 (−), CREF X E11-NMT F1 (−) and CREF X E11-NMT F2 (−) somatic cell hybrids, E11 X E11-NMT A6 (−) somatic cell hybrid, E11 X E11-NMT 3b (−) somatic cell hybrid, and E11-NMT AZA B1 (−) and E11-NMT AZA C1 (−) 5-azacytidine-treated E11-NMT clones; and Progressed E11-NMT (+), CREF X E11-NMT R1 (+) and CREF X E11-NMT R2 (+) somatic cell hybrids, E11 X E11-NMT A6TD (+) nude mouse tumor derived somatic cell hybrid, E11 X E11-NMT IIa (+), E11-Ras R12 (+) and E11-HPV E6/E7 (+) an E11 clone transformed by the E6 and E7 region of HPV-18. Equal loading of RNAs is demonstrated by ethidium bromide (EtBr) staining.

FIG. 35A

PSGen 12 cDNA Sequence (SEQ ID NO: 24) and PSGen 12 Protein Sequence (SEQ ID NO: 25).

FIG. 35B

PSGen 13 cDNA Sequence (SEQ ID NO: 26) and PSGen 13 Protein Sequence (SEQ ID NO: 27).

FIG. 35C

PSGen 28 cDNA Sequence (SEQ ID NO: 28) and PSGen 28 Protein Sequence (SEQ ID NO: 29).

FIG. 35D

PSGen 32 cDNA Sequence (SEQ ID NO: 30) and PSGen 32 Protein Sequence (SEQ ID NO: 31).

FIG. 35E

PSGen 42 cDNA Sequence (SEQ ID NO: 32) and PSGen 42 Protein Sequence (SEQ ID NO: 33).

FIG. 35F

PEGen 45 cDNA Sequence (SEQ ID NO: 34).

FIG. 35 G-1 and FIG. 35 G-2

PEGen 50 cDNA Sequence which are different parts of the gene. (SEQ ID NO: 35 and SEQ ID NO: 36)

FIG. 36

PSGen 27—Novel (SEQ ID NO: 37).

DETAILED DESCRIPTION OF THE INVENTION

This invention provides a method for identifying differentially expressed nucleic acids between two samples, comprising: (a) selecting a first and second nucleic acid sample, wherein the nucleic acid samples contain a repertoire of nucleic acids; (b) performing reciprocal subtraction between the nucleic acid samples to produce two subtracted nucleic acid samples; (c) amplifying the two subtracted nucleic acid samples; and (d) comparing the two subtracted nucleic acid samples to identify differentially expressed nucleic acids.

In an embodiment, the nucleic acid samples are mRNA or derived from mRNA. In another embodiment, the nucleic acid samples are total RNA. In another embodiment, the nucleic acid samples are cDNA. In another embodiment, the nucleic acid samples are a nucleic acid library.

In an embodiment, differentially expressed nucleic acids are expressed at different levels. In a further embodiment, one of the nucleic acids is not expressed. In a different embodiment, one of the nucleic acids is expressed in truncated form.

As used herein, reciprocal subtraction includes using nucleic acid sample A to subtract common nucleic acids from nucleic acid sample B (based on hybridization) and also using nucleic acid sample B to subtract common nucleic acids from nucleic sample A. In an embodiment, the complement of nucleic acid sample A is used to subtract nucleic acids from nucleic acid sample B and the complement of nucleic acid sample B is used to subtract nucleic acids from nucleic acid sample A. In a further embodiment, the RNA of nucleic acid sample A is used to subtract nucleic acids from nucleic acid sample B and the RNA of nucleic acid sample B is used to subtract nucleic acids from nucleic acid sample A. In yet another embodiment, the cDNA of nucleic acid sample A is used to subtract nucleic acids from nucleic acid sample B and the cDNA of nucleic acid sample B is used to subtract nucleic acids from nucleic acid sample A.

As used herein, methods of amplification include PCR and rolling circle replication.

A basic description of nucleic acid amplification is described in Mullis, U.S. Pat. No. 4,683,202, which is incorporated herein by reference. The amplification reaction uses a template nucleic acid contained in a sample, two primer sequences and inducing agents. The extension product of one primer when hybridized to the second primer becomes a template for the production of a complementary extension product and vice versa, and the process is repeated as often as is necessary to produce a detectable amount of the sequence.

The inducing agent may be any compound or system which will function to accomplish the synthesis of primer extension products, including enzymes. Suitable enzymes for this purpose include, for example, *E.coli* DNA polymerase I, thermostable Taq DNA polymerase, Klenow fragment of *E.coli* DNA polymerase I, T4 DNA polymerase, other available DNA polymerases, reverse transcriptase and other enzymes which will facilitate combination of the nucleotides in the proper manner to form amplification products. The oligonucleotide primers can be synthesized by automated instruments sold by a variety of manufacturers or can be commercially prepared based upon the nucleic acid sequence of this invention.

This invention also provides a method for identifying differentially expressed nucleic acids between two samples, comprising: a) selecting a first and second nucleic acid sample; b) producing libraries for the first and second nucleic acid sample; c) amplifying the two libraries; d) performing reciprocal subtraction between the amplified libraries to produce two subtracted libraries; and e) comparing the two subtracted libraries to identify differentially expressed nucleic acids.

This invention also provides a method for identifying differentially expressed nucleic acids between two samples, comprising: (a) selecting a first and second nucleic acid sample, wherein the nucleic acid samples contain a repertoire of nucleic acids; (b) amplifying the two nucleic acid samples; (c) performing reciprocal subtraction between the amplified nucleic acid samples to produce two subtracted nucleic acid samples; and (d) comparing the two subtracted nucleic acid samples to identify differentially expressed nucleic acids.

This invention also provides the above-described methods, wherein the two subtracted nucleic acid samples from step c are amplified prior to the comparing of step d.

This invention also provides the above-described methods, wherein the each of the nucleic acid samples comprises a library of nucleic acids.

This invention also provides the above-described methods, wherein the nucleic acid samples are obtained from total cellular RNA purified by hybridization with oligo (dT).

This invention also provides the above-described methods, wherein the nucleic acid samples are obtained from total RNA from E11 and E11-NMT cells.

E11 is an adenovirus-transformed rat embryo cell line that acquires an aggressive oncogenic progression phenotype when injected into athymic nude mice and reisolated in cell culture (E11-NMT).

This invention further provides the above-described methods, wherein the first and second nucleic acid samples are obtained from cells in different developmental stages.

This invention further provides the above-described methods, wherein the first and second nucleic acid samples are obtained from cells from different tissue types.

This invention further provides the above-described methods, wherein the first and second nucleic acid samples are obtained from cells that differ in their exposure to external factors or in their gene expression.

In an embodiment, cells that differ in their exposure to external factors or in their gene expression includes any cells that may have different levels of gene expression, wherein some genes may not be expressed at all. In another embodiment, cells that differ in their exposure to external factors or in their gene expression includes any cells that are likely to have different levels of gene expression, wherein some genes may not be expressed at all. In still another embodiment, cells that differ in their exposure to external factors or in their gene expression includes any cell that has a phenotypically recognizable difference.

A short list of examples of cells that differ in their exposure to external factors or in their gene expression includes: cancerous versus normal cells, advanced cancer progression cells versus ealier cancer stage cells, diseased cells versus nondiseased cells, infected cells versus noninfected cells, later developmental stage cells versus earlier developmental stage cells, cells after DNA damage versus cells before DNA damage, senescent cells versus younger cells, cells induced by growth factors versus cells not induced by growth factors, cells in the process of neurodegeneration versus normal cells, and cells exposed to a chemotherapeutic agent versus normal cells.

As used herein, different tissues types include but are not limited to tissues containing: cells grown under or exposed to different conditions, cells in different stages of development, cells treated with agents modifying cellular physiology, and cells having different functions.

In an embodiment, cells at different stages of development are cells taken or analyzed at times is differing by one or more hours in the development of the cell or organism.

Further, this invention provides the above-described methods, wherein the amplifying of step (d) comprises PCR amplification.

Also, this invention provides the above-described methods, wherein the 3' primer used in the PCR amplification is an oligo dT 3' primer. A few examples of oligo dT primers are $T_{13}A$, $T_{13}A$, and $T_{13}G$.

In addition, this invention provides the above-described methods, wherein the 3' primer used in the PCR amplification is a single anchor oligo dT 3' primer. Olgio dT 3' primers include $T_{13}A$, $T_{13}C$, and $T_{13}G$.

This invention provides the above-described methods, wherein the PCR amplification uses a set of random primers.

This invention provides the above-described methods, wherein the 5' primer is an arbitrary primer.

This invention also provides the above-described methods, wherein the comparing of step (e) comprises using a gel to separate the nucleic acids from both of the substracted libraries.

In an embodiment, the gel is a polyacrylamide gel. In another embodiment, the gel is an agarose gel.

This invention further provides the above-described methods, further comprising PCR amplifying the first and second nucleic acid samples.

This invention also provides the above-described methods, further comprising reamplifying differentially expressed bands.

This invention also provides the above-described methods, further comprising reamplifying differentially expressed nucleic acid.

In one method of reamplifying differentially expressed bands, differentially amplified bands from plasmids of each subtracted library were marked with an 18G needle through the film and cut out with a razor. The cut out differentially expressed bands can be reamplified (i.e. by PCR) and examined by reverse Northern and Northern blot analyses.

In addition, this invention provides the above-described methods, wherein the comparing of step (e) comprises comparing the band intensities of the two amplified differentially expressed nucleic acids.

In addition, this invention provides the above-described methods, wherein the nucleic acid samples are mRNA or cDNA derived from mRNA.

In addition, this invention provides the above-described methods, wherein the comparing of step (e) comprises comparing the quantities of the two amplified differentially expressed nucleic acids.

This invention also provides the above-described isolated nuclcic acid, wherein the isolated nucleic acid is the nucleic acid designated PSGen 12 (Accession No. AI 144569) (SEQ ID NO: 19).

This invention also provides the above-described isolated nucleic acid, wherein the isolated nucleic acid is the nucleic acid designated PSGen 13 (Accession No. AI 144570) (SEQ ID NO: 20).

In one embodiment, electronic quantification involves using a scanner to detect the bands. In a further embodiment, computer software, such as Corel Draw, can be used to determine the pixel intensity of the scanned image, thereby quantifying the band intensity.

Also, this invention provides the above-described methods, wherein the libraries of step (b) are constructed with λ-ZAP cDNA library kits. One skilled in the art would recognize that any cDNA library would be suitable.

This invention provides the isolated nucleic acid identified by the the above-described methods, wherein the nucleic acid was not previously known.

This invention also provides the above-described isolated nucleic acid, wherein the isolated nucleic acid is the nucleic acid designated PSGen 12 (AI 144569).

In addition, this invention provides the above-described isolated nucleic acid, wherein the isolated nucleic acid is the nucleic acid designated PSGen 13 (Accession No. AI 144570).

This invention also provides the above-described isolated nucleic acid, wherein the isolated nucleic acid is the nucleic acid designated PSGen 23 (SEQ ID NO: 21).

This invention also provides the above-described isolated nucleic acid, wherein the isolated nucleic acid is the nucleic acid designated PSGen 24 (SEQ ID NO: 22).

This invention also provides the above-described isolated nucleic acid, wherein the isolated nucleic acid is the nucleic acid designated PSGen 25 (SEQ ID NO: 23).

This invention also provides the above-described isolated nucleic acid, wherein the isolated nucleic acid is the nucleic acid designated PSGen 26 (Accession No. AI 144571) (SEQ ID NO: 38).

This invention also provides the above-described isolated nucleic acid, wherein the isolated nucleic acid is the nucleic acid designated PSGen 27 (Accession No. AI 144572) (SEQ ID NO: 39).

This invention also provides the above-described isolated nucleic acid, wherein the isolated nucleic acid is the nucleic acid designated PSGen 28 (Accession No. AI 144573) (SEQ ID NO: 40).

This invention also provides the above-described isolated nucleic acid, wherein the isolated nucleic acid is the nucleic acid designated PSGen 29 (Accession No. AI 144574 (SEQ ID NO: 41).

This invention also provides the above-described isolated nucleic acid, wherein the isolated nucleic acid is the nucleic acid designated PEGen 13 (Accession No. AI 144564) (SEQ ID NOS: 3 and 4).

This invention also provides the above-described isolated nucleic acid, wherein the isolated nucleic acid is the nucleic acid designated PEGen 14 (Accession No. AI 144565) (SEQ ID NO: 5).

This invention also provides the above-described isolated nucleic acid, wherein the isolated nucleic acid is the nucleic acid designated PEGen 15 (SEQ ID NO: 6).

This invention also provides the above-described isolated nucleic acid, wherein the isolated nucleic acid is the nucleic acid designated PEGen 24 (Accession No. AI 144566) (SEQ ID NO: 8).

This invention also provides the above-described isolated nucleic acid, wherein the isolated nucleic acid is the nucleic acid designated PEGen 28 (Accession No. AI 144567) (SEQ ID NO: 10).

This invention also provides the above-described isolated nucleic acid, wherein the isolated nucleic acid is the nucleic acid designated PEGen 32 (Accession No. AI 144568) (SEQ ID NO: 42).

This invention also provides the above-described isolated nucleic acid, wherein the isolated nucleic acid is the nucleic acid designated PEGen 42 (SEQ ID NO: 11).

This invention also provides the above-described isolated nucleic acid, wherein the isolated nucleic acid is the nucleic acid designated PEGen 43 (SEQ ID NO: 12).

This invention also provides the above-described isolated nucleic acid, wherein the isolated nucleic acid is the nucleic acid designated PEGen 44 (SEQ ID NO: 13).

This invention also provides the above-described isolated nucleic acid, wherein the isolated nucleic acid is the nucleic acid designated PEGen 48 (SEQ ID NO: 14).

This invention further provides a previously unknown isolated nucleic acid molecule identified by the above-described methods which comprises (a) one of the nucleic acid sequences as set forth in FIG. 35 (SEQ ID NOS: 24, 26, 28, 32, and 34–36); a sequence being degenerate to a sequence of (a) as a result of the genetic code; (c) a sequence encoding one of the amino acid sequences as set forth in FIG. 35 (SEQ ID NOS: 25, 27, 29, 31, and 33); (d) a sequence of at least 12 nucleotides capable of specifically hybridizing to the sequence of (a), (b) or (c).

Finally, this invention provides a purified polypeptide comprising one of the amino acid sequences as set forth in FIG. 35 (SEQ ID NOS: 25, 27, 29, 31, and 33).

The sequences of the cDNAs of PSGen 12 (SEQ ID NO: 19), PSGen 13 (SEQ ID NO: 20), PSGen 26 (SEQ ID NO: 38), PSGen 27 (SEQ ID NO: 39), PSGen 28 (SEQ ID NO: 40), PSGen 29 (SEQ ID NO: 41), PEGen 13 (SEQ ID NOS: 3 and 4), PEGen 14 (SEQ ID NO: 5), PEGen 24 (SEQ ID NO: 8), PEGen 28 (SEQ ID NO: 10), and PEGen 32 (SEQ ID NO: 42) were submitted to GenBank and assigned with accession numbers AI 144569, AI 144570, AI 144571, AI 144572, AI 144573, AI 144574, AI 144564, AI 144565, AI 144566, AI 144567 and AI 144568, respectively.

This invention will be better understood from the Experimental Details which follow. However, one skilled in the art will readily appreciate that the specific methods and results discussed are merely illustrative of the invention as described more fully in the claims which follow thereafter.

Experimental Details

We presently describe a reciprocal subtraction differential RNA display (RSDD) approach that efficiently and consistently reduces the complexity of DDRT-PCR and results in the identification and cloning of genes displaying anticipated differential expression. Proof of principle for the RSDD approach has come from its application for the identification of genes differentially expressed during cancer progression. RSDD has resulted in the identification and cloning of genes displaying elevated expression in progressed tumor cells (PEGen) and reduced expression in progressed tumor cells (PSGen). The model used for RSDD was an adenovirus-transformed rat embryo cell line, E11, that acquires an aggressive oncogenic progression phenotype when injected into athymic nude mice and reisolated in cell culture (E11-NMT) (10,33,34). Injection of E11 cells into nude mice results in tumors in 100% of animals with a tumor latency time of approximately 35 to 40 days, whereas E11-NMT cells form tumors in 100% of nude mice with a tumor latency time of 15 to 20 days (10,34,35). Additionally, E11 cells form colonies in agar with an efficiency of ~3%, whereas E11-NMT display an agar cloning efficiency of >30% (10,33,34). The increased tumorigenicity and enhanced anchorage independence phenotypes are key indicators of tumor progression in the E11/E11-NMT model system (10,33,34).

Differential RNA display was directly performed with reciprocally subtracted cDNA plasmid libraries (E11 minus E11-NMT and E11-NMT minus E11). Compared with the subtraction of PCR-amplified cDNA in Hakvoort et al., the subtracted cDNA libraries used in this experiment are free from potential PCR artifacts and provide more stable and consistent sources for DDRT-PCR analyzes. In addition, three single anchored oligo dT 3' primers were used instead of two-base-anchored approach described by Hakvoort et al (32). To further streamline the DDRT-PCR procedure, reamplified cDNAs identified using RSDD were analyzed using the reverse Northern blotting procedure (35,36). cDNAs displaying differential expression by reverse Northern blotting were subsequently confirmed for true differential expression by Northern analysis. These modifications incorporated in the RSDD strategy result in an efficient approach for using subtractive hybridization and DDRT-PCR for identifying differentially expressed genes.

Methods

Total RNA from E11 and E11-NMT cells was isolated by the guanidinium isothiocyanate/CsCl centrifugation procedure and poly $A^+$ RNA was purified with oligo(dT) cellulose chromatography (5). Two λ-ZAP cDNA libraries from E11 and E11-NMT mRNA's were constructed with λ-ZAP cDNA library Kits (Stratagene) following the manufacturer's protocol. Reciprocal subtraction between E11 and E11-NMT libraries was performed and two subtracted cDNA libraries (E11 minus E11-NMT and E11-NMT minus E11) were constructed as described previously. Bacterial plasmid libraries from the subtracted λ-ZAP cDNA libraries were obtained by in vivo excision following the manufacturer's protocol (Stratagene) and the plasmids were isolated with Qiagen columns (Qiagen Inc.).

The purified plasmids of reciprocally subtracted cDNA libraries were directly subjected to differential display as in Liang et. al. (38) with minor modifications. The plasmids of reciprocally subtracted cDNA libraries were PCR-amplified with the combination of three single-anchor 3' primers ($T_{13}A$, $T_{13}C$ or $T_{13}G$) and 18 arbitrary 5' 10-mer primers obtained from Operon Technology Inc. (Alameda, Calif. OPA 1–20 except OPA1 and 3). The 20 µl PCR reaction consisted of 10 mM Tris-HCl pH 8.4, 50 mM KCl, 1.5 mM $MgCl_2$, 2 µM each dNTP, 0.2 µM 5' arbitrary primer, 1 µM 3' anchor primer, 50 ng of plasmid of a subtracted library, 10 µCi α-$^{35}$S-DATP (3000 Ci/mmole from Amersham) and 1 U of Taq DNA polymerase (Gibco BRL). The parameters of PCR were 30 sec at 95 C., 40 cycle of 30 sec at 95 C., 2 min. at 40 C. and 30 sec at 72 C. and additional 5 min. at 72 C. After the cycling, 10 µl of 95% formamide, 0.05% bromophenol blue and 0.05% xylene cyanol were added to each PCR reaction. The mixture was heated at 95° C. for 2 min and separated in a 5% denaturing DNA sequencing gel maintained at 50° C. PCR reactions of plasmids from each subtracted library in a primer set were run side by side. Differentially amplified bands from plasmids of each subtracted library were marked with an 18 G needle through the film and cut out with a razor. The gel slice was put in 100 µl TE pH 8.0 and incubated at 4° C. overnight. After the incubation, the mixture was boiled for 5 min and microcentrifuged for two min. The supernatant was collected and stored at −20° C. until reamplification. The band extract was reamplified with the same cycling parameters in a 50 µl reaction consisting of 10 mM Tris-HCl pH 8.4, 50 mM KCl, 1.5 mM $MgCl_2$, 20 µM each dNTP, 0.2 µM 5' arbitrary primer, 1 µM 3' anchor primer, 5 µl of band extract and 2.5 U of Taq DNA polymerase (Gibco BRL).

Differential expression of the reamplified DNA fragment was scrutinized by reverse Northern and Northern blot analyses. In reverse Northern analysis, after confirmation in a 1% agarose gel, the reamplified DNA fragment (10 µl of PCR reaction) was mixed with 90 µl TE and spotted on a positively charged Nylon membrane (Boehringer Mannheim) with a 96-well vacuum manifold. The membrane was soaked with denaturing and neutralizing solution successively, and the spotted DNA was crosslinked to the membrane with a UV crosslinker (Stratagene). $^{32}$P-labeled first strand cDNA was prepared by reverse transcription of total RNA. After heating at 70° C. for 10 min and quenching on ice for two min, 0.4 μM each $T_{13}A$, $T_{13}G$ and $T_{13}C$ and 10 μg total RNA mixture was added with 50 mM Tris-HCl, pH 8.3, 75 mM KCl, 3 mM MgCl2, 10 mM DTT, 0.5 mM DATP, 0.5 mM dGTP, 0.5 mM dTTP, 0.02 mM dCTP, 0.5 μl RNase inhibitor (Gibco BRL), 100 μCi dCTP (3000 Ci/mmole from Amersham) and 200 U Superscript RT II (Gibco BRL) in a final 25 μl reaction. The reaction mixture was incubated at 42° C. for one hr and at 37° C. for 30 min after addition of 2 μl of RNase H (10 U, Gibco BRL). The membrane was hybridized at 42° C. overnight in a 50% formamide hybridization solution. The hybridized membrane was washed at room temperature for 15 min with 2×SSC containing 0.1% SDS twice and at 55° C. for at least one hr with 0.1×SSC containing 0.1% SDS, successively. The membrane was probed with the $^{32}$P-labeled cDNA of E11, stripped off and probed with $^{32}$P-labeled cDNA of E11-NMT. The signal intensity of each spot was normalized against that of GAPDH and compared between E11 and E11-NMT. Reamplified DNA fragments displaying differential expression levels ≧1.8-fold higher between the two cell types were selected and analyzed by Northern blotting analysis.

In Northern blot analysis, 10 μg of total RNA from E11 and E11-NMT cells were run side-by-side in a 1% agarose gel with formaldehyde and transferred to a positively charged Nylon membrane. Reamplification reaction (5 μl) was $^{32}$P-labeled with a multiprime labeling kit (Boehringer Mannheim) used to probe the membrane as described above. DNA fragments expressed differentially between E11 and E11-NMT in Northern blot analyses were cloned into the Eco RV site of the pZEro-2.1 cloning vector (Invitrogene) and sequenced. In order to confirm differential expression, the cloned cDNA fragment was released by Eco RI-Xho I, $^{32}$P-labeled and used to probe Northern blots as described above. Samples of RNAs from various E11 and E11-NMT derivatives displaying either a progressed or suppressed progression phenotype, based on nude mice tumorigenesis and soft agar cloning assays were analyzed. These included E11, E11-NMT, CREF X E11-NMT F1 and F2 somatic cell hybrids (suppressed progression phenotype), CREF X E11-NMT R1 and R2 somatic cell hybrids (progression phenotype), E11 X E11-NMT A6 somatic cell hybrid (suppressed progression phenotype), E11 X E11-NMT A6TD tumor-derived somatic cell hybrid (progression phenotype), E11 X E11-NMT 3b somatic cell hybrid (suppressed progression phenotype), E11 X E11-NMT 2a (progression phenotype), E11-NMT AZA B1 and C1 5-azacytidine treated E11-NMT clones (suppressed progression phenotype), E11-ras R12 clone containing the Ha-ras oncogene (progression phenotype) and E11-HPV E6/E7 clone containing the human papilloma virus-18 E6 and E7 gene region (progression phenotype). Differential expression of the PEGen and PSGen genes in the various cell types was confirmed using $^{32}$P-labeled probes and Northern hybridization analysis. After reconfirmation of differential expression, the plasmids containing the differentially expressed DNA fragments were sequenced by the dideoxy sequencing procedure.

Results and Discussion

Figure 1:
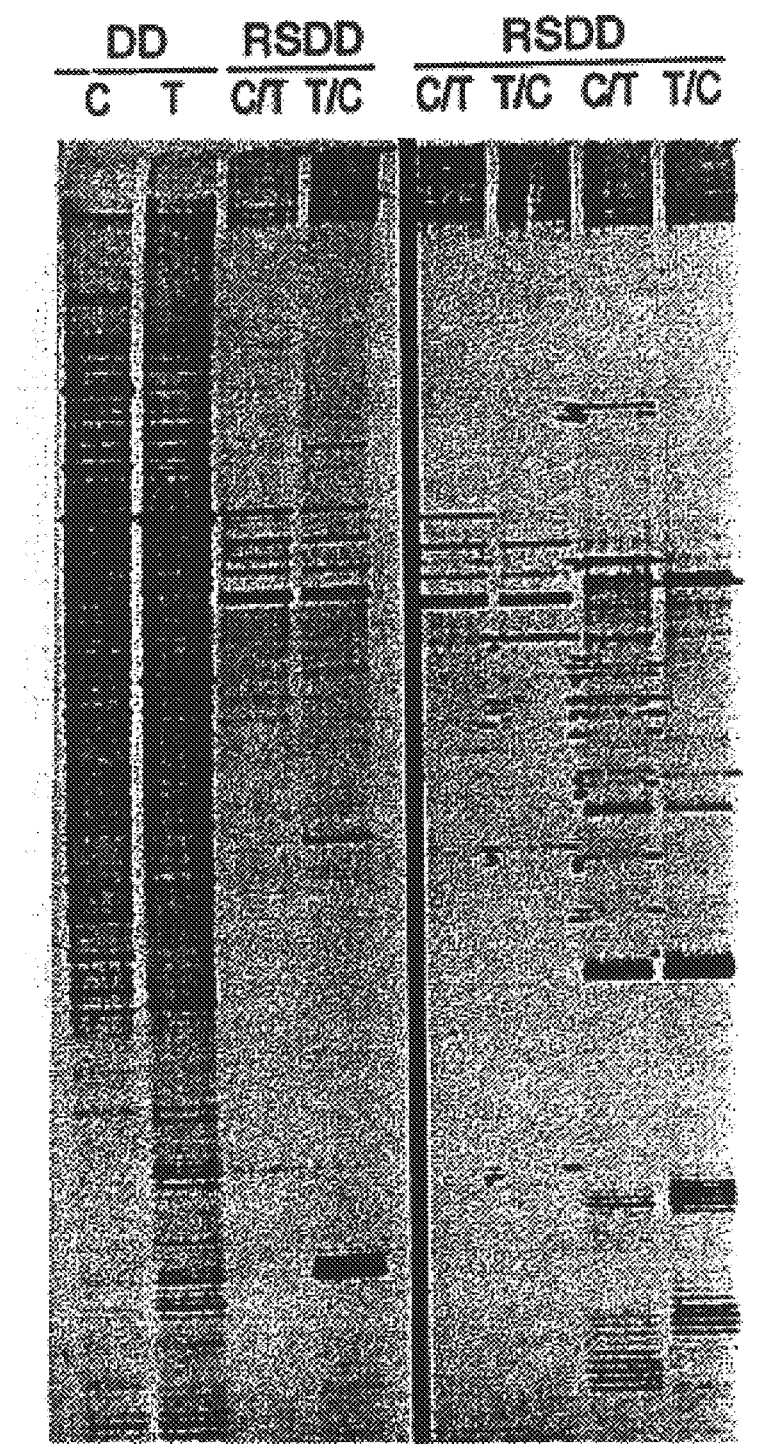

Subtraction hybridization provides a direct means of enriching for unique cDNA species and eliminating common sequences between complex genomes. DDRT-PCR is a proven methodology for the rapid identification and cloning of differentially expressed sequences between cell types (3,4,22). In principle, subtraction hybridization combined with DDRT-PCR should reduce band complexity which often obscures the identification of differentially expressed genes and generates false positive signals (23,28). This strategy, RSDD, has been used to analyze genes differentially expressed during transformation progression. The differential RNA display pattern of E11 and E11-NMT cells using standard differential RNA display DDRT-PCR) and RSDD is shown in FIG. 1 (Left Panel). As predicted, the differential RNA display pattern of RSDD was much less complex than that of DDRT-PCR. The majority of bands common to both cDNA samples were eliminated using RSDD. These experiments demonstrate that subtractive hybridization prior to differential RNA display is effective in simplifying display patterns permits the efficient identification of differentially expressed cDNAs. Since RSDD significantly reduced the number of bands displayed, single anchor oligo dT primers, that can increase band numbers, were successfully used in subsequent applications of the RSDD approach (FIG. 1; Right Panel). Using RSDD, 235 differentially displayed cDNAs in the E11/E11-NMT tumor progression model system were isolated.

Hakvoort et. al. (32) used a reciprocal subtraction approach to analyze gene expression changes resulting during liver regeneration following 70% hepatectomy, i.e., normal liver subtracted from partially hepatectomized regenerating liver and vice versa. Although some bands displayed apparent enrichment, the complexity of the display pattern did not show appreciable simplification. These results are in stark contrast to RSDD, which results in a clear delineation and simplification of differentially expressed amplified bands (FIG. 1). Although conceptually similar, RSDD is significantly more effective than the subtraction plus DDRT-PCR approach described by Hakvoort et al. (32). The improved efficiency of RSDD versus the Hakvoort et al. (32) approach can be attributed to several factors. The approach of Hakvoort et al. (32) is based on the subtraction procedure described by Wang and Brown (38). This approach involves multiple rounds of PCR-amplification prior to each round of subtractive hybridization. In contrast, RSDD involves a single round of reciprocal subtraction that does not involve PCR amplification (5,10). In this respect, the complicated display pattern observed by Hakvoort et al. (32) even after three or four rounds of subtraction might result from reduced subtraction efficiency, PCR artifacts or a combination of these problems. Increasing the number of reactions by using two-base pair anchored oligo dT primers did not reduce the complexity of displayed bands (32). In these contexts, a critical component for the successful use of RSDD involves the use of an appropriate subtraction hybridization protocol, that can efficiently reduce cDNA complexity and generate stable populations of cDNAs for analysis.

Previous studies demonstrate that different gene cloning strategies, including DDRT-PCR, subtraction hybridization and electronic display, identify dissimilar differentially expressed genes (18). These results suggest that a single approach for gene identification may not identify the complete spectrum of differentially expressed genes (18). Similarly, RSDD and DDRT-PCR do not resolve the same differentially expressed bands (FIG. 1). Unique bands identified in DDRT-PCR that were differentially expressed when analyzed by Northern blotting were not the same as those found using RSDD and vise versa. These results are not surprising, since, as indicated above, subtraction hybridization and differential RNA display identified distinct differentially expressed genes. Apparently, specific differentially expressed genes are lost during subtraction hybridization and differential RNA display of subtracted cDNAs. On the basis of these considerations, it will be essential to use multiple gene discovery approaches to identify and clone the complete spectrum of differentially expressed genes.

DDRT-PCR can generate large numbers of differentially displayed bands making subsequent analysis both labor intensive and a daunting challenge. In order to reduce these limitations of DDRT-PCR, RSDD has been used in combination with reverse Northern analyses of isolated cDNAs. Gel extracted cDNA fragments were reamplified, dot-blotted on Nylon membranes and successively probed with reverse transcribed $^{32}$P-cDNA from E11 or E11-NMT RNAs (FIG. 2). Signals were detected in 181 reamplified bands out of 235 (77%). This number is lower than that observed using DDRT-PCR (51 out of 54). However, this comparison may not be accurate since only four arbitrary primers were used for DDRT-PCR and fewer differentially expressed bands were detected and isolated. A possible reason for the high incidence of false positives in RSDD may be due to the existence of foreign plasmid-like DNA in the cDNAs and the inaccurate reading properties of DDRT-PCR.

TABLE 1

Differentially Expressed cDNA Fragments Cloned by DDRT-PCR.

| Nomenclature | Identity | Homology |
| --- | --- | --- |
| PEGen 41 | To be determined | |
| PEGen 42 | Novel | Novel |
| PEGen 43 | Novel | Novel |
| PEGen 44 | Novel | Novel |
| PEGen 45 | Hoxa11 locus antisense | mouse 90% |
| PEGen 46 | Glutamyl t-RNA synthetase | human 59% |
| PEGen 48 | Novel | Novel |
| PEGen 50 | Novel | Novel |
| PSGen 1 | Supervillin | B. taurus 80% |
| PSGen 2 | HTLV-1 Tax interacting protein | human 91% |
| PSGen 4 | Proteasome activator | Rat 100% |
| PSGen 27 | Novel | |

The signal intensities of the various cDNAs in reverse Northern analysis were quantified and normalized against that of GAPDH, which remained unchanged in E11 and E11-NMT cells. The PEG-3 (PEGen-3) gene (10) was used as an additional control, to verify increased expression in E11-NMT versus E11 cells. In the reverse Northern analyses, PEGen-3 levels were 4-fold higher in E11-NMT than in E11 cells, which coincided with Northern blotting results, thereby demonstrating the concordance of reverse Northern and Northern assays. A $\geq 1.8$-fold differential cut-off (after normalization for GAPDH expression) was used to identify and isolate cDNA bands displaying modified expression in E11 versus E11-NMT cells. This resulted in the identification of 7 cDNAs with higher expression in E11 versus E11-NMT cells and 65 cDNAs with elevated expression in E11-NMT versus E11 cells. These results suggest that tumor progression in E11-NMT cells correlates with the increased expression of a large number of genes, whereas only a smaller subset of genes display decreased expression.

A problem present in DDRT-PCR, that is reduced but still can occur in RSDD, is the isolation of multiple cDNA species from what appears to be a single amplified band. When this occurs, these multiple species can produce spurious results when analyzed by reverse Northern analyses. For example, if two distinct species are isolated, one displaying modified expression and a second not displaying modified expression, an accurate estimate of differential expression will not be obtained by reverse Northern analysis. In this case, a number of potential false positives generated using reverse Northern analyses, may in reality not be false positives, but instead may represent multiple cDNAs. This problem may be ameliorated by performing single strand conformational polymorphism (SSCP) or reverse Northern analyses using cloned cDNA populations (39,40).

Figure 3B:
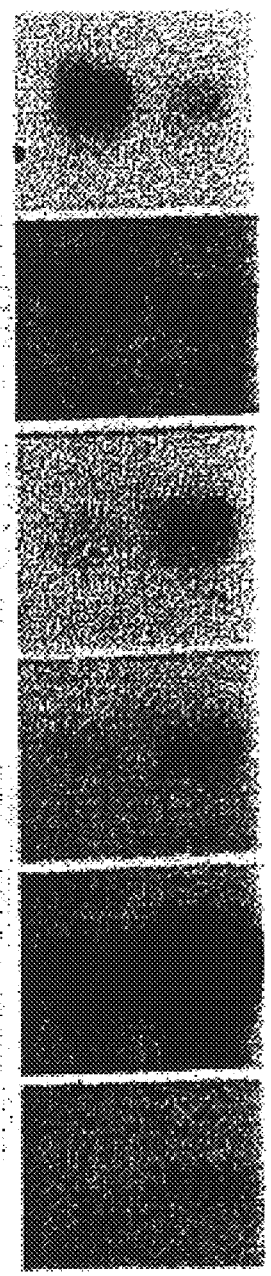
Figure 32:
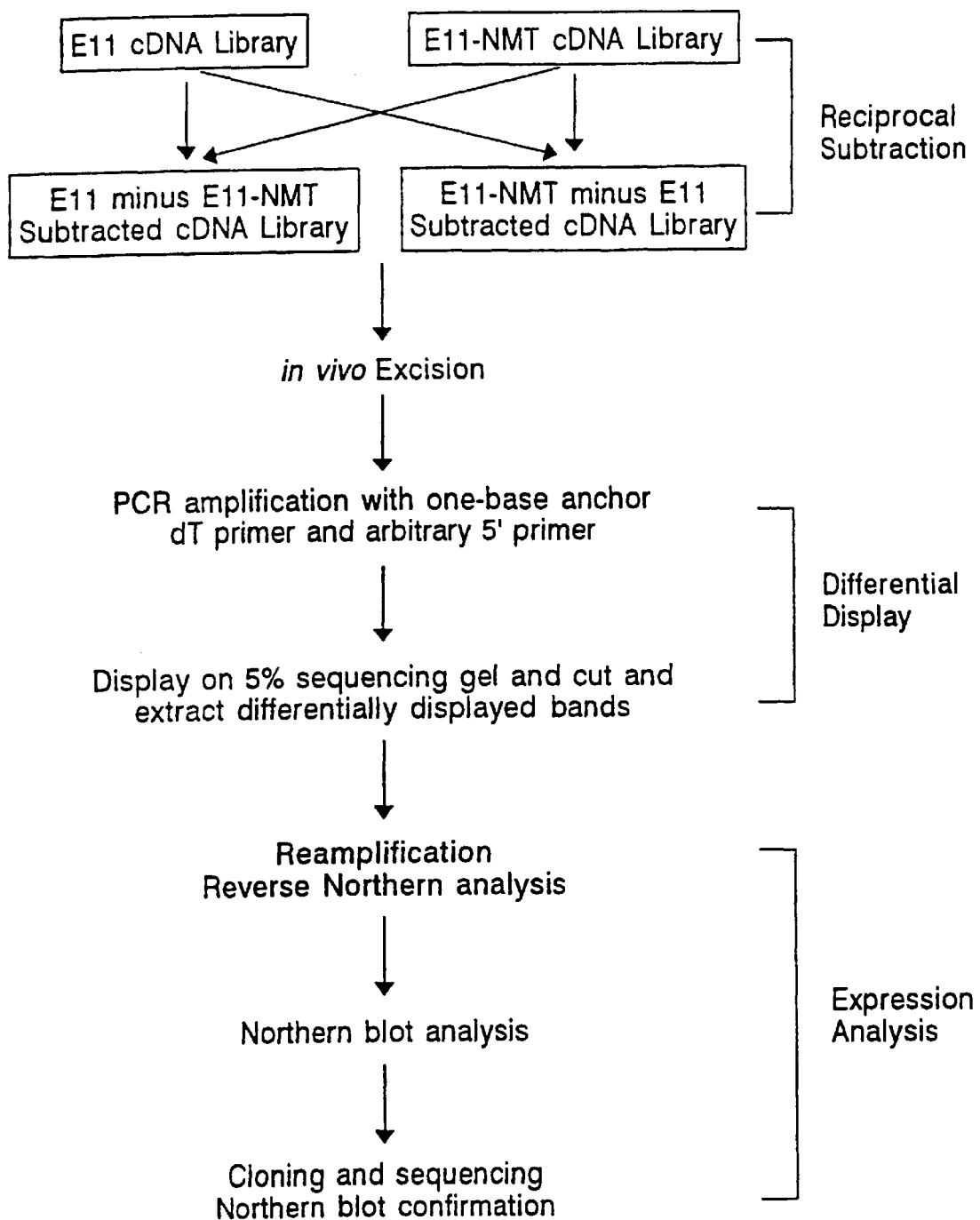

The expression pattern of representative RSDD-derived cDNAs in E11 versus E11-NMT and in a more expanded E11/E11-NMT progression cell culture series is shown in FIGS. 3 and 4, respectively. Reverse Northern results correlated well with Northern blots using E11 and E11-NMT (~80% concordance) or a larger panel of cells differentially displaying the progression phenotype, including progression negative, E11, CREF x E11-NMT F1, CREF X E11-NMT F2, E11 X E11-NMT A6, E11 X E11-NMT 3b, E11-NMT Aza B1 and E11-NMT Aza C1, and progression positive E11-NMT, CREF X E11-NMT R1, CREF X E1-NMT R2, E11 X E11-NMT A6TD, E11 X E11-NMT IIa, E11-ras and E11-HPV E6/E7. Sequence analysis of the various progression upregulated genes (PEGen) and progression suppressed genes (PSGen) identified both known and unknown genes (Table 2). Known PEGen genes included PEGen 7 (HPV16 E1BP), PEGen 8 (PFK-C), PEGen 21 (FIN 14) and PEGen 26 (poly ADP-ribose polymerase) and a known PSGen gene was PSGen 10 (ferritin heavy chain). Two PEGen genes out of six were found to be novel (PEGen 14 and PEGen 24) and two PSGen genes out of three were found to be novel (PSGen 12 and PSGen 13) (Table 2).

TABLE 2

Differentially Expressed cDNA Fragments Cloned by RSDD

| Nomenclature | Identity | Homology |
| --- | --- | --- |
| PEGen 7 | HPV16 E1BP | Human 90% |
| PEGen 8 | PFK-C | Rat 100% |
| PEGen 13 | Novel | Novel |
| PEGen 14 | Novel | Novel |
| PEGen 15 | Novel | Novel |
| PEGen 21 | FIN 14 | Mouse 94% |
| PEGen 24 | Novel | Novel |
| PEGen 26 | Poly ADP-ribose Polymerase | Rat 100% |
| PEGen 28 | Novel | Novel |
| PEGen 32 | Novel | Novel |
| PSGen 10 | Ferritin Heavy Chain | Rat 100% |
| PSGen 12 | Novel | Novel |
| PSGen 13 | Novel | Novel |
| PSGen 23 | Novel | Novel |
| PSGen 24 | Novel | Novel |
| PSGen 25 | Novel | Novel |
| PSGen 26 | Navel | Novel |
| PSGen 27 | Novel | Novel |
| PSGen 28 | Novel | Novel |
| PSGen 29 | Novel | Novel |

PEGen 7 is expressed at ~5-fold higher levels in E11-NMT than in E11 cells. PEGen 7 is ~90% homologous to 16E1-BP, a cDNA encoding a protein identified using the yeast two-hybrid assay that interacts with human papillomavirus type 16 E1 protein (41). 16E1-BP encodes a 432aa protein of unknown function but does contain an ATPase signature motif (Gly-X4-Gly consensus ATP binding motif at aa 179 through 186). 16E1-BP appears to be a form of TRIP13, a protein previously shown to bind thyroid hormone receptor in yeast two-hybrid assays. The role of PEGen 7/16E1-BP in the progression phenotype in the E11/E11-NMT progression model is not known. Additional studies are necessary to determine if this gene change is associative or causative of transformation progression.

PEGen 8 is expressed at ~3- to 4-fold higher levels in E11-NMT than in E11 cells. PEGen 8 shows 100% homology to rat phosphofructokinase C (PFK-C) (42). PFK catalyzes the rate-limiting and committed step in glycolysis, the conversion of fructose 6-phosphate to fructose 1,6-biphosphate. Three subunit isozymes of PFK have been identified, that form homo- and heterotetramers with differing catalytic and allosteric properties. PFK-M is specific for cardiac and skeletal muscle, PFK-L is expressed in many tissues but is most abundant in the liver and PFK-C is expressed in several brain regions and the anterior pituitary but not in liver, skeletal muscle, or several other human tissues. The cDNA of PFK-C isolated from a rat hypothalamic cDNA library is 2643 bp and encodes a protein of 765aa (42). In a recent study, Sanchez-Martinez and Aragon (43) demonstrated that PFK-C is the predominant form of PFK in ascites tumor cells (obtained from a transplantable mouse carcinoma of mammary origin), whereas PFK-L is most abundant in the normal mammary gland. These results suggest the interesting possibility that PFK-C might contribute to the malignant nature of specific target cells. The role of PEGen 8/PFK-C in progression in the E11/E11-NMT model remains to be determined.

PEGen 21 is expressed at ~3- to 4-fold higher levels in E11-NMT than in E11 cells. PEGen 21 displays ~94% homology with the fibroblast growth factor-4 inducible gene FIN-14 (44). FIN-14 is a novel cDNA of unknown function that hybridizes with a 4.5 kb mRNA that is induced 4-fold in NIH3T3 mouse cells following treatment with FGF-4. The induction of FIN-14 occurs late (18 hr) after treatment with FGF-4 and does not occur when cells are treated for 18 hr with FGF-4 in the presence of cycloheximide (44). These results confirm that FIN-14 encodes a late-inducible gene. Moreover, nuclear run-on assays document that FIN-14 is trancriptionally activated in NIH3T3 cells following growth factor stimulation. Tissue distribution studies indicate expression of a single mRNA species in the kidney with low levels of expression observed in several other tissues including testis and thymus. Mouse embryogenesis studies indicate that FIN-14 expression occurs constitutively in mouse embryos between day 10.5 and 15.5. Unlike NIH3T3, FIN-14 was constitutively expressed in PC12 cells and its level did not vary appreciably in response to growth factor stimulation. The role of PEGen 21/FIN-14 in progression in E11/E11-NMT model system is not currently known.

The PSGen cDNAs, PSGen-12 and PSGen-13, consist of sequences without homology to those presently reported in various DNA databases. Expression of these cDNAs is ~3- to 4-fold higher in E11 versus E11-NMT cells (FIG. 3). It is not currently known whether these genes simply correlate with or functionally regulate the progression phenotype. The identification of full-length cDNAs for PSGen-12 and PSGen-13 are in progress and once identified experiments can be conducted to directly define the role of these PSGen's in cancer progression.

We presently demonstrate that a modified differential RNA display technique, RSDD, can efficiently identify differentially expressed cDNAs. As predicted, subtractive hybridization prior to differential RNA display greatly reduces band complexity, a problem encountered in standard DDRT-PCR in which RNA samples are directly analyzed without subtraction. Unlike a previous report using subtracted cDNAs processed through successive rounds of PCR (32,45), common bands were eliminated using reciprocally subtracted cDNA libraries that had not been processed using PCR. In addition to subtraction hybridization, the discovery of differentially expressed genes was further streamlined by using reverse Northern analyses with isolated cDNAs. With 3 single anchored oligo dT primers and 18 arbitrary 5' primers, 72 bands were identified that displayed differential expression using reverse Northern analysis. Currently, 40 of these cDNA species have been analyzed by Northern blotting and found to display differential expression in E11 versus E11-NMT cells. Subsequent studies with the majority of these RSDD cDNAs demonstrated coordinated expression with the progression phenotype in a large panel of unprogressed and progressed transformed cells. Current sequence analysis of the cloned cDNA fragments revealed 9 different genes, including 4 novel genes not reported in recent DNA databases. RSDD represents a method of choice either as a more efficient and less time consuming modification of the differential RNA display strategy or as a screening methodology for identifying differentially expressed genes in reciprocally subtracted cDNA libraries.

References for the First Series of Experiments

1. Fisher, P. B. (Ed.) Mechanisms of Differentiation: Model Cell Culture Systems for Studying Differentiation. Vol. 1, pp. 1–164. Boca Raton, Fla.: CRC Press, Inc., 1990.
2. Fisher, P. B. (Ed.) Mechanisms of Differentiation: Modulation of Differentiation by Exogenous Agents. Vol. 2, pp. 1–205. Boca Raton, Fla.: CRC Press, Inc., 1990.
3. Watson, J. B. and Margulies, J. E. Differential CDNA screening strategies to identify novel stage-specific proteins in the developing mammalian brain. Developmental Neuroscience 15: 77–86, 1993.
4. Winkles, J. A. Serum- and polypeptide growth factor-inducible gene expression in mouse fibroblasts, Prog. Nucl. Acid Res. & Mol. Biol. 58:41–78, 1998.
5. Jiang, H. and Fisher, P. B. Use of a sensitive and efficient subtraction hybridization protocol for the identification of genes differentially regulated during the induction of differentiation in human melanoma cells. Mol. Cell. Different. 1: 285–299, 1993.
6. Jiang, H., Lin, J. J., Su, Z. Z., Goldstein, N. I., and Fisher, P. B. Subtraction hybridization identifies a novel melanoma differentiation associated gene, mda 7, modulated during human melanoma differentiation, growth and progression. Oncogene 11: 2477–2486, 1995.
7. Jiang, H., Lin, J., Su, Z. Z., Herlyn, M., Kerbel, R. S., Weissman, B. E., Welch, D. R., and Fisher, P. B. The melanoma differentiation-associated gene melanoma cells. Oncogene 10. 1855–1864, 1995.
8. Jiang, H., Su, Z. Z., Lin, J. J., Goldstein, N. I., Young, C. S., and Fisher, P. B. The melanoma differentiation associated gene mda-7 suppresses cancer cell growth. Proc. Nati. Acad. Sci. USA 93. 9160–9165, 1996.
9. Sagerstrom, C. G., Sun, B. I., and Sive, H. L. Subtractive cloning: past, present, and future. Annu. Rev. Biochem. 66. 751–783,1997.
10. Su, Z.-z., Shi, Y., and Fisher, P. B. Subtraction hybridization identifies a transformation progression-associated gene PEG-3 with sequence homology to a growth arrest and DNA damage-inducible gene, Proc. Natl. Acad. Sci. USA 94:9125–9130, 1997.
11. Liang, P. and Pardee, A. B. Differential display of eukaryotic messenger RNA by means of the polymerase chain reaction. Science 257. 967–971, 1992.
12. Shen, R., Su, Z. Z., Olsson, C. A., and Fisher, P. B. Identification of the human prostatic carcinoma oncogene PTI-1 by rapid expression cloning and differential RNA display. Proc. Natl. Acad. Sci. USA 92:6778–6782, 1995.
13. Ralph, D., McClelland, M., and Welsh, J. RNA fingerprinting using arbitrarily primed PCR identifies differentially regulated RNAs in mink lung (Mv1 Lu) cells growth arrested by transforming growth factor beta 1. Proc. Nat. Acad. Sci. USA 90:10710–10714, 1993.

14. McClelland, M. and Welsh, J. RNA fingerprinting by arbitrarily primed PCR, PCR Methods & Applications 4: S66–81, 1994.
15. Hubank, M. and Schatz, D. G. Identifying differences in mRNA expression by representational difference analysis of cDNA. Nucl. Acids Res. 22: 5640–5648, 1994.
16. Velculescu, V. E., Zhang, L., Vogelstein, B., and Kinzler, K. W. Serial analysis of gene expression. Science 270. 484–487, 1995.
17. Zhang, L., Zhou, W., Velculescu, V. E., Kern, S. E., Hruban, R. H., Hamilton, S. R., Vogelstein, B., and Kinzler, K. W. Gene expression profiles in normal and cancer cells. Science 276:1268–1272, 1997.
18. Wan, J. S., Sharp, S. J., Poirier, G. M.-C., Wagaman, P. C., Chambers, J., Pyati, J., Hom, Y.-L, Galindo, J. E., Huvar, A., Peterson, P. A., Jackson, M. R., and Erlander, M. G. Cloning differentially expressed mRNAs. Nature Biotechnology 14:1685–1691, 1996.
19. Adams, M. D., Kerlavage, A. R., Fields, C., and Venter, J. C. 3,400 new expressed sequence tags identify diversity of transcripts in human brain. Nature Genetics 4: 256–267, 1993.
20. Schena, M., Shalon, D., Davis, R. W., and Brown, P. O. Quantitative monitoring of gene expression patterns with a complementary DNA microarray. Science 270: 467–470, 1995.
21. Liang, P. and Pardee, A. B. Differential display. A general protocol. Meth. Mol. Biol. 85. 3–11, 1997.
22. Liang, P. and Pardee, A. B. Recent advances in differential display. Curr. Opinion Immunol. 7. 274–280, 1995.
23. Debouck, C. Differential display or differential dismay. Curr. Opinion Biotechnology 6: 597–599, 1995.
24. Liang, P., Averboukh, L., and Pardee, A. B. Distribution and cloning of eukaryotic mRNAs by means of differential display: refinements and optimization. Nucl. Acids Res. 21: 3269–3275, 1993.
25. Liang, P., Zhu, W., Zhang, X., Guo, Z., O'Connell, R. P., Averboukh, L, Wang, F., and Pardee, A. B. Differential display using one-base anchored oligo dT primers. Nucl. Acids Res. 22:5763–5764, 1994.
26. Zhao, S., Ooi, S. L., and Pardee, A. B. New primer strategy improves precision of differential display. Biotechniques 18: 842–846, 848, 850, 1995.
27. Rohrwild, M., Alpan, R. S., Liang, P., and Pardee, A. B. Inosine-containing primers for mRNA differential display. Trends in Genetics 11: 300, 1995.
28. Averboukh, L., Douglas, S. A., Zhao, S., Lowe, K., Maher, J., and Pardee, A. B. Better gel resolution and longer cDNAs increase the precision of differential display. Biotechniques 20: 918–921, 1996.
29. Rangnekar, V. V., Waheed, S., and Rangnekar, V. M. Interleukin-1 inducible tumor growth arrest is characterized by activation of cell type-specific Hearlyn gene expression programs. J. Biol. Chem. 267: 6240–6248, 1992.
30. Maser, R. L. and Calvet, J. P. Analysis of differential gene expression in the kidney by differential cDNA screening, subtractive cloning, and mRNA differential display. Seminars in Nephrology 15. 29–42, 1995.
31. Wong, B., Park, C. G., and Choi, Y. Identifying the molecular control of T-cell death; on the hunt for killer genes. Semin. Immunol. 9: 7–16, 1997.
32. Hakvoort, T. B., Leegwater, A. C., Michiels, F. A., Chamuleau, R. A., and Lamers, W. H. Identification of enriched sequences from a cDNA subtraction-hybridization procedure. Nucl. Acids Res. 22: 878–879, 1994.
33. Babiss, L. E., Zimmer, S. G., and Fisher, P. B. Reversibility of progression of the transformed phenotype in Ad5-transformed rat embryo cells. Science 228. 1099–1101, 1985.
34. Reddy, P. G., Su, Z.-z., and Fisher, P. B. Identification and cloning of genes involved in progression of transformed phenotype. In: K. W. Adolph (ed.) In: Chromosome and Genetic Analysis, Methods in Molecular Genetics, Vol. 1, pp. 68–102. Orlando, Fla.: Academic Press, Inc., 1993.
35. Zhang, H., Zhang, R., and Liang, P. Differential screening of differential display cDNA products by reverse northern. Meth. Mol. Biol. 85-87–93, 1997.
36. Zhao, S., Ooi, S. L., Yang, F. C., and Pardee, A. B. Three methods for identification of true positive cloned cDNA fragment in differential display. Biotechniques 20: 400–404, 1996.
37. Liang, P., Bauer, D., Averboukh, L., Warthoe, P., Rohrwild, M., Muller, H., Strauss, M., and Pardee, A. B. Analysis of altered gene expression by differential display. Meth. Enzymol. 254:304–321, 1995.
38. Wang, Z. and Brown, D. D. A gene expression screen. Proc. Nati. Acad. Sci. USA 88. 11505–11509, 1991.
39. Zhang, H., Zhang, R., and Liang, P. Differential screening of gene expression difference enriched by differential display. Nucl, Acids Res. 24: 2454–2455, 1996.
40. Mathieu-Daude, F., Cheng, R., Welsh, J., and McClelland, M. Screening of differentially amplified cDNA products from RNA arbitrarily primed PCR fingerprints using single strand conformation polymorphism (SSCP) gels. Nucl. Acids Res. 24: 1504–1507, 1996.
41. Yasugi, T., Vidal, M., Saka, H., Howley, P. M., and Benson, J. D. Two classes of human papillomavirus type 16 E1 mutants suggest pleiotropic conformational constraints affecting E1 multimerization, E2 interaction, and interaction with cellular proteins. J. Virol. 71: 5941–5951, 1997.
42. Gekakis, N., Johnson, R. C., Jerkins, A., Mains, R. E., and Sul, H. S. Structure, distribution, and functional expression of the phosphofructokinase C isozyme. J. Biol. Chem. 269. 3348–3355, 1994.
43. Sanchez-Martinez, C. and Aragon, J. J. Analysis of phosphofructokinase subunits and isozymes in ascites tumor cells and its original tissue, murine mammary gland. FEBS Letters 409. 86–90, 1997.
44. Guthridge, M. A., Seldin, M., and Basilico, C. Induction of expression of growth-related genes by FGF-4 in mouse fibroblasts. Oncogene 12:1267–1278, 1997.
45. Wu, C. G., Hakvoort, T. B., Lamers, W. H., and Chamuleau, R. A. Isolation of up- and down-regulated cDNAs associated with hepatocellular carcinoma by a subtraction-enhanced display technique. Biochim. Biophys. Acta. 1315. 169–175, 1996.

Second Series of Experiments

Presently described is a RSDD approach that efficiently and consistently reduces the complexity of DDRT-PCR and results in the identification and cloning of genes displaying anticipated differential expression. The model used for RSDD was an adenovirus-transformed rat embryo cell line, E11, that acquires an aggressive oncogenic progression phenotype when injected into athymic nude mice and reestablished in cell culture (E11-NMT) (6,26,27). Injection of E11 cells into nude mice results in tumors in 100% of animals with a tumor latency time of approximately 35 to 40 days, whereas E11-NMT cells form tumors in 100% of nude mice with a tumor latency time of 15 to 20 days (6,26,27). Additionally, E11 cells form colonies in agar with an efficiency of ~3%, whereas E11-NMT display an agar cloning efficiency of >30% (6,26,27). The increased tumorigenicity and enhanced anchorage independence phenotypes are key indicators of tumor progression in the E11/E11-NMT model system (6,26,27). RSDD has resulted in the identification and cloning of genes displaying elevated expression in progressed tumor cells (progression elevated gene, PEGen) and suppressed expression in progressed tumor cells (progression suppressed gene, PSGen).

Materials and Methods

RNA isolation and cDNA library construction. Total RNA from E11 and E11-NMT cells was isolated by the guanidinium isothiocyanate/CsCl centrifugation procedure and poly(A)+ RNA was purified with oligo(dT) cellulose chromatography(S). Two λ-ZAP cDNA libraries from E11 and E11-NMT mRNAs were constructed with λ-ZAP cDNA library kits (Stratagene) following the manufacturer's protocol. Reciprocal subtraction between E11 and E11-NMT libraries was performed and two subtracted cDNA libraries (E11 minus E11-NMT and E11-NMT minus E11) were constructed as described (5,6). Plasmid cDNA libraries from the subtracted λ-ZAP cDNA libraries were obtained by in vivo excision following the manufacturer's protocol (Stratagene) and the plasmids were isolated with Qiagen columns (Qiagen, Chatsworth, Calif.).

RSDD methodology. The purified plasmids of reciprocally subtracted cDNA libraries were directly subjected to differential display as in Liang et al. (28) with minor modifications. The plasmids of reciprocally subtracted cDNA libraries were PCR-amplified with the combination of three single-anchor 3' primers ($T_{13}A$, $T_{13}C$ or $T_{13}G$) and 18 arbitrary 5' 10-mer primers obtained from Operon Technology Inc. (Alameda, Calif. OPA 1–20 except OPA1 and 3). The 20 μl PCR reaction consisted of 10 mM Tris-HCl (pH 8.4), 50 mM KCl, 1.5 mM $MgCl_2$, 2 μM each dNTP, 0.2 μM 5' arbitrary primer, 1 μM 3' anchor primer, 50 ng of plasmid of a subtracted library, 10 μCi α-$^{35}$S-DATP (3,000 Ci/mmol from Amersham) and 1 unit of Taq DNA polymerase (Gibco/BRL). The parameters of PCR were 30 sec at 95° C., 40 cycles of 30 sec at 95° C., 2 min at 40° C. and 30 sec at 72° C. and additional 5 min. at 72° C. After the cycling, 10 μl of 95% formamide, 0.05% bromophenol blue and 0.05% xylene cyanol were added to each PCR reaction. The mixture was heated at 95° C. for 2 min and separated in a 5% denaturing DNA sequencing gel maintained at 50° C. PCR reactions of plasmids from each subtracted library in a primer set were run side by side. Differentially amplified bands from plasmids of each subtracted library were marked with 18 G needle through the film and cut out with a razor. The gel slice was put in 100 μl TE (pH 8.0) and incubated at 4° C. overnight. After the incubation, the mixture was boiled for 5 min and microcentrifuged for two min. The supernatant was collected and stored at −20° C. until reamplification. The band extract was reamplified with the same cycling parameters in a 50 μl reaction consisting of 10 mM Tris-HCl (pH 8.4), 50 mM KCl, 1.5 mM $MgCl_2$, 20 μM each dNTP, 0.2 μM 5' arbitrary primer, 1 μM 3' anchor primer, 5 μl of band extract and 2.5 units of Taq DNA polymerase (Gibco/BRL).

Reverse Northern Blotting Procedure. Differential expression of the reamplified DNA fragment was scrutinized by reverse Northern and Northern blot analyses. In reverse Northern analysis, after confirmation in a 1% agarose gel, the reamplified DNA fragment (10 μl of PCR reaction) was mixed with 90 μl TE and spotted on a positively charged Nylon membrane (Boehringer Mannheim) with a 96-well vacuum manifold. The membrane was soaked with denaturing and neutralizing solution successively, and the spotted DNA was crosslinked to the membrane with a UV crosslinker (Stratagene). $^{32}$P-labeled first strand cDNA was prepared by reverse transcription of total RNA. After heating at 70° C. for 10 min and quenching on ice for two min, 0.4 μM each $T_{13}A$, $T_{13}G$ and $T_{13}C$ and 10 μg total RNA mixture was added with 50 mM Tris-HCl, (pH 8.3), 75 mM KCl, 3 mM $MgCl_2$, 10 mM DTT, 0.5 mM DATP, 0.5 mM dGTP, 0.5 mM dTTP, 0.02 mM dCTP, 0.5 μl RNase inhibitor (Gibco/BRL), 100 μCi dCTP (3,000 Ci/mmol from Amersham) and 200 units Superscript RT II (Gibco/BRL) in a final 25 μl reaction. The reaction mixture was incubated at 42° C. for one hour and at 37° C. for 30 min after addition of 2 μl of RNase H (10 units, Gibco/BRL). The membrane was hybridized at 42° C. overnight in a 50% formamide hybridization solution. The hybridized membrane was washed at room temperature for 15 min with 2×standard saline citrate containing 0.1% SDS twice and at 55° C. for at least one hour with 0.1×Standard Saline Citrate containing 0.1% SDS, successively. The membrane was probed with the $^{32}$P-labeled cDNA of E11, striped off and probed with $^{32}$P-labeled cDNA of E11-NMT. The signal intensity of each spot was normalized against that of glyceraldehyde-3-phosphate dehydrogenase and compared between E11 and E11-NMT. Reamplified DNA fragments displaying differential expression levels ≧1.8-fold higher between the two cell types were selected and analyzed by Northern bloting analysis.

Northern Blotting Analysis. In Northern blot analysis, 10 μg of total RNA from E11 and E11-NMT cells were run side-by-side in a 1% agarose gel with formaldehyde and transferred to a positively charged Nylon membrane. Reamplification reaction (5 μl) was $^{32}$P-labeled with a multiprime labeling kit (Boehringer Mannheim) used to probe the membrane as described above. DNA fragments expressed differentially between E11 and E11-NMT in Northern blot analyses were cloned into the EcoRV site of the pZEro-2.1 cloning vector (Invitrogene) and sequenced.

To confirm differential expression, the cloned cDNA fragment was released by EcoRI-XhoI, $^{32}$P-labeled and used to probe Northern blots as described above. Samples of RNAs from various E11 and E11-NMT derivatives displaying either a progressed or suppressed progression phenotype, based on nude mice tumorigenesis and soft agar cloning assays were analyzed. These included E11, E11-NMT, CREF×E11-NMT F1 and F2 somatic cell hybrids (suppressed progression phenotype), CREF×E11-NMT R1 and R2 somatic cell hybrids (progression phenotype), E11× E11-NMT A6 somatic cell hybrid (suppressed progression phenotype), E11×E11-NMT A6TD tumor-derived somatic cell hybrid (progression phenotype), E11×E11-NMT 3b somatic cell hybrid (suppressed progression phenotype), E11×E11-NMT IIa (progression phenotype), E11-NMT AZA B1 and C1 5-azacytidine treated E11-NMT clones (suppressed progression phenotype), E11-Ras R12 clone containing the Ha-ras oncogene (progression phenotype) and E11-HPV E6/E7 clone containing the human papilloma virus-18 E6 and E7 gene region (progression phenotype). Differential expression of the PEGen and PSGen genes in the various cell types was confirmed using $^{32}$P-labeled probes and northern hybridization analysis. After reconfirmation of differential expression, the plasmids containing the differentially expressed DNA fragments were sequenced by the dideoxy sequencing procedure.

Results and Discussion

Subtraction hybridization provides a direct means of enriching for unique cDNA species and eliminating common sequences between complex genomes (7,18). DDRT-PCR is a proven methodology for the rapid identification and cloning of differentially expressed sequences between cell types (1,2,28). In principle, subtraction hybridization combined with DDRT-PCR should reduce band complexity which often obscures the identification of differentially expressed genes and generates false positive signals (21,29). RSDD has been used to analyze genes differentially expressed during transformation progression (FIG. 28). Differential RNA display was directly performed with reciprocally subtracted cDNA plasmid libraries (E11 minus E11-NMT and E11-NMT minus E11) that had not been subjected to PCR. Three single anchored oligo dT 3' primers were used for subsequent amplification prior to display. To further streamline the DDRT-PCR procedure, reamplified cDNAs identified using RSDD were analyzed using the reverse Northern blotting procedure (30,31). cDNAs displaying differential expression by reverse Northern blotting were subsequently confirmed for true differential expression by Northern analysis.

The differential RNA display pattern of E11 and E11-NMT cells using standard differential RNA display (DDRT-PCR) and RSDD is shown in FIG. 1 (Left Panel). The differential RNA display pattern of RSDD is much less complex than that of DDRT-PCR. These experiments demonstrate that subtractive hybridization prior to differential RNA display is effective in simplifying display patterns permitting the efficient identification of differentially expressed cDNAs. Since RSDD significantly reduced the number of bands displayed, single anchor oligo dT primers, that can increase band numbers, were successfully used in subsequent applications of the RSDD approach (FIG. 1; Right Panel). Using RSDD, 234 differentially displayed cDNAs in the E11/E11-NMT tumor progression model system were isolated. Hakvoort et al. (25) used a reciprocal subtraction approach to analyze gene expression changes resulting during liver regeneration following 70% hepatectomy, i.e., normal liver subtracted from partially hepatectomized regenerating liver and vice versa. Although some bands displayed apparent enrichment, the complexity of the display pattern did not show appreciable simplification. In contrast, RSDD results in a clearer delineation and simplification of differentially expressed amplified bands (FIG. 1). Although conceptually similar, RSDD is significantly more effective than the subtraction plus DDRT-PCR approach described by Hakvoort et al. (25) The reasons for the improved efficiency of RSDD versus the Hakvoort et al. (25) approach are not known. One possibility is that the differences between the experimental approaches may reflect the subtraction hybridization strategies employed. The approach of Hakvoort et al. (25) is based on the subtraction procedure described by Wang and Brown (32). This approach uses multiple rounds of PCR-amplification prior to each round of subtractive hybridization. In contrast, RSDD involves a single round of reciprocal subtraction without intermediate amplification (5,6). In this respect, the complicated display pattern observed by Hakvoort et al. (25) even after three or four rounds of subtraction might result from reduced subtraction efficiency, PCR artifacts or a combination of these problems. Increasing the number of reactions by using two-base pair anchored oligo dT primers did not reduce the complexity of displayed bands (25). In these contexts, a critical component for the successful use of RSDD involves the use of an appropriate subtraction hybridization protocol, which can efficiently reduce cDNA complexity and generate stable populations of cDNAs for analysis.

Previous studies demonstrate that different gene cloning strategies, including DDRT-PCR, subtraction hybridization and electronic display, identify distinct subsets of differentially expressed genes (18). These results suggest that a single approach for gene identification may not identify the complete spectrum of differentially expressed genes. Similarly, RSDD and DDRT-PCR do not resolve the same differentially expressed bands (FIG. 1). Unique bands identified in DDRT-PCR that were differentially expressed when analyzed by Northern blotting were not the same as those found using RSDD and vise versa (data not shown). These results are not surprising, since, as indicated above, subtraction hybridization and differential RNA display identified distinct differentially expressed genes (18). Apparently, specific differentially expressed genes are lost during subtraction hybridization and differential RNA display of subtracted cDNAs. On the basis of these considerations, it will be essential to use multiple gene discovery approaches to identify and clone the complete spectrum of differentially expressed genes.

DDRT-PCR can generate large numbers of differentially displayed bands making subsequent analysis both labor intensive and a daunting challenge. In order to reduce these limitations of DDRT-PCR, RSDD has been used in combination with reverse Northern analyses of isolated cDNAs. Gel extracted cDNA fragments were reamplified, dot-blotted on Nylon membranes and successively probed with reverse transcribed $^{32}$P-cDNA from E11 or E11-NMT RNAs (FIG. 2). Signals were detected in 181 reamplified bands out of 234 (77%).

The signal intensities of the various cDNAs in reverse Northern analysis were quantified and normalized against that of GAPDH, which remained unchanged in E11 and E11-NMT cells. Progression elevated gene-3 (PEG-3) (6) was used as an additional control, to verify increased expression in E11-NMT versus E11 cells. In the reverse Northern analyses, PEG-3 levels were 4-fold higher in E11-NMT than in E11 cells, which coincided with Northern blotting results, thereby demonstrating the concordance of reverse Northern and Northern assays. A $\geq$1.8-fold differential cut-off (after normalization for GAPDH expression) was used to identify and isolate cDNA bands displaying modified expression in E11 versus E11-NMT cells. This resulted in the identification of 7 cDNAs with higher expression in E11 versus E11-NMT cells and 65 cDNAs with elevated expression in E11-NMT versus E11 cells. These results suggest that tumor progression in E11-NMT cells correlates with increased expression of a large number of genes, whereas only a smaller subset of genes display decreased expression.

A problem frequently encountered in DDRT-PCR, that is reduced but still can occur in RSDD, is the isolation of multiple cDNA species from what appears to be a single amplified band. When this occurs, these multiple species can produce spurious results when analyzed by reverse Northern analyses. For example, if two distinct species are isolated, one displaying modified expression and a second not displaying modified expression, an accurate estimate of differential expression will not be obtained by reverse Northern analysis. In this case, a number of potential false positives generated using reverse Northern analyses, may in reality not be false positives, but instead may represent multiple cDNAs. By performing single strand conformational polymorphism (SSCP) or reverse Northern analyses using cloned cDNA populations (33,34) this problem can be ameliorated.

The expression pattern of representative RSDD-derived cDNAs in E11 versus E11-NMT and in a more expanded E11/E11-NMT progression cell culture series is shown in FIGS. 29 and 30, respectively. Reverse Northern results correlated well with Northern blots using E11 and E11-NMT (~75% concordance) or a larger panel of cells differentially displaying the progression phenotype, including progression negative E11, CREFxE11-NMT F1 and F2, E11xE11-NMT A6, E11xE11-NMT 3b, E11-NMT Aza B1 and Aza C1 cells, and progression positive E11-NMT, CREFxE1-NMT R1 and R2, E11xE11-NMT A6TD, E11xE11-NMT IIa, E11-Ras R12 and E11-HPV E6/E7 cells. Sequence analysis of the various PEGen cDNAs identified both unknown and known genes (Table 3). Five of 10 PEGen cDNAs (50%) were classified as novel sequences since no matches were found in current DNA databases. Novel PEGen cDNAs include, PEGen 13, 14, 24, 28 and 32. Known PEGen genes included PEGen 7 (human papilloma virus-16 early region 1 binding protein; HPV16 E1BP), PEGen 8 (phosphofructokinase kinase C; PFK-C), PEGen 21 (a fibroblast growth factor-4 inducible gene; FIN 14), PEGen 26 (poly ADP-ribose polymerase) and PEGen 30 (rat esp1 homology). In the case of the PSGen cDNAs, six of six (100%) were novel, including PSGen 12, 13, 26, 27, 28 and 29 (Table 3).

TABLE 3

PEGen and PSGen genes isolated using RSDD

| Nomenclature[a] | Identity[b] | Homology (%)[c] |
|---|---|---|
| PEGen 7 | Human HPV16 E1BP | 90 |
| PEGen 8 | Rat phospho-fructokinase C (PFK-C) | 100 |
| PEGen 13 | Unknown | Novel |
| PEGen 14 | Unknown | Novel |
| PEGen 21 | Murine FIN 14 | 94 |
| PEGen 24 | Unknown | Novel |
| PEGen 26 | Rat poly ADP-ribose polymerase | 100 |
| PEGen 28 | Unknown | Novel |
| PEGen 30 | Rat esp1 | 98 |
| PEGen 32 | Novel | Novel |
| PSGen 12 | Unknown | Novel |
| PSGen 13 | Unknown | Novel |
| PSGen 26 | Unknown | Novel |
| PSGen 27 | Unknown | Novel |
| PSGen 28 | Unknown | Novel |
| PSGen 29 | Unknown | Novel |

[a]PEGen are progression elevated genes that display elevated expression in E11-NMT versus E11 cells. PSGen are progression suppressed genes that display elevated expression in E11 versus E11-NMT cells.
[b]Sequences have compared with reported genes in various DNA data bases (including GenBank and EMBL) and identification with known genes are indicated. Genes without homology to currently reported genes are indicated as unknown.
[c]percentage homology with known sequences, either human, rat or mouse is indicated.
Where no homology exists the cDNA is considered novel.

PEGen 7 is expressed at ~4-fold higher levels in E11-NMT than in E11 cells. PEGen 7 is ~98% homologous to 16E1-BP, a CDNA encoding a protein identified using the yeast two-hybrid assay that interacts with human papillomavirus type 16 E1 protein (35). 16E1-BP encodes a 432aa protein of unknown function but does contain an ATPase signature motif (Gly-X4-Gly consensus ATP binding motif at aa 179 through 186). 16E1-BP appears to be a form of TRIP13, a protein previously shown to bind thyroid hormone receptor in yeast two-hybrid assays. The role of PEGen 7/16E1-BP in the progression phenotype in the E11/E11-NMT progression model is not known. Additional studies are necessary to determine if this gene change is associative or causative of transformation progression.

PEGen 8 is expressed at ~3- to 4-fold higher levels in E11-NMT than in E11 cells. PEGen 8 shows 100% homology to rat phosphofructokinase C (PFK-C)(36). PFK catalyzes the rate-limiting and committed step in glycolysis, the conversion of fructose 6-phosphate to fructose 1,6-biphosphate. Three subunit isozymes of PFK have been identified, that form homo- and heterotetramers with differing catalytic and allosteric properties. PFK-M is specific for cardiac and skeletal muscle, PFK-L is expressed in many tissues but is most abundant in the liver and PFK-C is expressed in several brain regions and the anterior pituitary but not in liver, skeletal muscle, or several other human tissues. The cDNA of PFK-C isolated from a rat hypothalamic cDNA library is 2643 bp and encodes a protein of 765aa (~36). In a recent study Sanchez-Martinez and Aragon (37), demonstrated that PFK-C is the predominant form of PFK in ascites tumor cells (obtained from a transplantable mouse carcinoma of mammary origin), whereas PFK-L is most abundant in the normal mammary gland. These results suggest the interesting possibility that PFK-C might contribute to the malignant nature of specific target cells. The role presently reported of PEGen 8/PFK-C in progression in the E11/E11-NMT model remains to be determined.

PEGen 21 is expressed at ~3- to 4-fold higher levels in E11-NMT than in E11 cells. PEGen 21 displays ~98% homology with the fibroblast growth factor-4 inducible gene FIN-14 (38). FIN-14 is a novel cDNA of unknown function that hybridizes with a 4.5 kb mRNA that is induced 4-fold in NIH 3T3 mouse cells following treatment with FGF-4. The induction of FIN-14 occurs late (18 hr) after treatment with FGF-4 and does not occur when cells are treated for 18 hr with FGF-4 in the presence of cycloheximide (38). These results confirm that FIN-14 encodes a late-inducible gene. Moreover, nuclear run-on assays document that FIN-14 is transcriptionally activated in NIH 3T3 cells following growth factor stimulation. Tissue distribution studies indicate expression of a single mRNA species in the kidney with low levels of expression observed in several other tissues including testis and thymus. Mouse embryogenesis studies indicate that FIN-14 expression occurs constitutively in mouse embryos between day 10.5 and 15.5. Unlike NIH 3T3, FIN-14 was constitutively expressed in PC12 cells and its level did not vary appreciably in response to growth factor stimulation. The role of PEGen 21/FIN-14 in progression in E11/E11-NMT model system is not currently known.

PEGen 26 is expressed at ~3- to 4-fold higher levels in E11-NMT than in E11 cells. This cDNA is identical to rat poly(ADP-ribose) polymerase (PARP)(39). PARP contributes to the ability of eukaryotic cells to contend with both environmental and endogenous genotoxic agents (40). PARP is a nuclear enzyme that binds to DNA breaks and then catalyzes the covalent modification of acceptor proteins with poly(ADP-ribose) (39,40). PARP activity contributes to the recovery of proliferating cells from DNA damage and to the maintenance of genomic stability, which may be regulated by effects on chromatin structure, DNA base-excision repair and cell cycle regulation (39,40). The role of PEGen 26/PARP in mediating the progression phenotype is not currently known. However, since cancer is a progressive disease characterized by the accumulation of genetic alterations in the evolving tumor (6), it is tempting to speculate that overexpression of PEGen 26/PARP in E11-NMT may facilitate the ability of these aggressive cancer cells to maintain genomic stability during cancer progression. In this context, PEGen 26/PARP may be an integral component of progression. This hypothesis is readily testable. PEGen 30 is expressed at 2- to 3-fold higher levels in E11-NMT than in E11 cells. This cDNA displays ~98.5% homology to rat esp1

(41). Rat esp1 encodes a 24-kDa nuclear protein which is the rat homologue of Drosophila Enhancer of split., a gene involved in ventral ectodermal development in Drosophila (41). PEGen 30 appears to be a homologue of esp1, since the message detected in E11 and E11-NMT cells (~4 kb) is larger in size than the reported esp1 transcript (1.3 kb) (41). The role of PEGen 30/esp1 in tumor progression in E11/E11-NMT model system remains to be determined.

The PSGen cDNAs, 12, 13, 26, 27, 28 and 29, consist of sequences without homology to those in various DNA data bases. Expression of PSGen 12 and PSGen 13 cDNAs is ~3- to 4-fold higher in E11 versus E1-NMT cells (FIG. 29). It is not currently known whether these genes simply correlate with or functionally regulate the progression phenotype. The identification of full-length cDNAs for PSGen-12 and PSGen-13, as well as the other novel PSGen and PEGen cDNAs, are in progress and once isolated experiments can be conducted to directly define the role of these progression-related genes in cancer progression.

Presently demonstrated is a modified gene-identification and gene-cloning technique, RSDD, that can efficiently identify differentially expressed cDNAs. As predicted, subtractive hybridization prior to differential RNA display greatly reduces band complexity, a problem encountered in standard DDRT-PCR in which RNA samples are directly analyzed without subtraction. Unlike a previous report using subtracted cDNAs processed through successive rounds of PCR (25,42), common bands were eliminated using reciprocally subtracted cDNA libraries that had not been processed using PCR. In addition to subtraction hybridization, the discovery of differentially expressed genes was further streamlined by using reverse Northern analyses with isolated cDNAs. With 3 single anchored oligo dT primers and 18 arbitrary 5' primers, 72 bands were identified that displayed differential expression using reverse Northern analysis. Currently, 38 cDNA species have been analyzed by Northern blotting and 31 (~82%) displayed differential expression in E11 versus E11-NMT cells. Sequence analysis of the cloned cDNA fragments revealed 16 different genes, including 11 novel genes not reported in recent DNA databases. RSDD represents a method of choice either as a more efficient and less time consuming modification of the differential RNA display strategy or as a screening methodology for identifying differentially expressed genes in reciprocally subtracted cDNA libraries. Moreover, the ability of RSDD to identify differentially expressed genes that are dissimilar to those recognized using standard DDRT-PCR or subtraction hybridization indicates that this approach will be a valuable adjunct in cloning the complete repertoire of differentially expressed gene changes occurring between complex genomes.

References for Second Series of Experiments

1. Watson, J. B. and Margulies, J. E. (1993) Develop. Neurosci., 15, 77–86.
2. Winkles, J. A. (1998) Prog. Nucleic Acid Res. & Mol. Biol., 58, 41–78.
3. Fisher, P. B. (ed.) (1990) Model Cell Culture Systems for Studying Differentiation. Vol. 1. Mechanisms of Differentiation. Edited by Fisher, P. B. CRC Press, Inc., Boca Raton, Fla.
4. Fisher, P. B. (ed.) (1990) Modulation of Differentiation by Exogenous Agents. Vol. 2. Mechanisms of Differentiation. Edited by Fisher, P. B. CRC Press, Inc., Boca Raton, Fla.
5. Jiang, H. and Fisher, P. B. (1993) Mol. Cell. Different., 1, 285–299.
6. Su, Z.-z., Shi, Y. and Fisher, P. B. (1997) Proc. Natl. Acad. Sci. USA, 94, 9125–30.
7. Sagerstr÷m, C. G., Sun, B. I. and Sive, H. L. (1997) Ann. Rev. Biochemistry, 66, 751–83.
8. Jiang, H., Lin, J., Su, Z. Z., Herlyn, M., Kerbel, R. S., Weissman, B. E., Welch, D. R. and Fisher, P. B. (1995) Oncogene, 10, 1855–64.
9. Jiang, H., Lin, J. J., Su, Z. Z., Goldstein, N. I. and Fisher, P. B. (1995) Oncogene, 11, 2477–86.
10. Jiang, H., Su, Z. Z., Lin, J. J., Goldstein, N. I., Young, C. S. and Fisher, P. B. (1996) Proc. Natl. Acad. Sci. USA, 93, 9160–5.
11. Liang, P. and Pardee, A. B. (1992) Science, 257, 967–971.
12. Shen, R., Su, Z. Z., Olsson, C. A. and Fisher, P. B. (1995) Proc. Natl. Acad. Sci. USA, 92, 6778–82.
13. McClelland, M., Mathieu-Daude, F. and Welsh, J. (1995) Trends in Genetics, 11(6), 242–6.
14. Ralph, D., McClelland, M. and Welsh, J. (1993) Proc. Natl. Acad. Sci. USA,, 90, 10710–4.
15. Hubank, M. and Schatz, D. G. (1994) Nucleic Acids Res., 22, 5640–8.
16. Velculescu, V. E., Zhang, L., Vogelstein, B. and Kinzler, K. W. (1995) Science, 270, 484–7.
17. Zhang, L., Zhou, W., Velculescu, V. E., Kern, S. E., Hruban, R. H., Hamilton, S. R., Vogelstein, B. and Kinzler, K. W. (1997) Science, 276, 1268–72.
18. Wan, J. S., Sharp, S. J., Poirier, G. M.-C., Wagaman, P. C., Chambers, J., Pyati, J., Hom, Y.-l., Galindo, J. E., Huvar, A., Peterson, P. A., Jackson, M. R. and Erlander, M. G. (1996) Nature Biotech., 14, 1685–91.
19. Adams, M. D., Kerlavage, A. R., Fields, C. and Venter, J. C. (1993) NatureGenetics, 4, 256–67.
20. Schena, M., Shalon, D., Davis, R. W. and Brown, P. O. (1995) Science, 270, 467–70.
21. Debouck, C. (1995) Cur. Opin Biotech., 6, 597–9;
22. Rangnekar, V. V., Waheed, S. and Rangnekar, V. M. (1992) J. Biol. Chem., 267, 6240–8.
23. Wong, B., Park, C. G. and Choi, Y. (1997) Sem Immunol., 9, 7–16.
24. Maser, R. L. and Calvet, J. P. (1995) Sem Nephrology, 15, 29–42.
25. Hakvoort, T. B., Leegwater, A. C., Michiels, F. A., Chamuleau, R. A. and Lamers, W. H. (1994) Nucleic Acids Res., 22, 878–9.
26. Reddy, P. G., Su, Z.-z. and Fisher, P. B. (1993) Identification and cloning of genes involved in progression of transformed phenotype. Vol. 1. In: Chromosome and Genetic Analysis, Methods in Molecular Genetics. Edited by Adolph, K. W. Academic Press, Inc., Orlando, Fla. pp.68–102.
27. Babiss, L. E., Zimmer, S. G. and Fisher, P. B. (1985) Science, 228, 1099–101.
28. Liang, P. and Pardee, A. B. (1995) Cur. Opin. Immunol., 7, 274–80.
29. Averboukh, L., Douglas, S. A., Zhao, S., Lowe, K., Maher, J. and Pardee, A. B. (1996) Biotechniques, 20, 918–21.
30. Zhang, H., Zhang, R. and Liang, P. (1997) Meth. Mol. Biol., 85, 87–93.
31. Zhao, S., Ooi, S. L., Yang, F. C. and Pardee, A. B. (1996) Biotechniques, 20, 400–4.
32. Wang, Z. and Brown, D. D. (1991) Proc. Natl. Acad. Sci. USA, 88, 11505–9.
33. Zhang, H., Zhang, R. and Liang, P. (1996) Nucleic Acids Res., 24(12), 2454–5.
34. Mathieu-Daude, F., Cheng, R., Welsh, J. and McClelland, M. (1996) Nucleic Acids Res., 24, 1504–7.

35. Yasugi, T., Vidal, M., Saka, H., Howley, P. M. and Benson, J. D. (1997) J. Virol., 71, 5941–51.
36. Gekakis, N., Johnson, R. C., Jerkins, A., Mains, R. E. and Sul, H. S. (1994) J. Biol. Chem., 269, 3348–3355.
37. Sanchez-Martinez, C. and Aragon, J. J. (1997) FEBS Letters, 409, 86–90.
38. Guthridge, M. A., Seldin, M. and Basilico, C. (1997) Oncogene, 12, 1267–78.
39. Beneke, S., Meyer, R. and Burkle, A. (1997) Biochem Mol. Biol. Intl., 43 (4), 755–61.
40. De Murcia, G. and de Murcia, J. M. (1994) TIBS, 19, 172–6.
41. Schmidt, C. J. and Sladek, T. E. (1993) J. Biol. Chem., 268, 25681–6.
42. Wu, C. G., Hakvoort, T. B., Lamers, W. H. and Chamuleau, R. A. (1996) Biochimica et Biophysica Acta, 1315, 169–75.
43. Liang, P., Bauer, D., Averboukh, L., Warthoe, P., Rohrwild, M., Muller, H., Strauss, M. and Pardee, A. B. (1995) Meth. Enzymol., 254, 304–21.

What is claimed is:

1. An isolated nucleic acid comprising the nucleic acid designation PEGen 28 (SEQ ID NO:10).

2. An isolated nucleic acid comprising a nucleic acid complementary to the nucleic acid designated PEGen 28 (SEQ ID NO:10).

3. The isolated nucleic acid of claim 2, wherein said nucleic acid complementary to the nucleic acid designated PEGen 28 (SEQ ID NO:10) is the nucleic acid of SEQ ID NO:28.

4. An isolated nucleic acid encoding a PEGen 28 polypeptide comprising the amino acid sequence of SEQ ID NO:29.

* * * * *

SEQUENCE LISTING

```
<160> NUMBER OF SEQ ID NOS: 42

<210> SEQ ID NO 1
<211> LENGTH: 371
<212> TYPE: DNA
<213> ORGANISM: homo sapiens
<220> FEATURE:
<221> NAME/KEY: unsure
<222> LOCATION: 5, 93, 153, 199, 217, 218, 221, 247, 259, 260, 274, 333,
      335, 358, 360
<223> OTHER INFORMATION: c, t, a or g
<221> NAME/KEY: misc_feature
<222> LOCATION: (1)...(371)
<223> OTHER INFORMATION: n = A,T,C or G

<400> SEQUENCE: 1
taaancggtg gtactgctgc acggtcctcc gggtactgga aagacatccc tttgtaaggc      60
attagcccag aaactgacca tcagactgtc aancaggtac cggtatggcc agttaattga     120
aataaacagc cacagcctat tttctaagtg gtnttcagaa agtggcaagt tggtaactaa     180
gatgttccag aagattcang acttgattga tgataannaa nctttggtgt ttgtcctgat     240
tgatgangta agcactcann ggtactcatt cttngtctgc attgcctctt gctattactg     300
cctgatccct ctcatttggt tcactgtgtc gcnanctctt ttctatggat cttttccnan     360
ccacccgttt c                                                          371

<210> SEQ ID NO 2
<211> LENGTH: 245
<212> TYPE: DNA
<213> ORGANISM: homo sapiens

<400> SEQUENCE: 2
gtgacgtagg gtctgttgcg tcaatggtta tagcaagtga tgctctctga ttattactgc      60
tgacaatact cggccaacaa ttcttgcata gagtgctgat aaataactat gttacaaaaa     120
ggggtggtcc ctggagaaca ttacaggctt ccctaggtaa gtgtgcaggt caggagacgg     180
catattcaat cagatggctg atagttctcc gtggttatgc accggctcca gcttgcctac     240
gtcac                                                                 245

<210> SEQ ID NO 3
<211> LENGTH: 178
<212> TYPE: DNA
<213> ORGANISM: homo sapiens
<220> FEATURE:
<221> NAME/KEY: unsure
<222> LOCATION: 140, 163
<223> OTHER INFORMATION: c, t, a or g
<221> NAME/KEY: misc_feature
<222> LOCATION: (1)...(178)
<223> OTHER INFORMATION: n = A,T,C or G
```

```
<400> SEQUENCE: 3
gcagcatgat gaatttaatg caacagtcat agcagggcaa ggggagagaa aggcagatgg      60
actatctgca tcatcaagcg agggcttgtg tcggcggcta tgtgcagaga cgagcagggc     120
gaggcactta aaagctgctn gatgaaaatc cacccaggag aantctgggc ctacgtca      178

<210> SEQ ID NO 4
<211> LENGTH: 191
<212> TYPE: DNA
<213> ORGANISM: homo sapiens

<400> SEQUENCE: 4
tgacgtaggc ccagacttct cctgggtgga ttttcatcca gcagctttta agtgcctcgc      60
cctgctcgtc tctgcacata gccgccgaca caagccctcg cttgatgatg cagatagtcc     120
atctgccttt ctctcccctt gccctgctat gactgttgca ttaaattcat catgctgcca     180
aaaaaaaaaa a                                                          191

<210> SEQ ID NO 5
<211> LENGTH: 124
<212> TYPE: DNA
<213> ORGANISM: homo sapiens

<400> SEQUENCE: 5
gccataaata cactttattt cattcgaaat gcataatcac actgggagca ctcccttggg      60
agcactcctc tagcagcagg tccgaagtgc tccagcatcg tcagctggct ccaacaccta     120
cgtc                                                                  124

<210> SEQ ID NO 6
<211> LENGTH: 61
<212> TYPE: DNA
<213> ORGANISM: homo sapiens

<400> SEQUENCE: 6 ttttttttt tttggaaaca gaataaagtg ctttattctc tggctggctc tcctacgtca       60
c                                                                     61

<210> SEQ ID NO 7
<211> LENGTH: 216
<212> TYPE: DNA
<213> ORGANISM: homo sapiens
<220> FEATURE:
<221> NAME/KEY: unsure
<222> LOCATION: 145
<223> OTHER INFORMATION: c, t, a or g
<221> NAME/KEY: misc_feature
<222> LOCATION: (1)...(216)
<223> OTHER INFORMATION: n = A,T,C or G

<400> SEQUENCE: 7
tcggcgatag cattggagca agtcttatca gcaagcaatg ttttcagtta tgtttcaaag      60
ttaagaatgg gtttaaactt gctgaacgta aagattgacc ctcaagtcac tgtagcttta     120
gtacttgctt attgtattag tttanatgct agcaccgcat gtgctctgca tattctggtt     180
ttattaaaat aaaagttga actgcaaaaa aaaaaa                                216

<210> SEQ ID NO 8
<211> LENGTH: 334
<212> TYPE: DNA
<213> ORGANISM: homo sapiens
<220> FEATURE:
```

```
<221> NAME/KEY: unsure
<222> LOCATION: 42, 107, 126
<223> OTHER INFORMATION: c, t, a or g
<221> NAME/KEY: misc_feature
<222> LOCATION: (1)...(334)
<223> OTHER INFORMATION: n = A,T,C or G

<400> SEQUENCE: 8
tttttttttt tttttttttt tttttttttt tttttttttt tngccaggct atgtctcaga      60
ctttattatt attattatta ttattattat tataaataaa acatgtnctt tcaattaggt     120
tacaanagta tttatctcca taacgcttct tcatacatcc ttagttttgg attaaagtac     180
catccacccc aactcaaact gtaaccccca gtaatcccct ctaacgtgga aatttctggt     240
ttaacaactc agttaactgc cccacaaaca gtgggaggcc gctcttgcat ggctatgcca     300
cgtaaccctt cactgcttca cttcttcgct ggct                                 334

<210> SEQ ID NO 9
<211> LENGTH: 136
<212> TYPE: DNA
<213> ORGANISM: homo sapiens

<400> SEQUENCE: 9
gaccgcttgt accatccaac ttgctttgtc ttctgcagag aggaggctaa agcccttgag      60
ctggctggca ctgtactcag gccggaagcc cagctcgtcc cggttcttga caaagcaagt     120
tggatggtac aagcgg                                                     136

<210> SEQ ID NO 10
<211> LENGTH: 316
<212> TYPE: DNA
<213> ORGANISM: homo sapiens

<400> SEQUENCE: 10
tgccgagctg gtattgtga cggttgataa tggcggcatc atgttgccag gtaccgggta       60
agcagacctc agagcacagc ttattgtcca gtgctttcac gctcgcgacg tcaaagtcat     120
tgttattgtc acactccatg cctagaaatg cgcatgtcct ctggccatct tcttgcacag     180
gggatctgtc ctcttcctcc atgatatcat ttccctctgc atcctgctct ccagctggaa     240
ggccagcaaa attgctgtct ggggactctg ctggggtctc ctcctcttct gaaggggccc     300
tgctagcagc tcggca                                                     316

<210> SEQ ID NO 11
<211> LENGTH: 337
<212> TYPE: DNA
<213> ORGANISM: homo sapiens
<220> FEATURE:
<221> NAME/KEY: unsure
<222> LOCATION: 254, 255, 256, 305, 318
<223> OTHER INFORMATION: c, t, a or g
<221> NAME/KEY: misc_feature
<222> LOCATION: (1)...(337)
<223> OTHER INFORMATION: n = A,T,C or G

<400> SEQUENCE: 11 agggtcttg atggacttgg gtcggacatc ttagtgacct gtgaattctt ctgtggaggc       60
tgagtctcac gtagccgagt ttaatatctg tgctatttac taaagtatct gccaccaaat     120
tgtaccaact catagttta tatgaatgtt gatgagtctg tcatcataaat agaattgttg     180
atacatcctt aatttgtgca atattgtatg aagaagattg ttatcaatta aaaccacgcc     240
tcttatgat cctnnnaaaa aaaaaaaaaa aaaaaaaaaa aaaaaaaaaa aaaaaaaaaa      300
```
aaccncctca aatccatngg ttctaaccca aaaccct   337

<210> SEQ ID NO 12
<211> LENGTH: 307
<212> TYPE: DNA
<213> ORGANISM: homo sapiens

<400> SEQUENCE: 12
tttttttttt catacaccat caaaccaatt ttatttctat agcaacgttt ctcacgtctg   60
aacctgagaa taagtcacca gctcttgaca gtaaacatgg gccctatcaa attatattag   120
actcctcagt gtcccgccat gtggccttgc accaaatcaa ttagtttgag ggccaaaatc   180
ctgttgggtt tcaaataaag tgtcaggtca taaggagggg gagggactca attcatggga   240 acattttac ctgttcaaat agataaactg aattgcccta tctgtggtca cctggatcca   300
agaccct   307

<210> SEQ ID NO 13
<211> LENGTH: 296
<212> TYPE: DNA
<213> ORGANISM: homo sapiens
<220> FEATURE:
<221> NAME/KEY: unsure
<222> LOCATION: 59, 101, 110, 122, 131, 133, 148, 189, 191, 198
<223> OTHER INFORMATION: c, t, a or g
<221> NAME/KEY: misc_feature
<222> LOCATION: (1)...(296)
<223> OTHER INFORMATION: n = A,T,C or G

<400> SEQUENCE: 13
ccctgacgat aaatggtaag gaacttttt tttttttttt tttttttttt tttttttnc   60 gaaataaaca aacacagctt attatttggg ggaacattaa nttctataan tgaacacaaa   120
anaaaattaa nanttaatgg gggggtanaa gggactttga atctatctgg tatcatgaca   180
ttgaagcana nacctgantg accagaaaga gagagagaga gagagagaga gagagagaga   240
gagaggtttc atatgagcta gtgttacagg ctttattagt ctattagtca gggacc   296

<210> SEQ ID NO 14
<211> LENGTH: 319
<212> TYPE: DNA
<213> ORGANISM: homo sapiens

<400> SEQUENCE: 14
aatcgggctg gatgggtgta tccggcactg tttcgtagcg gcagcaactg ggtgcttcta   60
tctgaaagcg ggcttcacaa aaactactgc gccacccgac tcgctgcggc atcgcccggt   120
ggcgagtacc gtatcgcctt tcctggtgca gaagaagtgt ttacaggagg cggtcattta   180
ccgcaatctg attctgtttt ttattctccc tggcgggtga tcgcgatcgg cagtttgaaa   240
acgatcgttg aatccacgct cgggaatgat gtggcttcgc cgccaacgct tactgacatt   300
tcatttgtac agcccgatt   319

<210> SEQ ID NO 15
<211> LENGTH: 287
<212> TYPE: DNA
<213> ORGANISM: homo sapiens

<400> SEQUENCE: 15
gccgagctgt gtaaaaccat ctatcctctg gcagatctac ttgccaggcc actcccaggg   60
ggggtagacc ctctaaagct tgagatttat cttacagatg aagacttcga gtttgcactc   120

```
gacatgacca gagatgaatt caacgcactg cccacctgga agcaaatgaa cctgaagaaa      180
gcgaaaggcc tgttctgagg gtgagatgac agccacagag aggtcactgc cactagacca      240
gaaagtggat ggagatatat atttggactg gtgtttttttt ctgtcag                   287
```

<210> SEQ ID NO 16
<211> LENGTH: 344
<212> TYPE: DNA
<213> ORGANISM: homo sapiens
<220> FEATURE:
<221> NAME/KEY: unsure
<222> LOCATION: 208, 269, 337
<223> OTHER INFORMATION: c, t, a or g
<221> NAME/KEY: misc_feature
<222> LOCATION: (1)...(344)
<223> OTHER INFORMATION: n = A,T,C or G

<400> SEQUENCE: 16

```
atcgggctgc agattggaga caagatcatg caggtgaacg gctgggacat gaccatggtc      60
actcatgacc aggctcggaa gcggctcacc aaacgttcgg aggaagtggt ccgcctgctg     120
gtgactcggc agtctctgca gaaggccgta cagcagtcca tgctgtcata gctgtagtca     180
gcctagactt ctgcccactg acctttnggg gcactgagaa cacatccacg ctctgtctgt     240
atctagttct ggcttctgct gtgtgctang ccccagctct gaggagtaac agctgatccc     300
aaaggtccaa gccaaccttc ttacccctca gcccccancc cgat                      344
```

<210> SEQ ID NO 17
<211> LENGTH: 300
<212> TYPE: DNA
<213> ORGANISM: homo sapiens

<400> SEQUENCE: 17

```
tttttttttt tttgggcaac tatgtattta ttgtgtttgg aaggcagagt gagggaggag      60
accccagcag gaagaagact gggtgcagtc tagagttcct agtcaagagt aggaaggttt     120
ctgttatacc catcatagaa cgagagaggg ggctcaatag atcatcccct ttgtctctcc     180
acggggcttc ttgagcttct caaagttctt caggatgatg tcatataaca cagcataagc     240
gttacggatc tccatgacca tcagccggat ctcctggtat tccgcctcgt ccagctcggc     300
```

<210> SEQ ID NO 18
<211> LENGTH: 461
<212> TYPE: DNA
<213> ORGANISM: homo sapiens
<220> FEATURE:
<221> NAME/KEY: unsure
<222> LOCATION: 3, 161, 181, 190, 459
<223> OTHER INFORMATION: c, t, a or g
<221> NAME/KEY: misc_feature
<222> LOCATION: (1)...(461)
<223> OTHER INFORMATION: n = A,T,C or G

<400> SEQUENCE: 18

```
aanatctgct taaaagttct ttaatttgta ccatttcttc aaataaagaa ttttggtaca      60
aattaaagaa cttttaagca gatgttttgg tgcaactaat agaaaagata aaggcagcct     120
gacatgcatg cactgcctca gtgaccagta aagtcacatg nccttgggac gtcagcttag     180
ntttatcacn gtgtcccagg ggtgcttgtc aaagagatat tctgccatgc cagattcagg     240
ggctcccatc ttgcgtaagt tggtcacgtg gtcacccagt tctttaatgg atttcacctg     300
ctcattcagg taatgcgtct caatgaagtc acataagtgg ggatcattct tgtcagtagc     360
```

```
cagtttgtga agttccagta gtgactgatt cacactcttt tccaagtgca gtgcacactc      420
cattgcattc agcccgctct cccagtcatc acggtcacnt a                          461

<210> SEQ ID NO 19
<211> LENGTH: 280
<212> TYPE: DNA
<213> ORGANISM: homo sapiens

<400> SEQUENCE: 19
tgacgtaggg ccgagagcaa caagcacaga actccttctc cagtttcacc ctgatgaagt       60
tgaggcactc ttctgcactg ggaggggcca gcctgggggc caggcacatt ggacaccacc      120
ttcccatgga ctacagcgtc aatgccattg ccttctattc ctataccttc tagggctgc      180 ccctcttccc attcagccaa cactgagtgt tgggagattt ctcttttta aaaacacatg      240 agaaaataaa tgcactttac tccctcccca aaaaaaaaa                             280

<210> SEQ ID NO 20
<211> LENGTH: 177
<212> TYPE: DNA
<213> ORGANISM: homo sapiens

<400> SEQUENCE: 20
gtaggcaata aaatgttttc agaggtgcga aaaagctttt gttttcttaa accattctta       60
gtctctgcca cacttgacac tccgtcaaag tgagaagcga actaaagacc aactgcggtg      120 gaaatatta tgtttatgta ataaaaaaa atcatgtaac tgcaaaaaaa aaaaaa            177

<210> SEQ ID NO 21
<211> LENGTH: 633
<212> TYPE: DNA
<213> ORGANISM: homo sapiens
<220> FEATURE:
<221> NAME/KEY: unsure
<222> LOCATION: 449, 476, 478, 520, 526, 535, 570, 573, 581, 615, 619,
      628
<223> OTHER INFORMATION: c, t, a or g
<221> NAME/KEY: misc_feature
<222> LOCATION: (1)...(633)
<223> OTHER INFORMATION: n = A,T,C or G

<400> SEQUENCE: 21
tgccgagctg aaaacataca tccgcaccgg gttgagatag ctggccctcc gtccccgggc       60
atactctttg gataagaacc ccggccttgt taccaggtac cggagtgagc tgaaaaattt      120
accgtcgaaa tgggtgatgt cctggaaaaa atggttcacc agctgccagg cagattcttt      180
gggttccaca ttttcctgcc cacagatgtg gcagaagcgg tcaagtaatg cagcattaca      240
attgaggcag atcttttctt ttctttcctt ggagtggctc aaccagcgat tttggttaaa      300
aataatcaaa aaagcgacgg caaaactttt gttatattcc cgcctgtggc atttgaactg      360
tgcccggcaa ccgaataact tttaattttg aaaataaaat gcatactaga tttttagcgg      420
ttgcctcctg gccattgctt caggcgccng cacagcgtca gcccagtttt accacnanga      480
atatcctaag cgttgaaaca gggcacagcc gaaaaaaacn ctggcnacaa aaaanatccg      540
gacatccttt ttccaatttt gaaaccgaan gcncgcaaac naaggttctt cgggaaaaaa      600
aatcgccaaa atacncgana tcaaactntc caa                                   633

<210> SEQ ID NO 22
<211> LENGTH: 213
<212> TYPE: DNA
<213> ORGANISM: homo sapiens
```

<400> SEQUENCE: 22

```
tgccgagctg gggggagttc caggaatttg tggactattt ccaggaggaa ttgaggaatc        60
tagaagtaat aagaacttca caagtagaac aacagagtta attgacctct atccttaaga       120
gttaccagag aattattaaa aaactaaaga acaatcaaag cctggtcctg tgccaccacc       180
caaaaacatg tatagcctat gtgcagctcg gca                                     213
```

<210> SEQ ID NO 23
<211> LENGTH: 679
<212> TYPE: DNA
<213> ORGANISM: homo sapiens
<220> FEATURE:
<221> NAME/KEY: unsure
<222> LOCATION: 5, 11, 12, 13, 16, 18, 21, 23, 30, 36, 40, 41, 48, 50,
      53, 55, 56, 59, 72, 91, 92, 103, 106, 120, 123, 129, 133, 136
<223> OTHER INFORMATION: c, t, a or g
<221> NAME/KEY: unsure
<222> LOCATION: 138, 143, 153, 155, 157, 165, 168, 171, 175, 178, 180,
      181, 182, 194, 200, 205, 207, 210, 213, 214, 225, 232, 244, 274,
<223> OTHER INFORMATION: c, t, a or g
<221> NAME/KEY: unsure
<222> LOCATION: 281, 285, 294, 299, 313, 349, 353, 358, 360, 374, 386,
      388, 411, 414, 415, 452, 482, 487, 497, 499, 513, 540, 542, 556,
<223> OTHER INFORMATION: c, t, a or g
<221> NAME/KEY: unsure
<222> LOCATION: 558, 559, 563, 597, 608, 621, 647, 661, 662, 671, 675
<223> OTHER INFORMATION: c, t, a or g
<221> NAME/KEY: misc_feature
<222> LOCATION: (1)...(679)
<223> OTHER INFORMATION: n = A,T,C or G

<400> SEQUENCE: 23

```
ctcanagggc nnnttngngg ncntcatgcn ccaggntccn nccccanan gancnnccng        60
gtaaactaca cnggagtact taagtggaca nnccacatgc ganggncaag gggatcaccn       120
tcnctcctnc agnctntncg tgnctctcct gtncntncac tgcccanaa nggangcncn       180
nnctcctatc tgtntacagn aaacntngcn ctnnctctaa gctcnccac tntgtggaaa       240
ggcnatgtgt gcgtgcctct ccctatcac ggcngtttgc naaangggga tgtnctgcnc       300
ggcgatgaag ttnggtcact ccatgtttcc cagtccnacc tgttagacna agnattgnan      360
tgtgatacga ctcnctgtaa ggggantngc ggacccagta tgtttggccc nacnnccact      420
tctttaaatg gtggctaacg gcgcttccta gnataaacac tattggtccc ccctctgca        480
gnaccntta cttccgnana aaaattgttg tcntgatccg cgacaaccac accgtctgtn       540
gnttttagtt gcaacncnna tcnctccaaa aaagtttcag aaatcttcat tttcccngct     600
tgagcccntg acaaacccct naggatttgt cgaatgtaaa gtctccngat cttcaataaa     660
nntccaaaag nctancgat                                                   679
```

<210> SEQ ID NO 24
<211> LENGTH: 1150
<212> TYPE: DNA
<213> ORGANISM: homo sapiens

<400> SEQUENCE: 24

```
gcggtggtga cggtagtatg gccgcacttt atggtggcgt ggaaggggga ggcacacggt        60
ccaaagtcct tttactttct gaggatgggc agatcctggc agaagcagat ggactgagca       120
caaatcactg gctgattggc acaggtacct gtgtggagag gatcaatgag atggtggaca       180
gggctaaacg gaaggctgga gtggatcctc tggtaccct tcgaagcctg ggcttgtccc        240
tgagtggtgg ggagcaggag gatgcagtga ggctcctgat ggaggagttg agggaccgat       300
```

```
ttccctacct gagtgaaagt tacttcatca ccactgatgc agcaggttcc atcgccacag    360
ctacaccgga tggtgggatt gtgctcatct ctggaacagg ctccaactgt aggcttatca    420
accctgatgg ctctgagagt ggctgtggtg gctggggcca catgatggga gacgagggat    480
cagcctactg gattgcacac caagctgtga aaattgtgtt tgactccatt gacaacctgg    540
aagcagctcc tcatgatatt ggccatgtca agcaggccat gttcaactac ttccaggtgc    600
cagatcggct aggaatcctc actcacttgt atagggactt tgataagtcc aagtttgctg    660
gattttgtca gaaaattgca gaaggtgcac agcagggaga ccctctttcc aggttcatct    720
tcagaaaggc tggggagatg ctgggcagac acgttgtggc agtattgcca gagattgacc    780
cagttttgtt ccaaggggag cttggcctcc ccattctgtg tgtgggctca gtgtggaaga    840
gctgggagct actgaaggaa ggctttctcc tggcactgac gcagggccga gagcaacagg    900
cacagaactc cttctccagt ttcaccctga tgaagttgag gcactcttct gcactgggag    960
gggccagcct gggggccagg cacattggac accaccttcc catggactac agcgtcaatg   1020
ccattgcctt ctattcctat accttctagg ggctgcccct cttcccattc agccaacact   1080
gagtgttggg agatttctct tttttaaaaa cacatgagaa aataaatgca ctttactccc   1140
tccccaaaaa                                                          1150

<210> SEQ ID NO 25
<211> LENGTH: 348
<212> TYPE: PRT
<213> ORGANISM: homo sapiens

<400> SEQUENCE: 25

Gly Gly Asp Gly Ser Met Ala Ala Leu Tyr Gly Val Glu Gly Gly
 1               5                  10                  15

Gly Thr Arg Ser Lys Val Leu Leu Ser Glu Asp Gly Gln Ile Leu
                20                  25                  30

Ala Glu Ala Asp Gly Leu Ser Thr Asn His Trp Leu Ile Gly Thr Gly
                35                  40                  45

Thr Cys Val Glu Arg Ile Asn Glu Met Val Asp Arg Ala Lys Arg Lys
    50                  55                  60

Ala Gly Val Asp Pro Leu Val Pro Leu Arg Ser Leu Gly Leu Ser Leu
65                  70                  75                  80

Ser Gly Gly Glu Gln Glu Asp Ala Val Arg Leu Leu Met Glu Glu Leu
                85                  90                  95

Arg Asp Arg Phe Pro Tyr Leu Ser Glu Ser Tyr Phe Ile Thr Thr Asp
                100                 105                 110

Ala Ala Gly Ser Ile Ala Thr Ala Thr Pro Asp Gly Ile Val Leu
                115                 120                 125

Ile Ser Gly Thr Gly Ser Asn Cys Arg Leu Ile Asn Pro Asp Gly Ser
    130                 135                 140

Glu Ser Gly Cys Gly Gly Trp Gly His Met Met Gly Asp Glu Gly Ser
145                 150                 155                 160

Ala Tyr Trp Ile Ala His Gln Ala Val Lys Ile Val Phe Asp Ser Ile
                165                 170                 175

Asp Asn Leu Glu Ala Ala Pro His Asp Ile Gly His Val Lys Gln Ala
                180                 185                 190

Met Phe Asn Tyr Phe Gln Val Pro Asp Arg Leu Gly Ile Leu Thr His
                195                 200                 205

Leu Tyr Arg Asp Phe Asp Lys Ser Lys Phe Ala Gly Phe Cys Gln Lys
```

| | | | | | | | | | | | |
|---|---|---|---|---|---|---|---|---|---|---|---|
| | | 210 | | | | 215 | | | | 220 | |
| Ile | Ala | Glu | Gly | Ala | Gln | Gln | Gly | Asp | Pro | Leu | Ser | Arg | Phe | Ile | Phe |
| 225 | | | | 230 | | | | 235 | | | | 240 |
| Arg | Lys | Ala | Gly | Glu | Met | Leu | Gly | Arg | His | Val | Val | Ala | Val | Leu | Pro |
| | | | | 245 | | | | 250 | | | | 255 |
| Glu | Ile | Asp | Pro | Val | Leu | Phe | Gln | Gly | Glu | Leu | Gly | Leu | Pro | Ile | Leu |
| | | | 260 | | | | | 265 | | | | 270 |
| Cys | Val | Gly | Ser | Val | Trp | Lys | Ser | Trp | Glu | Leu | Leu | Lys | Glu | Gly | Phe |
| | | | 275 | | | | 280 | | | | | 285 |
| Leu | Leu | Ala | Leu | Thr | Gln | Gly | Arg | Glu | Gln | Gln | Ala | Gln | Asn | Ser | Phe |
| | 290 | | | | | 295 | | | | | 300 |
| Ser | Ser | Phe | Thr | Leu | Met | Lys | Leu | Arg | His | Ser | Ser | Ala | Leu | Gly | Gly |
| 305 | | | | 310 | | | | | 315 | | | | 320 |
| Ala | Ser | Leu | Gly | Ala | Arg | His | Ile | Gly | His | His | Leu | Pro | Met | Asp | Tyr |
| | | | | 325 | | | | 330 | | | | | 335 |
| Ser | Val | Asn | Ala | Ile | Ala | Phe | Tyr | Ser | Tyr | Thr | Phe |
| | | | 340 | | | | | 345 |

<210> SEQ ID NO 26
<211> LENGTH: 800
<212> TYPE: DNA
<213> ORGANISM: homo sapiens

<400> SEQUENCE: 26

```
ggcacgagct ctcctcgtcc cctcccttct ccactgcagc ctttctctta gcccgaacca    60
cttccttctt ctgcttgttc ctccctaggg cgcggaagct gagtgcaggg ttcagaccca   120
cgcggcgagc agctcttcag tgaagaagga agcaatcgga gggtcagcaa tgaacgtgga   180
gcatgaggtt aacctcctgg tggaggaaat tcatcgtctg ggttccaaaa atgccgatgg   240
gaaactgagt gtgaagtttg gggtcctctt ccaagacgac agatgtgcca atctctttga   300
aaccgttggt gggaactctg aaagcccgca aacgaagga agattgttac gtacgcagaa   360
gagctgcttt tgcaaggtgt tcatgatgat gttgacattg tattgctgca agattaatgt   420
ggtttgcaga tctgggggta tctggtaaac tggaataatt aagttaaagg acaaacatga   480
agttccttat gtattttat agacctttgt aaacaaaagg ggacttgttg agaagtcctg   540
ttttatacc ttggagcaaa acattacaat gtaaaataa acaaaacctg ttatttttt   600
ttcttaaga aggtaatcgg gagacgtagg caataaaatg ttttcagagg tgcgaaaaag   660
cttttgtttt cttaaaccat tcttagtctc tgccacactt gacactccgt caaagtgaga   720
agcgaactaa agaccaactg cggtggaaaa tattatgttt atgtaataaa aaaaaatcat   780
gtaaaaaaaa aaaaaaaaaa                                                800
```

<210> SEQ ID NO 27
<211> LENGTH: 92
<212> TYPE: PRT
<213> ORGANISM: homo sapiens

<400> SEQUENCE: 27

| | | | | | | | | | | | |
|---|---|---|---|---|---|---|---|---|---|---|---|
| Met | Asn | Val | Glu | His | Glu | Val | Asn | Leu | Leu | Val | Glu | Glu | Ile | His | Arg |
| 1 | | | | 5 | | | | 10 | | | | | 15 |
| Leu | Gly | Ser | Lys | Asn | Ala | Asp | Gly | Lys | Leu | Ser | Val | Lys | Phe | Gly | Val |
| | | | 20 | | | | 25 | | | | | 30 |
| Leu | Phe | Gln | Asp | Asp | Arg | Cys | Ala | Asn | Leu | Phe | Glu | Thr | Val | Gly | Gly |
| | | 35 | | | | 40 | | | | | 45 |

Asn Ser Glu Ser Pro Gln Asn Glu Gly Arg Leu Leu Arg Thr Gln Lys
    50                  55                  60

Ser Cys Phe Cys Lys Val Phe Met Met Met Leu Thr Leu Tyr Cys Cys
65                  70                  75                  80

Lys Ile Asn Val Val Cys Arg Ser Gly Gly Ile Trp
                85                  90

<210> SEQ ID NO 28
<211> LENGTH: 1538
<212> TYPE: DNA
<213> ORGANISM: homo sapiens
<220> FEATURE:
<221> NAME/KEY: unsure
<222> LOCATION: 652, 1523
<223> OTHER INFORMATION: c, t, a or g
<221> NAME/KEY: misc_feature
<222> LOCATION: (1)...(1538)
<223> OTHER INFORMATION: n = A,T,C or G

<400> SEQUENCE: 28

| | | | | |
|---|---|---|---|---|
| gtgtggtgtg | tctctcagac | gtccgtgaca | ctttgatcct | gccctgccgg cacctgtgcc | 60 |
| tctgcaacac | ctgtgcagac | accctgcgct | accaggccaa | caactgcccc atctgccggc | 120 |
| tgcccttccg | ggcactgctt | cagatccgag | ccatgaggaa | aaaattgggc cctctgtctc | 180 |
| caagcagctt | taacccatc | atctcttccc | agacttcgga | ctctgaggaa cattcatcct | 240 |
| cagagaacat | ccctgcgggc | tatgaagtgg | tgtctctcct | ggaggccctc aatgggcccc | 300 |
| tcacctcatc | cccagcggtg | cctccccttc | acgttcttgg | agatgccac ctctcaggaa | 360 |
| tgctgccgtc | ctatggcagt | gatggccacc | tgcccctgt | taggacactg tccccccttg | 420 |
| accacctgtc | tgattgcaac | agccaagggc | tcaaactcaa | caagtctctc tccaagtcca | 480 |
| tttcccagaa | ttcttctgtg | cttcacgaag | aggaagatga | gcgctcttgc agtgagtcag | 540 |
| acactcagct | ctctcagagg | ctgtcagccc | agcatcctga | gagggacct gatgtgactc | 600 |
| cagagagtga | gaacctcacg | ctgtcctcct | caggggctgt | tgaccagtca tnttgcacag | 660 |
| ggactccgct | ctcttccacc | atctcctccc | agaagaccc | agccagcagc agcctggccc | 720 |
| agtcagtcat | gtccatggcc | tcctcccaga | tcagcactga | caccgtgtcc tccatgtctg | 780 |
| gctcctacat | tgcacctggc | acagaagaag | aaggagaggc | cccaccttcc ccccgagctg | 840 |
| ctagcagggc | cccttcagaa | gaggaggaga | ccccagcaga | gtccccagac agcaattttg | 900 |
| ctggccttcc | agctggagag | caggatgcag | agggaaatga | tatcatggag aagaggaca | 960 |
| gatcccctgt | gcaagaagat | ggccagagga | catgcgcatt | tctaggcatg gagtgtgaca | 1020 |
| ataacaatga | ctttgacgtc | gcgagcgtga | agcactggaa | caataagctg tgctctgagg | 1080 |
| tctgcttacc | cggtacctgg | caacatgatg | ccgccattat | caaccgtcac aatacccagc | 1140 |
| gccggcgact | atcacccagc | agcctggagg | accctgagga | ggacaggcct tgcgtatggg | 1200 |
| atcctttggc | tgtctgaggg | cactggcacc | tgtacctggg | cttcccctcc tgtccgcctt | 1260 |
| ccatctgtcc | tcactggacc | acaggccttc | tgggcatctt | caacaagaca cgtgacttt | 1320 |
| ctactctcat | gaagggagga | cagtgcaacc | ctccaccaac | ttcatctcct gtaaccatga | 1380 |
| ttcttaccct | ctcagaaagt | accagaagcc | ttcctcctgt | gggctgatgt gtgccagcca | 1440 |
| aacccagtgg | gtcagctgag | ctgagggtca | gggctggttg | tttctgtagc ctttctctt | 1500 |
| ccaaatggag | accaacgaga | aanaaaaaaa | aaaaaaaa | | 1538 |

<210> SEQ ID NO 29
<211> LENGTH: 404

```
<212> TYPE: PRT
<213> ORGANISM: homo sapiens
<220> FEATURE:
<223> OTHER INFORMATION: unknown amino acid
<221> NAME/KEY: VARIANT
<222> LOCATION: (1)...(404)
<223> OTHER INFORMATION: Xaa = Any Amino Acid

<400> SEQUENCE: 29

Val Val Cys Leu Ser Asp Val Arg Asp Thr Leu Ile Leu Pro Cys Arg
 1               5                  10                  15

His Leu Cys Leu Cys Asn Thr Cys Ala Asp Thr Leu Arg Tyr Gln Ala
            20                  25                  30

Asn Asn Cys Pro Ile Cys Arg Leu Pro Phe Arg Ala Leu Leu Gln Ile
        35                  40                  45

Arg Ala Met Arg Lys Lys Leu Gly Pro Leu Ser Pro Ser Ser Phe Asn
 50                  55                  60

Pro Ile Ile Ser Ser Gln Thr Ser Asp Ser Glu His Ser Ser Ser
65                  70                  75                  80

Glu Asn Ile Pro Ala Gly Tyr Glu Val Val Ser Leu Leu Glu Ala Leu
                85                  90                  95

Asn Gly Pro Leu Thr Ser Ser Pro Ala Val Pro Leu His Val Leu
            100                 105                 110

Gly Asp Gly His Leu Ser Gly Met Leu Pro Ser Tyr Gly Ser Asp Gly
            115                 120                 125

His Leu Pro Pro Val Arg Thr Leu Ser Pro Leu Asp His Leu Ser Asp
    130                 135                 140

Cys Asn Ser Gln Gly Leu Lys Leu Asn Lys Ser Leu Ser Lys Ser Ile
145                 150                 155                 160

Ser Gln Asn Ser Ser Val Leu His Glu Glu Glu Asp Glu Arg Ser Cys
                165                 170                 175

Ser Glu Ser Asp Thr Gln Leu Ser Gln Arg Leu Ser Ala Gln His Pro
            180                 185                 190

Glu Glu Gly Pro Asp Val Thr Pro Glu Ser Glu Asn Leu Thr Leu Ser
        195                 200                 205

Ser Ser Gly Ala Val Asp Gln Ser Xaa Cys Thr Gly Thr Pro Leu Ser
210                 215                 220

Ser Thr Ile Ser Ser Pro Glu Asp Pro Ala Ser Ser Ser Leu Ala Gln
225                 230                 235                 240

Ser Val Met Ser Met Ala Ser Ser Gln Ile Ser Thr Asp Thr Val Ser
                245                 250                 255

Ser Met Ser Gly Ser Tyr Ile Ala Pro Gly Thr Glu Glu Gly Glu
            260                 265                 270

Ala Pro Pro Ser Pro Arg Ala Ala Ser Arg Ala Pro Ser Glu Glu Glu
        275                 280                 285

Glu Thr Pro Ala Glu Ser Pro Asp Ser Asn Phe Ala Gly Leu Pro Ala
290                 295                 300

Gly Glu Gln Asp Ala Glu Gly Asn Asp Ile Met Glu Glu Asp Arg
305                 310                 315                 320

Ser Pro Val Gln Glu Asp Gly Gln Arg Thr Cys Ala Phe Leu Gly Met
                325                 330                 335

Glu Cys Asp Asn Asn Asn Asp Phe Asp Val Ala Ser Val Lys Ala Leu
            340                 345                 350

Asp Asn Lys Leu Cys Ser Glu Val Cys Leu Pro Gly Thr Trp Gln His
        355                 360                 365
```

Asp Ala Ala Ile Ile Asn Arg His Asn Thr Gln Arg Arg Arg Leu Ser
    370                 375                 380

Pro Ser Ser Leu Glu Asp Pro Glu Glu Asp Arg Pro Cys Val Trp Asp
385                 390                 395                 400

Pro Leu Ala Val

<210> SEQ ID NO 30
<211> LENGTH: 922
<212> TYPE: DNA
<213> ORGANISM: homo sapiens

<400> SEQUENCE: 30

```
ggcacgaggc gccgccttcc tgctcgcgcc ctatcgccgc cttcctgctc gcgccctatc     60
gccgcctccg agtcttcctg cgccccgggc ttccgccgct tcattgattt ccgtttctcg    120
ccgctgcagc ctcctgacac ggtgatccgg gcgggccccg caggaatttt atcccctcac    180
cggcctcaca ctagtgtcgc atgtccacta tccagaacct ccaatctttc gacccctttg    240
ctgatgcaac taagggcgac gacttactcc cggcagggac tgaggactac attcatataa    300
gaatccagca gcggaacggc aggaagacgc tgaccactgt gcagggcatt gcggacgatt    360
atgacaaaaa gaaacttgtg aaagctttca aaaagaaatt cgcctgtaat gggactgtga    420
ttgaacaccc tgagtacgga gaggtcattc agcttcaagg cgaccaaagg aagaacattt    480
gccagtttct tttggaggtt ggcatcgtca aggaggagca gctgaaggtt cacggattct    540
aagatgaacc cgaacatgtg gcgagtttct taaatggttt tgttgtctaa ctcagtttgg    600
ctgcctcggg agatgattct ttacagtaaa cgacagactt tgcgtttatt aaatcattca    660
gacttccact cacgcctgca tggctacaga aaacatgggg tatgtaggct cctaagtcac    720
aaggaaatcg ccgtgaggtg gggacgaagc ccgagtccgt cctgacatgt ttccagtgga    780
aaagattttg ttctgagcgt tcatttctag tttattttca cttgattgtt aaatgttttt    840
gttgttgttt tattaaacca tgtatgttgc agcttaacaa taaaggagga agtctgtgc    900
gtcaaaaaaa aaaaaaaaa aa                                              922
```

<210> SEQ ID NO 31
<211> LENGTH: 113
<212> TYPE: PRT
<213> ORGANISM: homo sapiens

<400> SEQUENCE: 31

Met Ser Thr Ile Gln Asn Leu Gln Ser Phe Asp Pro Phe Ala Asp Ala
1               5                   10                  15

Thr Lys Gly Asp Asp Leu Leu Pro Ala Gly Thr Glu Asp Tyr Ile His
            20                  25                  30

Ile Arg Ile Gln Gln Arg Asn Gly Arg Lys Thr Leu Thr Thr Val Gln
        35                  40                  45

Gly Ile Ala Asp Asp Tyr Asp Lys Lys Leu Val Lys Ala Phe Lys
    50                  55                  60

Lys Lys Phe Ala Cys Asn Gly Thr Val Ile Glu His Pro Glu Tyr Gly
65                  70                  75                  80

Glu Val Ile Gln Leu Gln Gly Asp Gln Arg Lys Asn Ile Cys Gln Phe
                85                  90                  95

Leu Leu Glu Val Gly Ile Val Lys Glu Gln Leu Lys Val His Gly Phe
            100                 105                 110

Phe

<210> SEQ ID NO 32
<211> LENGTH: 1856
<212> TYPE: DNA
<213> ORGANISM: homo sapiens

<400> SEQUENCE: 32

| | | | | | |
|---|---|---|---|---|---|
| ggcgttgcga | cgtggacatg | tcggcgtcgt | tggtccgcgc | caccgtgcgg | gccgtgagca | 60 |
| agagaaaact | gcaacccacg | cgggcggcgc | tcacgctgac | cccctctgct | gtgaacaaga | 120 |
| taaacaact | tcttaaagac | aagcctgagc | atgtgggtct | gaaagtgggt | gtgcggacca | 180 |
| ggggctgtaa | cggcctctct | tacagcctgg | agtatacaaa | gacaaaagga | gatgctgatg | 240 |
| aagaagttat | tcaagacgga | gtccgagtgt | tcatcgagaa | gaaagcccag | ctaaccctgt | 300 |
| taggcacaga | gatggactat | gtggaagaca | aactgtccag | tgagtttgtg | tcaacaaccc | 360 |
| caacatcaag | ggaacctgtg | gctgcggtga | agctttaac | gtctgaaagc | tgaggactgc | 420 |
| aaactccagg | agagctgggt | ctgccttgga | gcacaccgaa | gaaatcatgt | gatgtcccgt | 480 |
| gtcggaagtt | agtgtgtggc | tgcctcgtgg | ttgagaataa | agtgaagcat | tgaaaatcaa | 540 |
| gccagcgtgt | tagagttcca | aaacatggt | gtctgttctc | tgtaagacac | aaatggagag | 600 |
| aacatggtgt | ctgttctctg | gaggacacaa | actgagaaac | tgttgagtcc | tctgtcctgt | 660 |
| acagaaaact | cctaccctgc | ccttacgctg | tagcctgctc | tgtgctagaa | ccagcttcgt | 720 |
| gaccattgct | ttgctgggaa | ttgaggaatg | ggataacggg | tgtgcacctg | ggtcacagaa | 780 |
| tggcttgaga | ctgtctcctg | gccctgtctc | acctcaggca | gggcagctgt | gggagcagca | 840 |
| gctgtgggag | cggtgagggg | acctggtttc | cctcacctgt | ggcgtggccc | gttgcatctt | 900 |
| taccacgtgc | ctgttgtcag | atacctcatt | tgccagcctc | cagcaagctc | agctatgagt | 960 |
| gccagtctca | ggaggtaggg | atcacgggcc | tggtgtcagt | ctgtcctctg | gggcgtgctt | 1020 |
| catgcggttt | gcttagacct | ttcagttaga | agcgcttgtg | atgagcagcc | aggtagacct | 1080 |
| gctgagagcg | tggttctcag | agcttctgcc | cagccctcct | cacaggtcac | agcagacagt | 1140 |
| gctgtctgag | acactcggtg | aggagacatc | ctgcctggcc | agtgctccta | ccagtttaga | 1200 |
| gactgcatta | gttttctctt | gaatggaagc | cttgtgtaaa | ccctttttgtc | tgaatggcca | 1260 |
| tcctgtttag | agctttgaac | cagtagtgtc | ttccttcaga | gatctgcag | cagaggggtc | 1320 |
| cctctcagca | cggcacctgg | ggggcagaac | atgcacacac | ttacagttgc | cagggtgcag | 1380 |
| atgctccctg | cttcccagag | gaagcttcta | agtttcttta | atgtggtcat | caccagtttt | 1440 |
| ttgagccatg | gttttgctgt | atactacagg | ccagccttga | acccacaaca | atcctcctgc | 1500 |
| ttccacgttc | agaggcatgt | gctaccacac | ctgacctgga | tcccaagttt | ctcttaagt | 1560 |
| ggtcttgatg | gacttgggtc | ggacatctta | gtgacctgtg | aattcttctg | tggaggctga | 1620 |
| gtctcacgta | gccgagttta | atatctgtgc | tatttactaa | agtatctgcc | accaaattgt | 1680 |
| accaactcat | agtttatat | gaatgttgat | gagtctgtat | cataaataga | attgttgata | 1740 |
| catccttaat | ttgtgcaata | ttgtatgaag | aagattgtta | tcaattaaaa | ccacgcctct | 1800 |
| ttatgatcct | aaaaaaaaaa | aaaaaaaaa | aaaaaaaaa | aaaaaaaaa | aaaaaa | 1856 |

<210> SEQ ID NO 33
<211> LENGTH: 134
<212> TYPE: PRT
<213> ORGANISM: homo sapiens

<400> SEQUENCE: 33

Arg Cys Asp Val Asp Met Ser Ala Ser Leu Val Arg Ala Thr Val Arg

|  | 1 |  |  |  | 5 |  |  |  | 10 |  |  |  | 15 |  |
|---|---|---|---|---|---|---|---|---|---|---|---|---|---|---|
| Ala | Val | Ser | Lys | Arg | Lys | Leu | Gln | Pro | Thr | Arg | Ala | Ala | Leu | Thr | Leu |
|  |  |  | 20 |  |  |  |  | 25 |  |  |  | 30 |  |  |  |
| Thr | Pro | Ser | Ala | Val | Asn | Lys | Ile | Lys | Gln | Leu | Leu | Lys | Asp | Lys | Pro |
|  |  | 35 |  |  |  |  | 40 |  |  |  |  | 45 |  |  |  |
| Glu | His | Val | Gly | Leu | Lys | Val | Gly | Val | Arg | Thr | Arg | Gly | Cys | Asn | Gly |
|  | 50 |  |  |  |  | 55 |  |  |  |  | 60 |  |  |  |  |
| Leu | Ser | Tyr | Ser | Leu | Glu | Tyr | Thr | Lys | Thr | Lys | Gly | Asp | Ala | Asp | Glu |
| 65 |  |  |  |  | 70 |  |  |  |  | 75 |  |  |  |  | 80 |
| Glu | Val | Ile | Gln | Asp | Gly | Val | Arg | Val | Phe | Ile | Glu | Lys | Lys | Ala | Gln |
|  |  |  |  | 85 |  |  |  |  | 90 |  |  |  |  | 95 |  |
| Leu | Thr | Leu | Leu | Gly | Thr | Glu | Met | Asp | Tyr | Val | Glu | Asp | Lys | Leu | Ser |
|  |  |  | 100 |  |  |  |  | 105 |  |  |  |  | 110 |  |  |
| Ser | Glu | Phe | Val | Phe | Asn | Asn | Pro | Asn | Ile | Lys | Gly | Thr | Cys | Gly | Cys |
|  |  | 115 |  |  |  |  | 120 |  |  |  |  | 125 |  |  |  |
| Gly | Glu | Ser | Phe | Asn | Val |
|  |  | 130 |  |  |  |

<210> SEQ ID NO 34
<211> LENGTH: 1925
<212> TYPE: DNA
<213> ORGANISM: homo sapiens

<400> SEQUENCE: 34

```
acgagctgaa ggtcacttcg cgcacgggtt ggacctgggg caggttggag gagtaggagt     60
atgtcattgg gcgcgaagac ggggtctggg gcaaaaaaga agggaggctg gagaaatctg    120
gacccgagac gtagtaagta caacttggca aatacatgtt agaggagcag ggaccacgct    180
catcaaaatc catcattggg ctaccttggg ctctccgcag tagccgagct taacatgatt    240
ctccactgca gctgcctctt tgaagcggat ccgtgaagta gaaatttgga gacgtaagct    300
gacgtggaaa tctatcccca tccttagcag ggaggtgctg gtcatgtgac ccgatgttga    360
aattgacaag ccgcgagcta gtcccggctt tttttttta accccctcc ctttcctttt     420
ttccccctcc cctccctcct cggcttcctt tctttgtagc cacctcaggg gaagcaacag    480
atcgtcactc ggtgttctca ccgaaagcac gtaatcgccg tgtaactca tgttggctgg     540
ggggcctccc cgctcgcaga aaggctgggg tgcgccccca agcagctttc ctttgctcag    600
ctgcatggtc ctggtccacg agcgctctga gggcggcaag agagcgcaac tcctgacgcc    660
tccccccact ccccggtggg tgagggatgc tctgggatgg gggtggccag gtgaacgccc    720
ggaattgtgt agcttcaggt tccggagtct gttgtccgaa ggcttacgtt cagcaccttc    780
ttcgcagtcc ccctcccaca gacttgctct ggaaagcacc tcagtctcag aatctggctg    840
gaccccattt ggggccaggc ttcgcagcca cgatgtgccg ggcttcgtgg cttgtccgat    900
ttgcacggtg acttgattac acgctctcat tcatggtcac ttccgaagcg ctttagtgcc    960
ttccgtcccc aaaccgccaa caggcaaagc ggctttcctc cgcggtttgt caataatccg   1020
cgctgtccgg aagggcttcg ccttacccgg gttccacctt ccctgtatct ttctgcttac   1080
ttcctcatcc cacactctgt ccttggagga accccttctc ctcgctgcct gtagggttc    1140
ggagtgactc cacagagcca gaggcgcttc tgctcaccgg tccgcaagct gcctggtctg   1200
ctgaagctga cgaatcggga aaccatgcaa ttgaggcgaa ccttgggctg ctttagaggc   1260
gctgaggagc cttctcctgg gaggcccaag gtcgatttca gccaccagg atctggggaa    1320
gacccaacta ggggtaagag cacaccggaa ggccaagtcc gagttccagt cctagaagag   1380
```

```
gcggctgcgg gcaaggttat gacattggcc ctggacactg gtttcccagg agctattctt      1440
tctcaagaac tccacagcac ggggctgtct ccagaaaata ctcttcaacg tttatttcct      1500
ttaatcgtca acccgcagcc ctacggcggt taatgcgaga ggccaaaaat gtttggagga      1560
agaaaaacaa aggcaggaag tggccgcggc ctgacggtgc gtgtgtgtct gtaaagaagg      1620
gagggagccg gttcaatctc ttcttttttt ccccgaattt caaggtttag gcagaccccc      1680
gtagggcctg gccgaggctc acccggcgga gcatttggag gtggccaatg agtaaggctc      1740
gtcgggctga gtttcttctg atttggtcct aaagggtata tgctagtgtc cacagcggct      1800
cctgtggctg ctgttttcct cctgtcggac taaatgtacc aagaagggag agagattgag      1860
gcaccttgcg cgctcctctc tccttccgag gtagaatatc agaataaagt gtattcaggt      1920
gccaa                                                                  1925
```

<210> SEQ ID NO 35
<211> LENGTH: 1195
<212> TYPE: DNA
<213> ORGANISM: homo sapiens

<400> SEQUENCE: 35

```
atcgggctgt actaacagat tgtttgtaaa cagtgacaca gtgataactt ccgtgttact        60
tcttaacttt atgtttctgc tttcagatct ccctcccctt ccagaggaag ttagcgatgc       120
catagcttta atgtctgttt tagctgcaaa actcattgtt cactttctgt tagaaaatct       180
aaagcaggtg gtatgcaatt tctcttgatt tggaattctt taaaggcaag taaatttgga       240
actcctgtgt tgggggggtta acggaggtag gaacccaatg gtgtgtccct aggtcgtccc       300
cgttctcgga tagcacagtc tgcatagcca tagctctcaa ttatgtcact accctaatca       360
tcgcagcccg gttctcacgg actctttgaa gtcccaaaat gacttttgtt tgatcctgat       420
ttggattttc aatggaaagt aaaagcttgg ggtgaggaag cagcagctaa gcagggagt        480 tgagccagtg aattgctgac ggaaaggatt ctggtcttgg aggagggga cctgaagcag        540 aaggaaaagg gatccttcgc ttaagttctt aggaaaaatc ttgactcaga atcccaagat       600 tttcccttc atcccagccg ggtaaatatt tggttttgtc ttttaagtat agcatgaagc        660
ccgtggatga gagccatgtg ttgtaggatt ctcttcccta ttggctctga gcttgtgtca       720
ccgttcagtt tgctccctac aaagggacct agtttggaaa ggattggaag ggcaactgtt       780
cagcggcaat ggaacaccca aacgtggact gggacaacgg gattctgata aagggaaatt       840
tctggtctgg tcctggctgt gtcatagctc tttatgtgtg catggagagc tcttgatcca       900
agtagaatat gtaacaatac agaccaggat cttccagtca gtactgctgg gtggaagtgg       960
gcgggtgatg gtagttgcta gaagaatcat taagacagca tctgcggtga atgcgtccca     1020
aagcctcgcg gcatcagttt catctctaaa ccattagctt acagttgatt ccgtttcctg     1080
ggacagagaa acatccccac gcgaagtgac tgtgttgtgt attcatagca ctgcaaataa     1140
attcacgcgc catgatgaaa ccttgcaaat acgctttgac caaaaaaaaa aaaaa          1195
```

<210> SEQ ID NO 36
<211> LENGTH: 1149
<212> TYPE: DNA
<213> ORGANISM: homo sapiens

<400> SEQUENCE: 36

```
gggtgtgggg cagctgggtg ggagcagcgt gcaggctacc agcaccaagt ggtgtgcctc        60
```

-continued

| | |
|---|---|
| tccgggggtg tgtgcagaag gctcctgggg aaaactgcac aggtaccacc cctagacaga | 120 |
| aatcgaaaac ccacttctct cggtgcccca agcaatacaa gcattactgc atccatggga | 180 |
| gatgccgctt cgtgatggac gaacaaactc cctcctgcat ctgtgagata ggctactttg | 240 |
| gggcccggtg tgagcaggtg gacctgtttt atctccagca ggacaggggg cagatcctgg | 300 |
| tggtctgctt gataggcgtc atggtgctgt tcatcatttt agtcattggc gtcttgcacc | 360 |
| tgctgtcatc ctcttcggaa acatcgcaaa agaagaagg aagagaaaat ggaaactttg | 420 |
| agtaaagata aaactcccat aagtgaagat attcaagaga ccaatattgc ttaacttaat | 480 |
| gattataaag ttaccacaag ctgatggcga gctccaaaag acctgactca tttgcagatg | 540 |
| gacaggacat gtctcaggaa aacagcttgc agaaatgaat gtttaaatat tgtatttgct | 600 |
| ttttcatttt atttgtaact gtgtgttgtt attgttttta ataatgatat ttttgttaca | 660 |
| gtctgatagc tgagaaaaaa atgacctggt taggtgacga caataaggga cattgaatat | 720 |
| aaactttgtt gctaggatta ttaaacaaac aaaatttgga aagaagttag attttaagaa | 780 |
| ctgagtcatg gtcaggcagc gatggcacac atctttaatc ccagcacttg ggagcagagg | 840 |
| caggtagatc tctgggagtt tgaggtcagc ctggtctaca aagcaagatc cagggtagcc | 900 |
| aaggttatat agagaaaccc tgtctcacaa aaccaaacca accaatcaac caaacagcaa | 960 |
| aacacctgag tcgataaaag ggctccccag gtttatacac ttaccgtatg ctaagagctt | 1020 |
| gaaatatatt gtttcgtttt atcgttcagt agtctgtgag attgcatttt ttctcattcc | 1080 |
| tatatataaa aaagttaaat gatttcccctt agatgtagag atagaggaag ttagcgatgc | 1140 |
| catagcttt | 1149 |

<210> SEQ ID NO 37
<211> LENGTH: 717
<212> TYPE: PRT
<213> ORGANISM: homo sapiens

<400> SEQUENCE: 37

```
Asn Thr Cys Asn Asn Cys Thr Thr Asn Asn Cys Asn Asn Asn Gly Gly
  1               5                  10                  15

Cys Thr Gly Ala Thr Ala Thr Cys Asn Gly Gly Cys Asn Cys Thr Thr
              20                  25                  30

Cys Asn Thr Cys Cys Asn Cys Gly Ala Thr Cys Asn Cys Ala Gly Ala
          35                  40                  45

Thr Ala Cys Asn Asn Gly Cys Asn Cys Ala Cys Gly Gly Asn Asn
      50                  55                  60

Asn Thr Asn Thr Cys Asn Gly Asn Gly Gly Thr Asn Ala Thr Cys Asn
 65                  70                  75                  80

Thr Cys Cys Asn Cys Cys Ala Thr Cys Thr Cys Thr Cys Asn Thr Cys
              85                  90                  95

Cys Cys Cys Gly Ala Cys Asn Thr Gly Cys Ala Cys Thr Cys Cys Gly
             100                 105                 110

Gly Gly Thr Asn Thr Asn Asn Thr Ala Cys Ala Cys Asn Gly Gly Ala
             115                 120                 125

Cys Ala Cys Thr Gly Thr Ala Thr Cys Asn Asn Ala Cys Ala Gly Asn
         130                 135                 140

Ala Ala Ala Cys Cys Thr Asn Cys Cys Asn Gly Gly Cys Cys Cys
145                 150                 155                 160

Cys Ala Gly Gly Gly Ala Thr Cys Ala Cys Cys Ala Thr Asn Cys Cys
                 165                 170                 175
```

-continued

```
Thr Cys Gly Asn Cys Cys Cys Asn Gly Cys Asn Thr Gly Thr Asn Thr
            180                 185                 190
Ala Thr Ala Ala Asn Ala Thr Cys Ala Gly Gly Asn Asn Asn Thr Ala
        195                 200                 205

Cys Ala Thr Cys Asn Ala Asn Gly Ala Ala Cys Asn Asn Ala Cys Thr
    210                 215                 220

Ala Thr Cys Ala Cys Asn Gly Asn Thr Cys Thr Cys Thr Asn Thr Thr
225                 230                 235                 240
Asn Asn Cys Thr Cys Ala Gly Thr Gly Thr Asn Cys Ala Cys Cys Thr
                245                 250                 255
Thr Cys Cys Ala Cys Thr Asn Cys Asn Gly Ala Ala Asn Cys Thr Asn
            260                 265                 270

Asn Thr Cys Gly Cys Thr Asn Cys Asn Cys Cys Asn Cys Asn Gly Thr
        275                 280                 285

Thr Gly Gly Gly Ala Ala Ala Gly Gly Cys Gly Ala Asn Cys Asn Gly
    290                 295                 300

Thr Asn Cys Cys Gly Gly Cys Asn Ala Cys Ala Thr Gly Cys Cys Gly
305                 310                 315                 320

Thr Thr Thr Asn Cys Gly Asn Cys Asn Thr Cys Thr Gly Asn Asn Cys
                325                 330                 335

Ala Cys Asn Thr Gly Gly Gly Gly Ala Thr Cys Thr Asn Cys Thr Asn
            340                 345                 350

Cys Ala Ala Asn Gly Asn Ala Ala Thr Cys Ala Ala Thr Thr Asn Gly
        355                 360                 365

Asn Gly Thr Ala Ala Cys Cys Cys Ala Cys Gly Gly Thr Thr Thr Asn
    370                 375                 380

Cys Asn Cys Ala Ala Thr Cys Ala Cys Thr Ala Cys Thr Thr Cys Thr
385                 390                 395                 400

Cys Ala Asn Asn Cys Asn Ala Asn Gly Gly Cys Cys Asn Thr Thr Gly
                405                 410                 415

Ala Ala Asn Thr Gly Thr Thr Ala Thr Cys Cys Cys Ala Cys Cys Ala
            420                 425                 430

Cys Cys Ala Asn Gly Gly Gly Gly Cys Asn Ala Asn Thr Cys Gly Gly
        435                 440                 445

Gly Ala Cys Cys Thr Asn Ala Cys Ala Ala Thr Thr Cys Ala Thr Cys
    450                 455                 460

Cys Thr Cys Ala Gly Cys Cys Gly Gly Cys Cys Cys Cys Ala Gly Asn
465                 470                 475                 480

Cys Thr Thr Ala Ala Ala Ala Ala Ala Thr Thr Cys Ala Ala Ala Gly
                485                 490                 495

Gly Asn Cys Asn Cys Thr Thr Gly Cys Cys Gly Cys Asn Thr Thr
            500                 505                 510

Asn Thr Thr Asn Cys Cys Thr Thr Ala Gly Cys Cys Cys Gly Cys Cys
        515                 520                 525

Asn Cys Cys Asn Gly Ala Cys Ala Ala Cys Ala Asn Cys Cys Asn Ala
    530                 535                 540

Asn Asn Ala Ala Cys Ala Ala Cys Cys Cys Cys Cys Asn Asn Thr Cys
545                 550                 555                 560

Thr Thr Ala Asn Gly Thr Thr Gly Cys Asn Asn Ala Asn Cys Cys Cys
                565                 570                 575

Ala Cys Ala Gly Gly Ala Asn Asn Thr Thr Gly Asn Asn Ala Thr Ala
            580                 585                 590

Cys Cys Gly Gly Gly Thr Thr Thr Cys Cys Cys Cys Asn Gly Ala Ala
```

```
                595                 600                 605
Ala Cys Thr Asn Cys Thr Cys Ala Ala Asn Gly Cys Asn Cys Cys
        610                 615                 620

Gly Thr Thr Cys Cys Ala Ala Cys Cys Cys Cys Gly Thr Thr Ala
625                 630                 635                 640

Cys Gly Ala Ala Ala Cys Cys Gly Thr Asn Cys Cys Asn Thr Thr
                645                 650                 655

Thr Cys Thr Thr Cys Cys Gly Ala Gly Asn Thr Thr Gly Cys Cys
        660                 665                 670

Thr Ala Thr Thr Ala Ala Asn Asn Cys Cys Cys Cys Asn Ala Ala
        675                 680                 685

Gly Thr Thr Cys Thr Asn Cys Thr Thr Cys Gly Thr Thr Asn Gly Asn
        690                 695                 700

Thr Thr Cys Cys Thr Cys Cys Gly Ala Ala Ala Asn Gly
705                 710                 715
```

<210> SEQ ID NO 38
<211> LENGTH: 235
<212> TYPE: DNA
<213> ORGANISM: homo sapiens
<220> FEATURE:
<221> NAME/KEY: unsure
<222> LOCATION: 10, 11, 12, 13, 18, 20, 29, 30, 31, 39, 40, 46, 47, 49,
      58, 71, 84, 90, 103, 111, 123, 126, 139, 141, 165, 185, 192, 199
<223> OTHER INFORMATION: c, t, a or g
<221> NAME/KEY: unsure
<222> LOCATION: 204, 211, 213, 214, 228
<223> OTHER INFORMATION: c, t, a or g
<221> NAME/KEY: misc_feature
<222> LOCATION: (1)...(235)
<223> OTHER INFORMATION: n = A,T,C or G

<400> SEQUENCE: 38
tcactgggcn nnntggtngn cgtcatgcnn naggttccnn ccccnnang  aacctccngg    60 taatctacac nggagtctta agtngacaan cccacactgc ganggtcaag nggatcacca   120
tcnccnnctc ccaagcttnt ncattgatgc tctctctgtt ccgtnccctg ccgctacaca   180
tggangctct tnctccttnt ctcntcttac nanncaaaca ttgccctntc tcata        235

<210> SEQ ID NO 39
<211> LENGTH: 328
<212> TYPE: DNA
<213> ORGANISM: homo sapiens
<220> FEATURE:
<221> NAME/KEY: unsure
<222> LOCATION: 6, 11, 12, 28, 37, 40, 50, 68, 74, 86, 89, 93, 101, 107,
      117, 145, 159, 163, 164, 169, 172, 178, 179, 184, 186, 191
<223> OTHER INFORMATION: c, t, a or g
<221> NAME/KEY: unsure
<222> LOCATION: 192, 203, 204, 205, 215, 218, 219,  228, 229, 232, 233,
      235, 237, 239, 245, 247, 248, 250, 252, 254, 266, 274, 279
<223> OTHER INFORMATION: c, t, a or g
<221> NAME/KEY: unsure
<222> LOCATION: 284, 288, 290, 300, 304, 312, 317, 322
<223> OTHER INFORMATION: c, t, a or g
<221> NAME/KEY: misc_feature
<222> LOCATION: (1)...(328)
<223> OTHER INFORMATION: n = A,T,C or G

<400> SEQUENCE: 39
gggaanggga nnaaaaagga attttttngg gggggnttn tctgggaaan ttttttttt     60 tttttggnaa aaangggggg ggaaanaanc cgnttttccc naaaacnggg gggaacnggc   120 cggggggga aaaaaaaggg ttacnaaggg aaaccttna aannggaang gntttgcnnc     180

```
cctntngaaa nntttgcccc ccnnnaggaa tcccnggnna aacccaannc cnncncncng      240
ggggncnntn cnangggacc ccaacncggg cccnaactng gggnaaanan gggcaaaacn      300
ggtnccnggg gnaaaanggt anccccct                                        328
```

<210> SEQ ID NO 40
<211> LENGTH: 196
<212> TYPE: DNA
<213> ORGANISM: homo sapiens

<400> SEQUENCE: 40

```
tgccgagctg ggggtgaagc accggaaaac aaccgatcca tctcttatca cagggtctcc      60
aagatcccaa acccaaaagc cacattgtta attagccttt ttattgtgtt tttttttttt     120
tttttttttt tttttttttt tttttttttt tttttttttt tttttttttt tttttttttt     180
ttttggcagc tcggca                                                     196
```

<210> SEQ ID NO 41
<211> LENGTH: 422
<212> TYPE: DNA
<213> ORGANISM: homo sapiens

<400> SEQUENCE: 41

```
tacgggcgct gattttttacg aacattacct ggcagggaa atttgataag tatccactgt      60
gggtggcgac tacctggtaa aagacaaacc ccgtgtgaaa aggccctgga cttttttggca    120 acacaacgaa accggccacg tgaatggcat ccggtcttat gtggacttca atgttttcaa    180
cggggacagc acagattttg ccgaactatt aatgaaataa tgcagaattt cgcttttcaa    240
ataagcccat ggatcctgac gtaaaatatt tcctgctggt gatcgtgcag tccatttcga    300
tgctcatact ttggctgatg ctcaacatga cctttgggat ctattttaat tttgctttcc    360
ccgacaatgg tttgacgctt ggcaacatca tttattacct cttcctgctg ggcagctcgg    420
ca                                                                   422
```

<210> SEQ ID NO 42
<211> LENGTH: 304
<212> TYPE: DNA
<213> ORGANISM: homo sapiens
<220> FEATURE:
<221> NAME/KEY: unsure
<222> LOCATION: 2, 7, 71, 80, 87, 88, 92, 97, 98, 99, 103, 109, 110,
      130, 133, 141, 147, 150, 159, 162, 165, 169, 172, 174, 179, 182
<223> OTHER INFORMATION: c, t, a or g
<221> NAME/KEY: unsure
<222> LOCATION: 184, 190, 194, 195, 200, 202, 207, 209
<223> OTHER INFORMATION: c, t, a or g
<221> NAME/KEY: misc_feature
<222> LOCATION: (1)...(304)
<223> OTHER INFORMATION: n = A,T,C or G

<400> SEQUENCE: 42

```
tncatangcc ctgaggtggg gacgaagccc gagtccgtcc tgacatgttt ccagtggaaa      60
agattttgtt ntgagcgttn ctttctnntt tnttttnnnt tgnttgttnn atgttttgt     120 tgttgttttn ttnaaactgt ntgttgncan ttcaacatna anggnaggna antntgtgnc    180
tncnttgcan tgtnncatgn tncccananc ccaaaaaaaa aaaaaaaaaa aaaagagta     240 caaatatcac aaaatttgac attttttgtaa taatactttg gttgttgttt ggtgacggcg    300
attg                                                                 304
```